(12) United States Patent
Gao et al.

(10) Patent No.: US 11,758,809 B2
(45) Date of Patent: Sep. 12, 2023

(54) COMPOUND, DISPLAY PANEL, AND DISPLAY APPARATUS

(71) Applicants: Shanghai Tianma AM-OLED Co., Ltd., Shanghai (CN); WUHAN TIANMA MICROELECTRONICS CO., LTD. SHANGHAI BRANCH, Shanghai (CN)

(72) Inventors: Wei Gao, Shanghai (CN); Wenjing Xiao, Shanghai (CN); Lei Zhang, Shanghai (CN); Jinghua Niu, Shanghai (CN); Wenpeng Dai, Shanghai (CN)

(73) Assignees: Shanghai Tianma AM-OLED Co., Ltd., Shanghai (CN); WUHAN TIANMA MICROELECTRONICS CO., LTD. SHANGHAI BRANCH, Shanghai (CN)

( * ) Notice: Subject to any disclaimer, the term of this patent is extended or adjusted under 35 U.S.C. 154(b) by 722 days.

(21) Appl. No.: 16/732,153

(22) Filed: Dec. 31, 2019

(65) Prior Publication Data
US 2021/0098712 A1 Apr. 1, 2021

(30) Foreign Application Priority Data
Sep. 30, 2019 (CN) .......................... 201910939761.6

(51) Int. Cl.
| | | |
|---|---|---|
| C07D 209/86 | (2006.01) | |
| H10K 85/60 | (2023.01) | |
| C07D 401/14 | (2006.01) | |
| C07D 403/14 | (2006.01) | |
| C07F 5/02 | (2006.01) | |

(Continued)

(52) U.S. Cl.
CPC ....... *H10K 85/6572* (2023.02); *C07D 209/86* (2013.01); *C07D 401/14* (2013.01); *C07D 403/14* (2013.01); *C07F 5/027* (2013.01); *C09K 11/06* (2013.01); *H10K 85/322* (2023.02); *H10K 85/654* (2023.02); *C09K 2211/1018* (2013.01); *H10K 50/11* (2023.02); *H10K 50/121* (2023.02); *H10K 2101/10* (2023.02)

(58) Field of Classification Search
CPC .................................................. H10K 85/654
See application file for complete search history.

(56) References Cited

U.S. PATENT DOCUMENTS 11,665,959 B2 * 5/2023 Zhang .................. C07D 403/14
428/690

FOREIGN PATENT DOCUMENTS

| | | |
|---|---|---|
| CN | 101124292 A | 2/2008 |
| CN | 103087068 A | 5/2013 |

(Continued)

OTHER PUBLICATIONS

Office Action dated May 15, 2020, for Chinese Patent Application No. 201910939761.6. (with English translation, 17 pages).

(Continued)

*Primary Examiner* — Alexander R Pagano
(74) *Attorney, Agent, or Firm* — CHRISTENSEN O'CONNOR JOHNSON KINDNESS PLLC

(57) ABSTRACT

A compound having a structure shown in Chemical Formula 1 is described. In an embodiment, Ar is C6-C20 aryl or C5-C20 heteroaryl; $D_1$ and $D_2$ are electron-donating groups, $A_1$ and $A_2$ are electron-accepting groups, and m, n, p and q are 1, 2, or 3; $D_1$ and $D_2$ are a substituted or unsubstituted C1-C20 alkyl, a substituted or unsubstituted C3-C20 cycloalkyl, a substituted or unsubstituted C1-C20 alkoxy, a substituted or unsubstituted C3-C20 heterocyclic group, a substituted or unsubstituted C6-C40 aryl, a substituted or unsubstituted C4-C40 heteroaryl, a substituted or unsubstituted C10-C60 fused aryl, a substituted or unsubstituted C10-C60 fused heteroaryl, a substituted or unsubstituted C12-C40 carbazolyl, a substituted or unsubstituted C12-C40 diphenylamino group, or a C13-C40 acridinyl; and $A_1$ and $A_2$ are each a nitrogen-containing heterocyclic group, a cyano-containing group, a carbonyl-containing group, a sulfone-based group, and a phosphoroso-containing group.

Chemical Formula 1

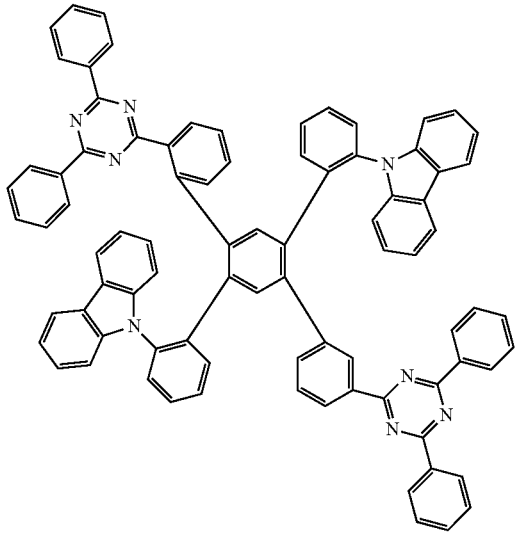

5 Claims, 2 Drawing Sheets

(51) Int. Cl.
*C09K 11/06* (2006.01)
*H10K 85/30* (2023.01)
*H10K 50/11* (2023.01)
*H10K 50/12* (2023.01)
*H10K 101/10* (2023.01)

(56) References Cited

FOREIGN PATENT DOCUMENTS

| CN | 106661001 A | 5/2017 | | |
|---|---|---|---|---|
| CN | 108329252 A | 7/2018 | | |
| KR | 101317531 B1 | 10/2013 | | |
| WO | WO2015175678 | * | 5/2015 | ............ C09K 11/06 |
| WO | 2016/116487 A1 | 7/2016 | | |
| WO | 2016/197353 A1 | 12/2016 | | |

OTHER PUBLICATIONS

Second Office Action dated Nov. 24, 2020, in Chinese Patent Application No. 201910939761.6 (with English translation), 19 pages.

\* cited by examiner

COMPOUND, DISPLAY PANEL, AND DISPLAY APPARATUS

CROSS-REFERENCE TO RELATED APPLICATIONS

The present application claims priority to Chinese Patent Application No. 201910939761.6, filed on Sep. 30, 2019, the content of which is incorporated herein by reference in its entirety.

TECHNICAL FIELD

The present disclosure relates to the technical field of organic electroluminescent materials, and in particular to a compound having thermally activated delayed fluorescence (TADF) properties, a display panel including the compound, and a display apparatus.

BACKGROUND

With the rapid development of electronic display technology, Organic Light-emitting Diodes (OLEDs) are widely used in various display devices, and research on light-emitting materials of OLEDs is also more intensive.

Based on the light-emitting mechanism, materials applied in a light-emitting layer of the OLED can be mainly divided into four types:

(1) fluorescent materials; (2) phosphorescent materials; (3) triplet-triplet annihilation (TTA) materials; (4) thermally activated delayed fluorescence (TADF) materials.

Regarding fluorescent materials, according to spin-statistics, a ratio of singlet excitons to triplet excitons is 1:3, and thus the maximum internal quantum yield of fluorescent materials does not exceed 25%. According to the Lambertian luminescence mode, the light extraction efficiency is about 20%, and thus an External Quantum Efficiency (EQE) of the OLED device based on the fluorescent material does not exceed 5%.

For the phosphorescent materials, due to its heavy atom effect, the phosphorescent materials can intensify inter-system in the molecule through spin-coupling, and 75% of triplet excitons can be directly utilized to achieve emission at room temperature with both S1 and T1 states participating therein. With the theoretical maximum internal quantum yield reaching 100%. According to the Lambertian luminescence mode, the light extraction efficiency is about 20%, thus the EQE of the OLED device based on the phosphorescent materials can reach 20%. However, the phosphorescent materials are generally complexes of a heavy metal, such as Ir, Pt, Os, Re, Ru, etc., and are characterized by high production cost, which is not conducive to large-scale production. Under the condition of high electric current density, the phosphorescent materials show a phenomenon of dramatic efficiency roll-off, and the stability of phosphorescent devices is not good.

Regarding TAA materials, two adjacent triplet excitons are combined to form a singlet excited state molecule with higher energy level and a ground state molecule. However, since the two triplet excitons merely produce one singlet state exciton, the theoretical maximum internal quantum yield can only reach 62.5%. In order to prevent the substantial decrease in efficiency, a concentration of triplet excitons should be regulated during this process.

For the TADF materials, when an energy level difference between the singlet excited state and the triplet excited state is relatively small, a reverse intersystem crossing (RISC) may occur among the molecules, and the excitons are converted from a T1 state to an S1 state by absorbing ambient heat, so that 75% of triplet excitons and 25% of singlet excitons can be utilized at the same time. In this way, the theoretical maximum internal quantum yield can reach 100%. The TADF materials are mainly organic compounds without rare metal element, so that the production cost is relatively low. The TADF materials can be chemically modified by various methods. However, there are few TADF materials that have been discovered so far. Accordingly, there is a pressing need to develop new TADF materials applicable in OLED devices.

SUMMARY

In view of the above, the present disclosure provides a compound having thermally activated delayed fluorescence (TADF) properties. The compound has a structure shown in Chemical Formula 1:

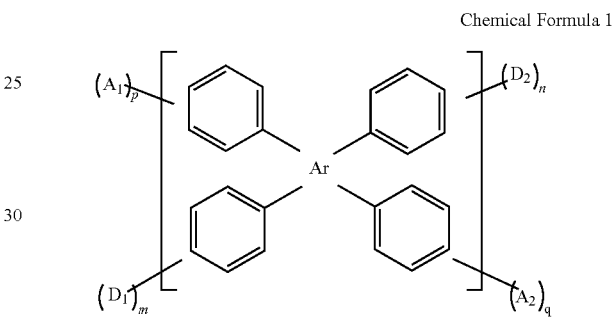

Chemical Formula 1 wherein Ar is C6-C20 aryl or C5-C20 heteroaryl;

$D_1$ and $D_2$ are each an electron-donating group, and m and n are each an integer independently selected from 1, 2, and 3;

$A_1$ and $A_2$ are each an electron-accepting group, and p and q are each an integer independently selected from 1, 2, and 3;

$D_1$, $D_2$, $A_1$, and $A_2$ are connected to benzene rings, respectively, each of the benzene rings being bonded connected to Ar;

$D_1$ and $D_2$ are each independently selected from the group consisting of a substituted or unsubstituted C1-C20 alkyl group, a substituted or unsubstituted C3-C20 cycloalkyl group, a substituted or unsubstituted C1-C20 alkoxy group, a substituted or unsubstituted C3-C20 heterocyclic group, a substituted or unsubstituted C6-C40 aryl group, a substituted or unsubstituted C4-C40 heteroaryl group, a substituted or unsubstituted C10-C60 fused aryl group, a substituted or unsubstituted C10-C60 fused heteroaryl group, a substituted or unsubstituted C12-C40 carbazolyl group and derivative groups thereof, a substituted or unsubstituted C12-C40 diphenylamino group and derivative groups thereof, a C13-C40 acridinyl group and derivative groups thereof, and combinations thereof;

$A_1$ and $A_2$ are each independently selected from the group consisting of a nitrogen-containing heterocyclic group, a cyano-containing group, a carbonyl-containing group, a sulfone-based group, and a phosphoroso-containing group.

The present disclosure also provides a display panel, including an organic light-emitting device. The organic light-emitting device includes an anode, a cathode disposed opposite to the anode, and a light-emitting layer disposed between the anode and the cathode. A light-emitting material of the light-emitting layer comprises a host material and a guest material, and the guest material or the host material is one or more compounds according to the present disclosure.

The present disclosure further provides a display apparatus, including the display panel according to the present disclosure.

DESCRIPTION OF EMBODIMENTS

Figure 1:
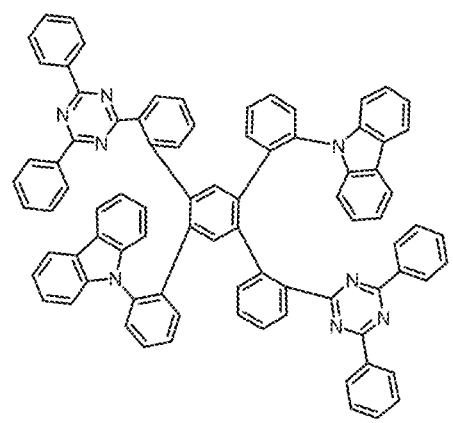
FIG. 1 is a chemical structure of a representative compound P1 provided by an embodiment of the present disclosure.
Figure 2:
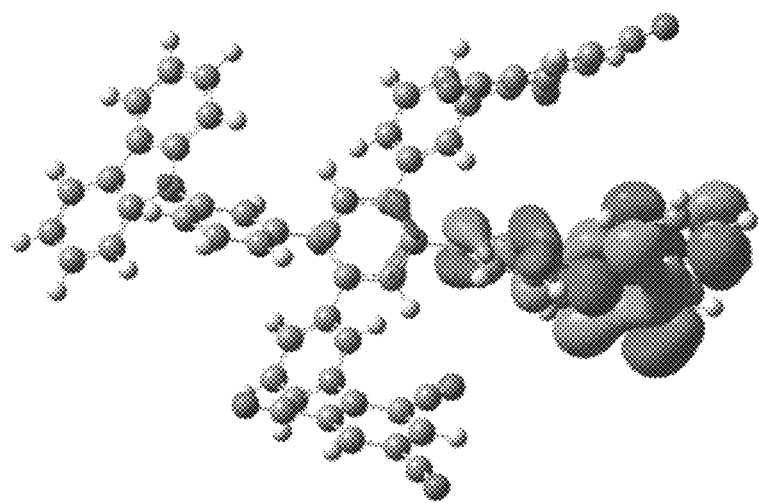
FIG. 2 is a HOMO distribution diagram of a representative compound P39 provided by an embodiment of the present disclosure.

The present disclosure is further described by the following examples and comparative examples, which are merely intended to illustrate, but not to limit the present disclosure.

In an aspect of the present disclosure provides a compound having a structure shown in Chemical Formula 1:

Chemical Formula 1

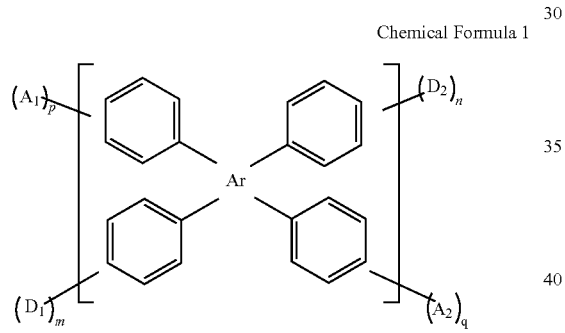

where Ar is C6-C20 aryl or C5-C20 heteroaryl;

$D_1$ and $D_2$ are each an electron-donating group, and m and n are each an integer independently selected from 1, 2, or 3;

$A_1$ and $A_2$ are each an electron-accepting group, and p and q are each an integer independently selected from 1, 2, or 3;

$D_1$, $D_2$, $A_1$ and $A_2$ are connected to benzene rings connected to Ar, respectively; $D_1$ and $D_2$ are each independently selected from the group consisting of a substituted or unsubstituted C1-C20 alkyl group, a substituted or unsubstituted C3-C20 cycloalkyl group, a substituted or unsubstituted C1-C20 alkoxy group, a substituted or unsubstituted C3-C20 heterocyclic group, a substituted or unsubstituted C6-C40 aryl group, a substituted or unsubstituted C4-C40 heteroaryl group, a substituted or unsubstituted C10-C60 fused aryl group, a substituted or unsubstituted C10-C60 fused heteroaryl group, a substituted or unsubstituted C12-C40 carbazolyl group and derivative groups thereof, a substituted or unsubstituted C12-C40 diphenylamino group and derivative groups thereof, a C13-C40 acridinyl group and derivative groups thereof, and combinations thereof;

$A_1$ and $A_2$ are each independently selected from the group consisting of a nitrogen-containing heterocyclic group, a cyano-containing group, a carbonyl-containing group, a sulfone-based group, and a phosphoroso-containing group.

According to an embodiment of the compound of the present disclosure, the compound has any one of the following chemical structures:

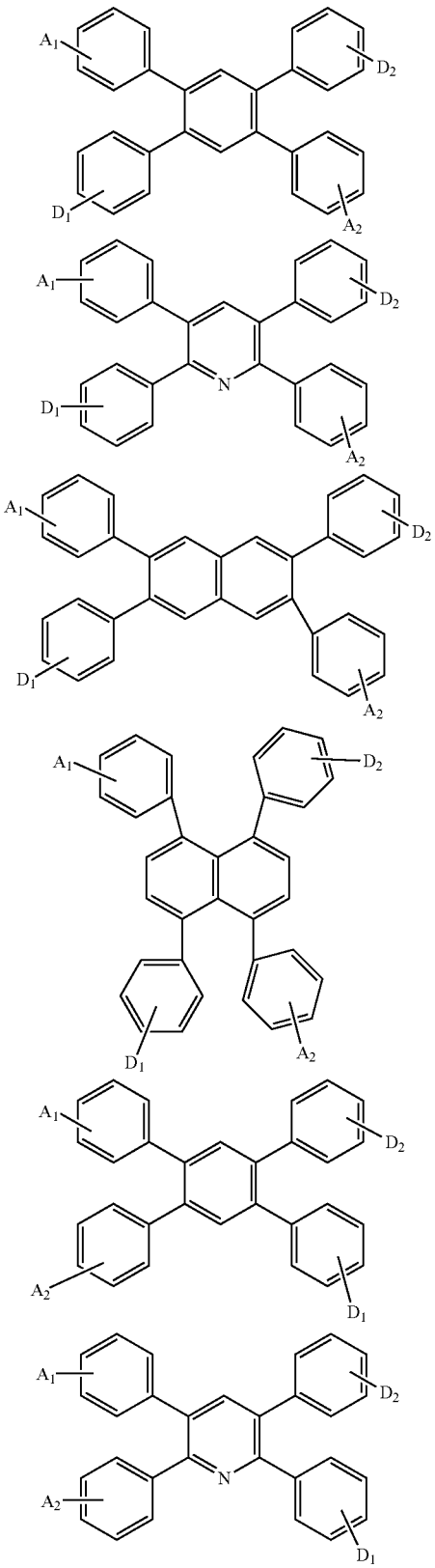

-continued

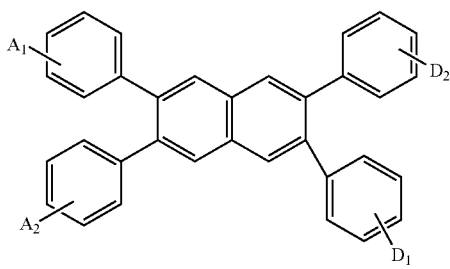

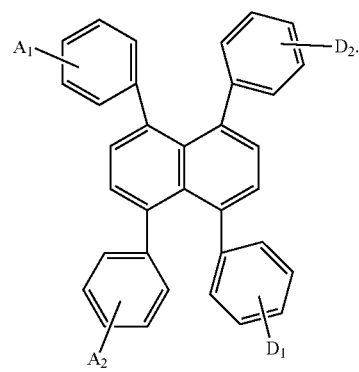

According to an embodiment of the compound of the present disclosure, the compound has any one of the following chemical structures:

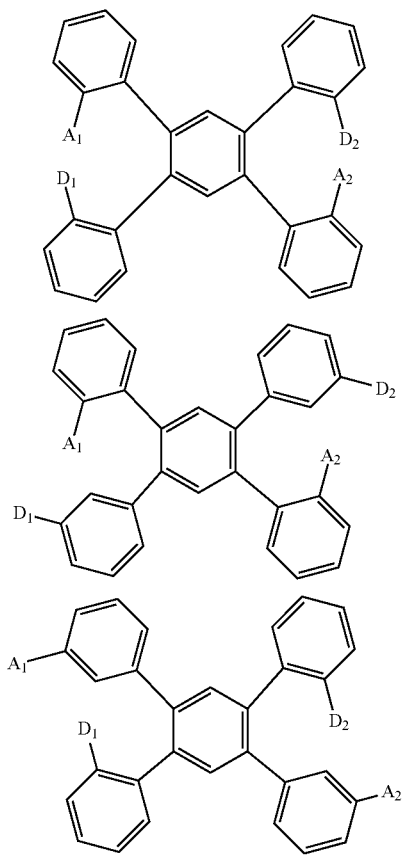

-continued

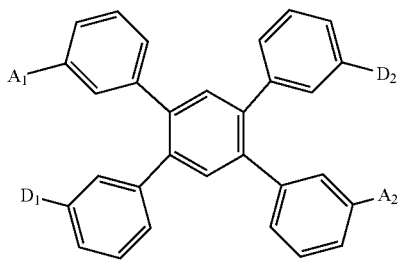

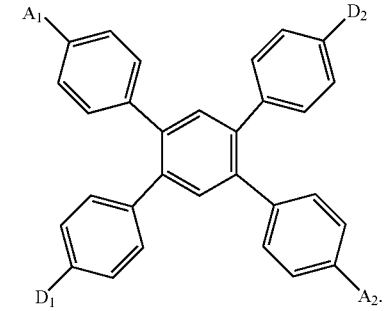

According to an embodiment of the compound of the present disclosure, $A_1$ and $A_2$ are identical, and $D_1$ and $D_2$ are identical. When $A_1$ and $A_2$ are identical, and $D_1$ and $D_2$ are identical, the compound has a symmetrical structure and can be synthesized in an easier way with a lower production cost.

According to one embodiment of the compound of the present disclosure, $D_1$ and $D_2$ are each independently selected from the group consisting of the following groups:

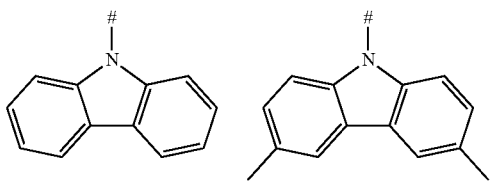

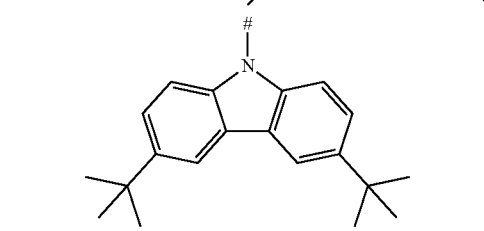

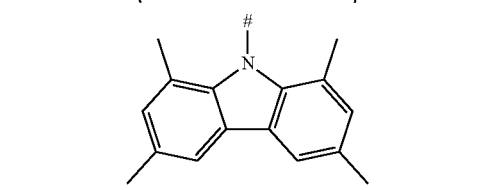

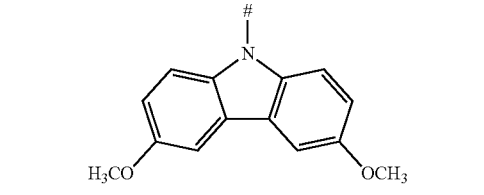

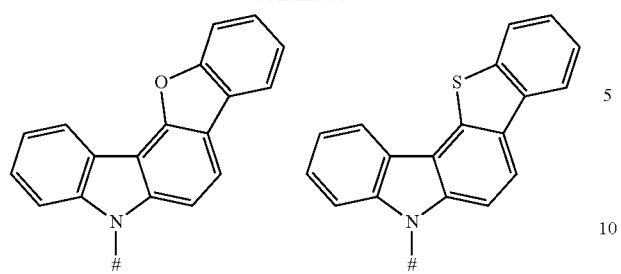
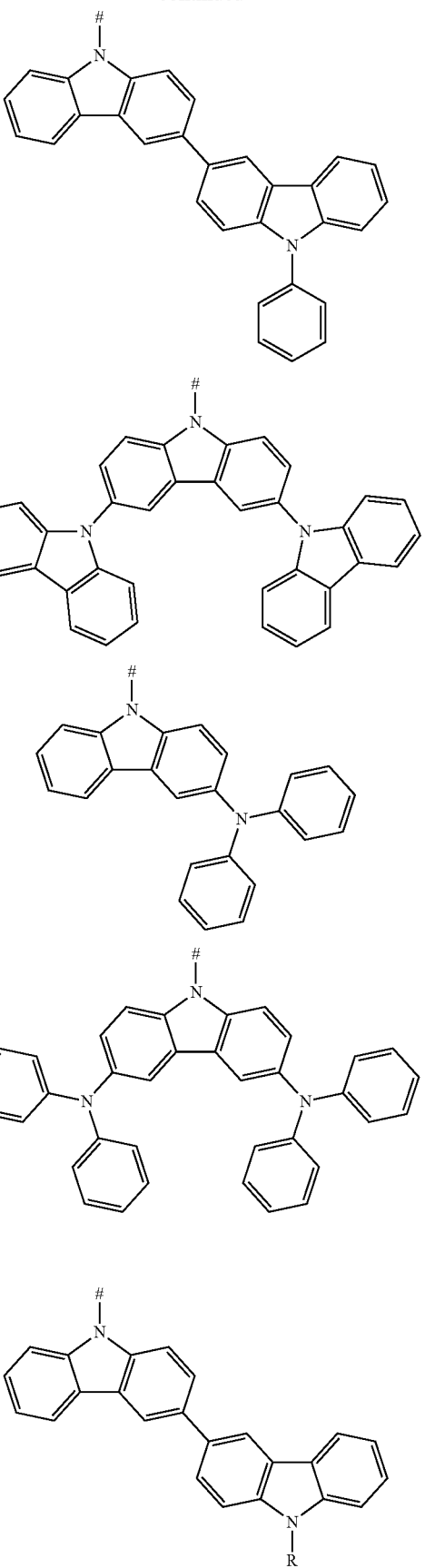

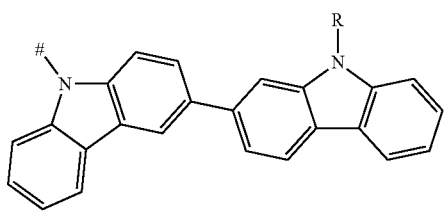

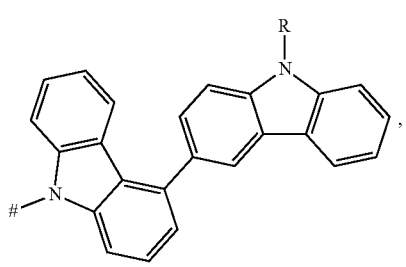

in which, # represents a bonding position in the Chemical Formula 1, and R is a C1-C20 alkyl group, a C1-C20 alkoxy group, a C2-C20 alkenyl group, a C2-C20 alkynyl group, a C6-C40 aromatic group, or a C4-C40 heteroaryl group.

According to an embodiment of the compound of the present disclosure, $D_1$ and $D_2$ are each independently selected from the group consisting of the following groups:

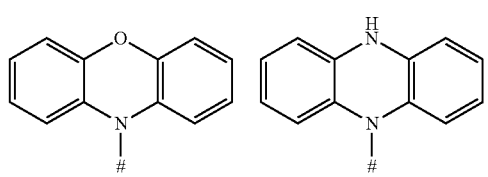

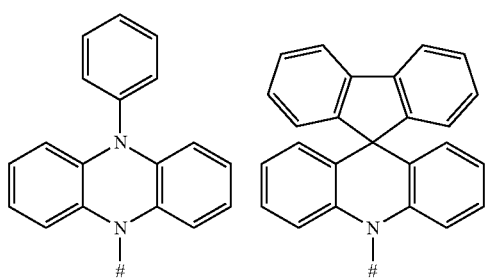

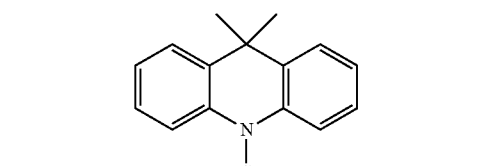

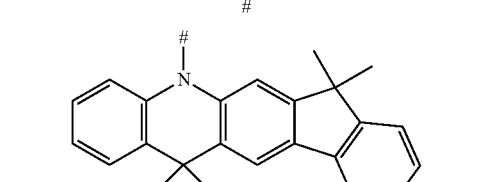

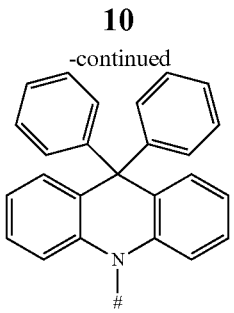

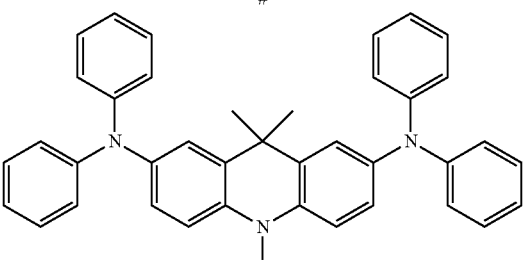

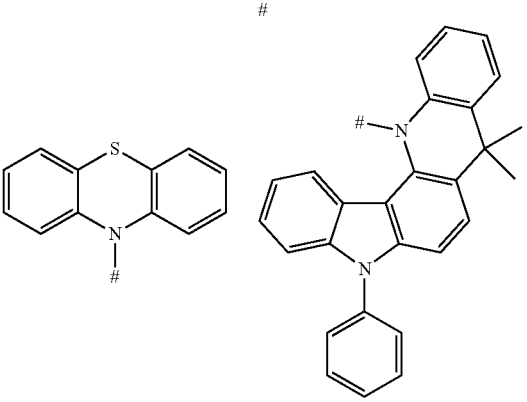

in which, # is a bonding position in the Chemical Formula 1.

According to one embodiment of the compound of the present disclosure, $D_1$ and $D_2$ are each independently selected from the group consisting of the following groups:

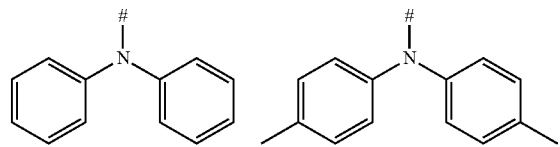
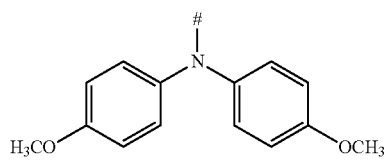
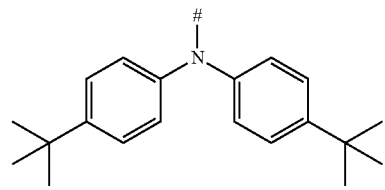
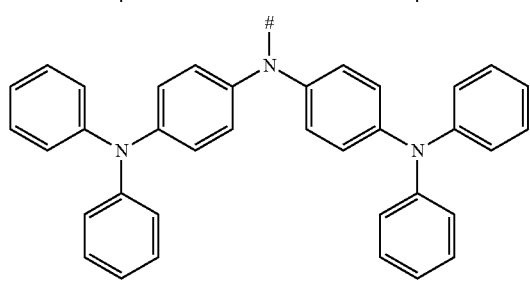
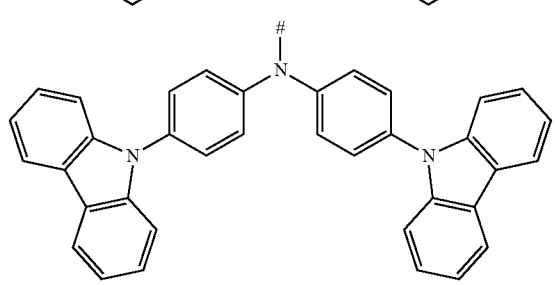
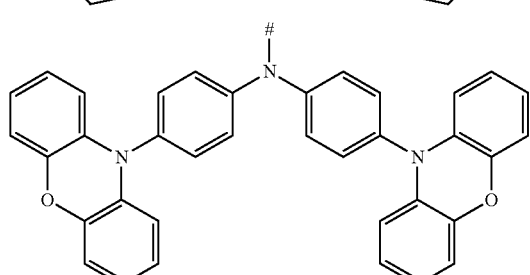
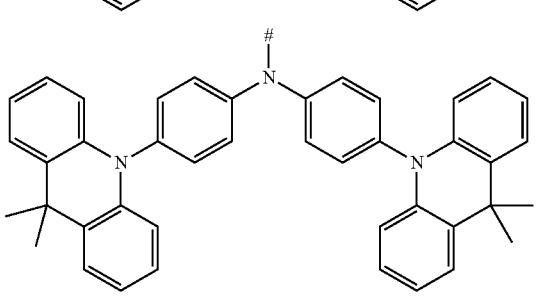
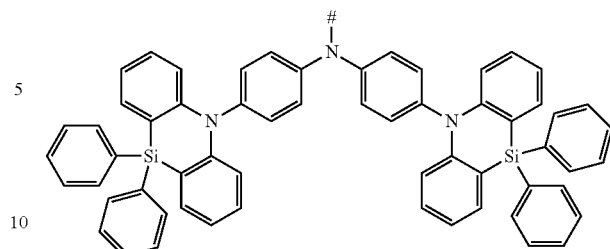
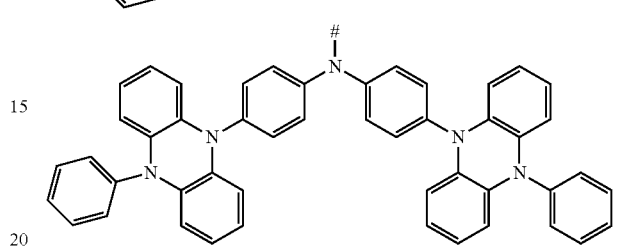
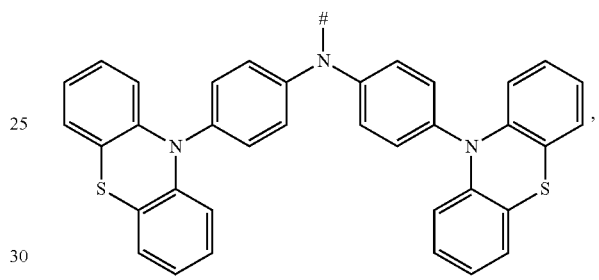

in which, # is a bonding position in the Chemical Formula 1.

According to one embodiment of the compound of the present disclosure, $D_1$ and $D_2$ are each independently selected from the group consisting of the following groups:

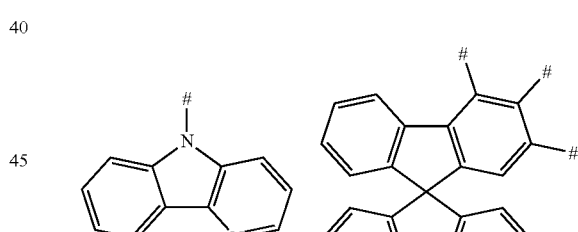
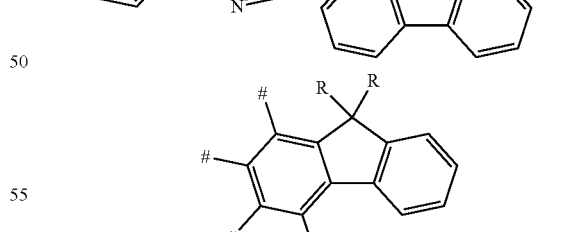
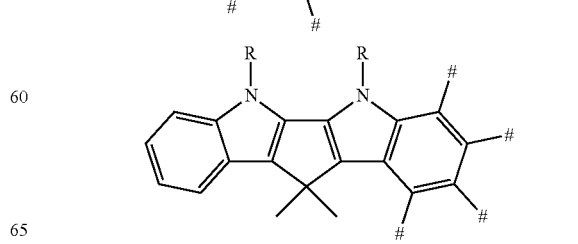

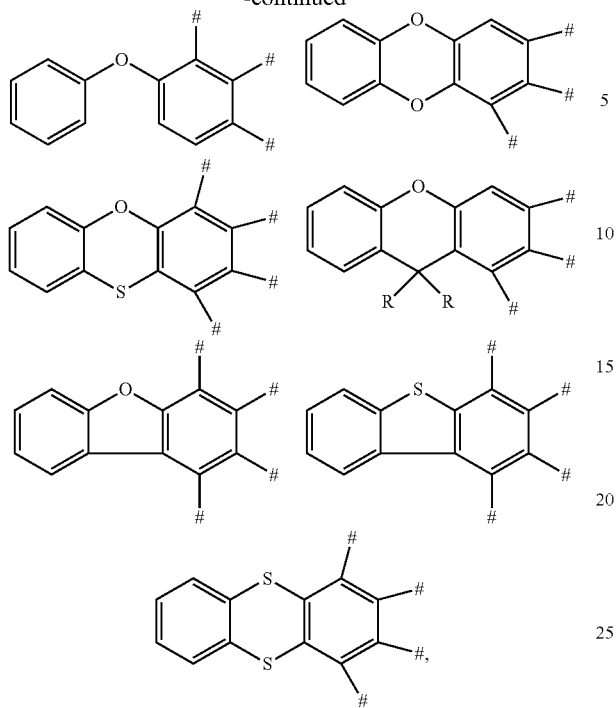

in which # represents a bonding position in the Chemical Formula 1, and R is a C1-C20 alkyl group, a C1-C20 alkoxy group, a C2-C20 alkenyl group, a C2-C20 alkynyl group, a C6-C40 aromatic group, or a C4-C40 heteroaryl group.

According to one embodiment of the compound of the present disclosure, the nitrogen-containing heterocyclic group is selected from the group consisting of the following groups:

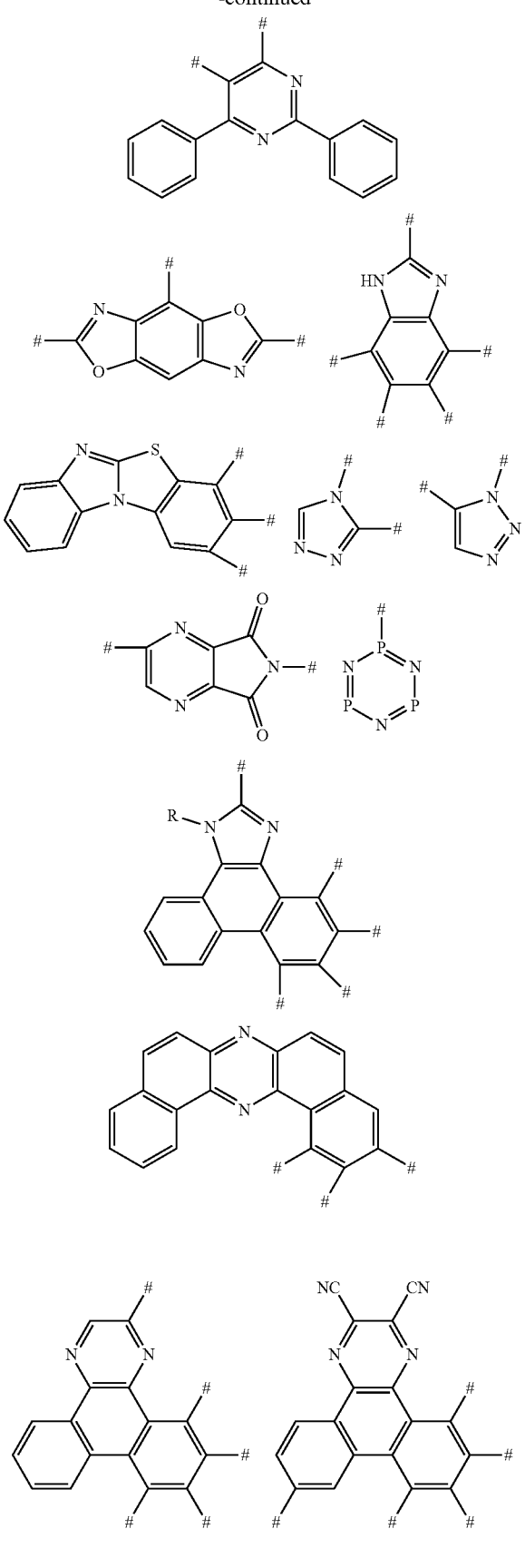

-continued

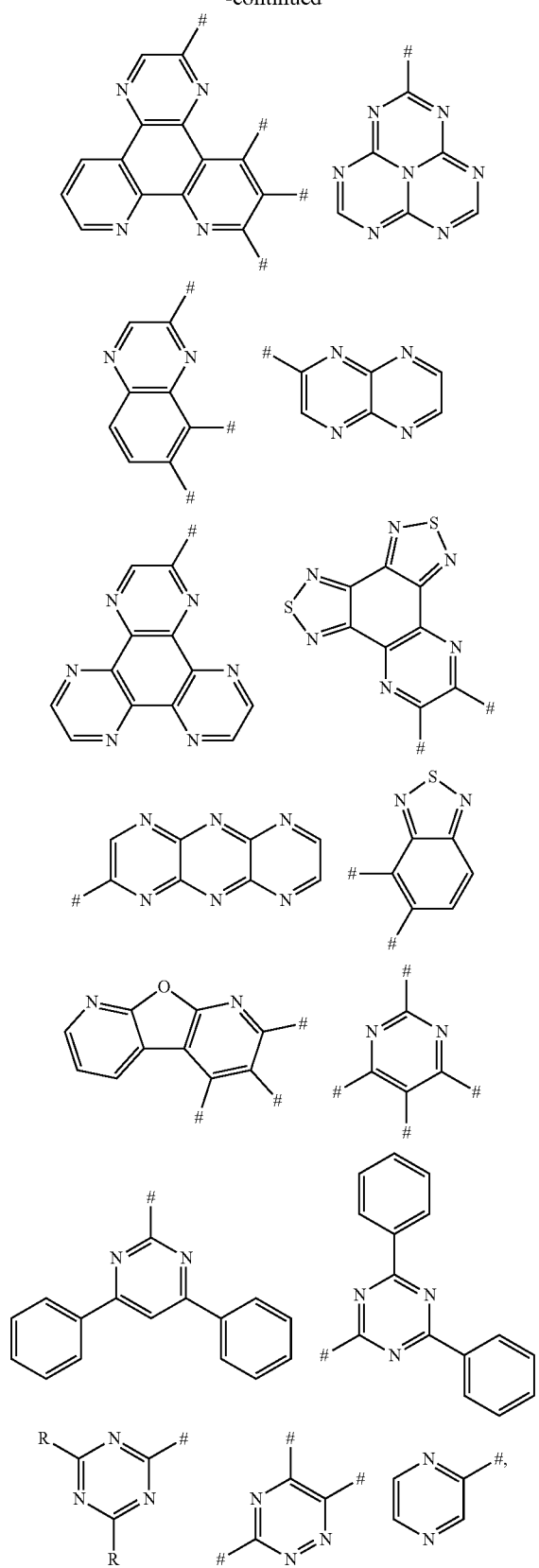

in which # represents a bonding position in the Chemical Formula 1; and R is selected from the group consisting of a hydrogen atom, a C1-C20 alkyl group, a C1-C20 alkoxy group, a C4-C8 cycloalkyl group, a C6-C40 aryl group, and a C4-C40 heteroaryl group According to one embodiment of the compound of the present disclosure, the cyano-containing group is selected from the group consisting of the following groups:

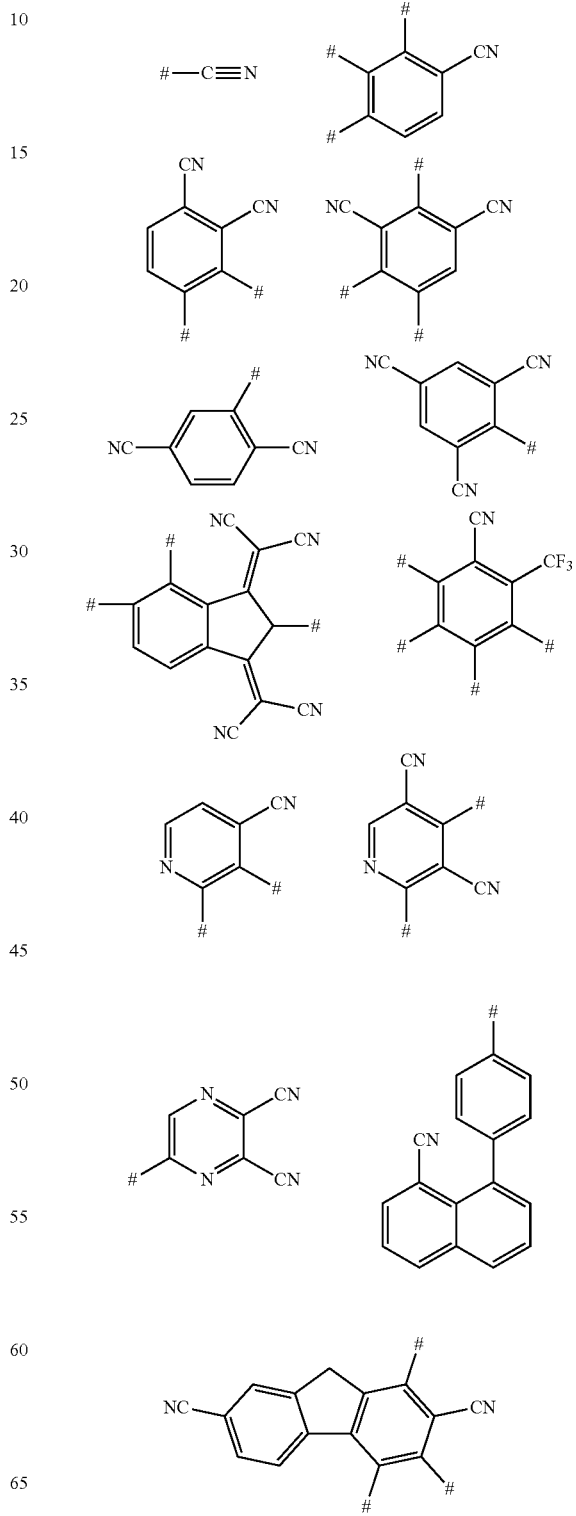

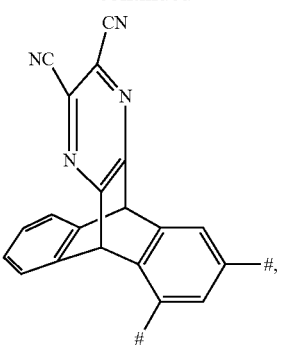
in which # represents a bonding position in the Chemical Formula 1.
According to one embodiment of the compound of the present disclosure, the carbonyl-containing group is selected from the group consisting of the following groups:
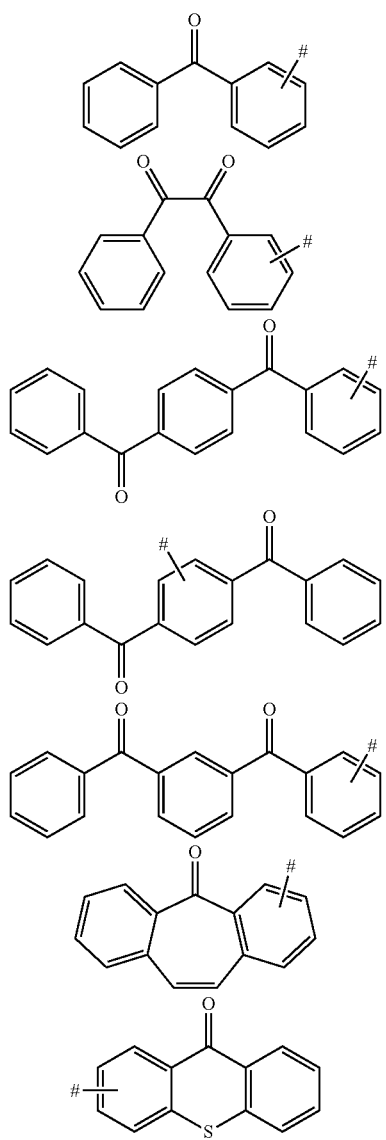
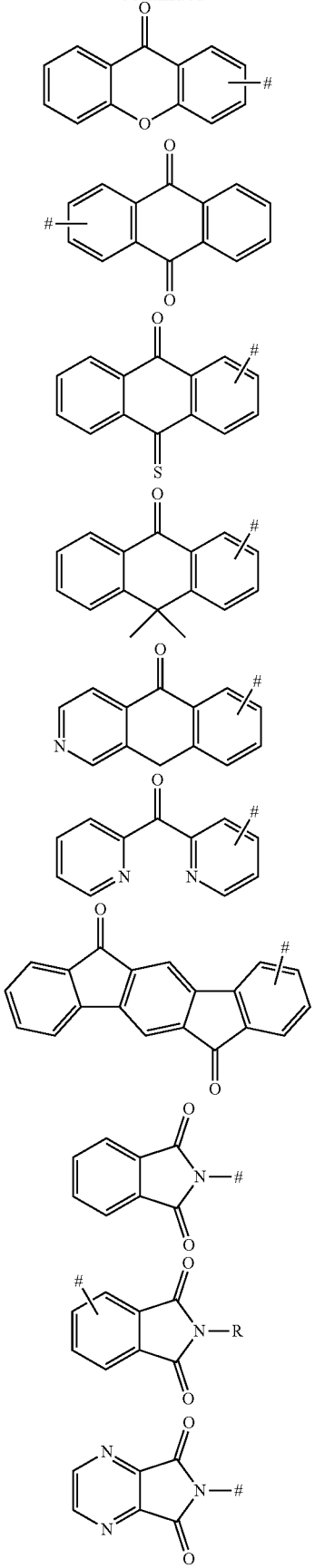

-continued

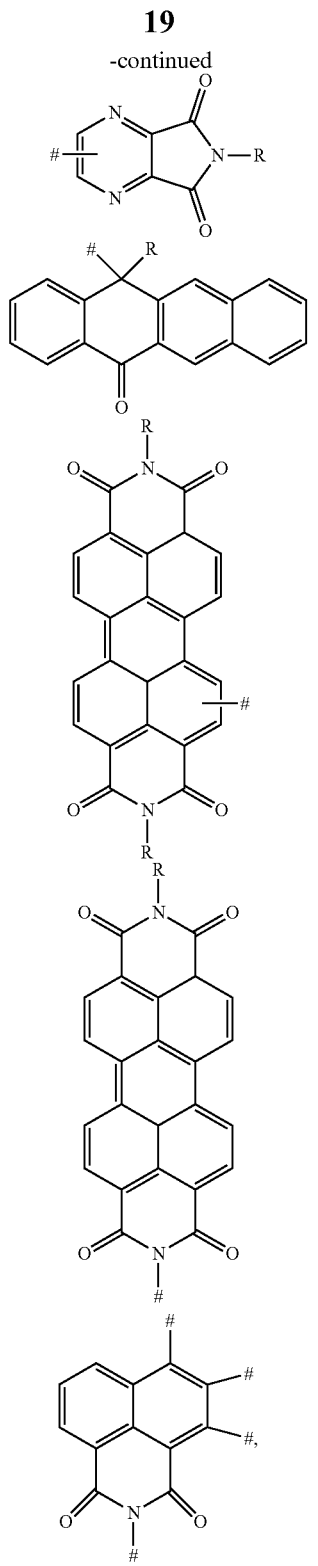

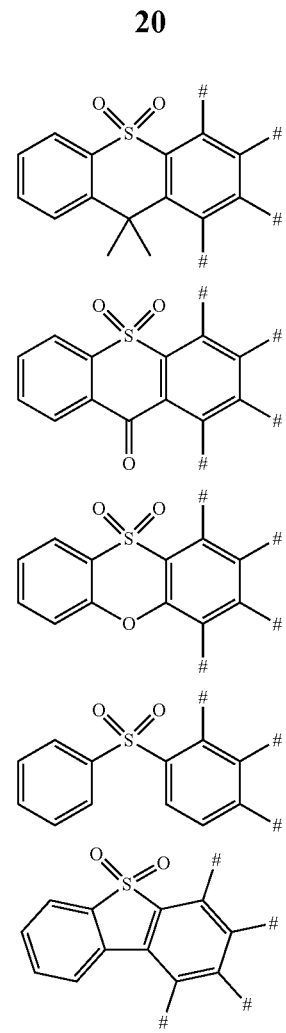

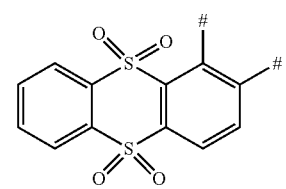

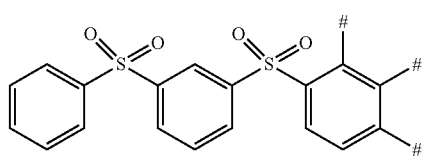

in which # represents a bonding position in the Chemical Formula 1, and R represents a C1-C20 alkyl group, a C1-C20 alkoxy group, a C2-C20 alkenyl group, a C2-C20 alkynyl group, a C4-C8 cycloalkyl group, a C6-C40 aromatic group, or a C4-C40 heteroaryl group.

According to one embodiment of the compound of the present disclosure, the sulfone-containing group is selected from the group consisting of the following groups:

-continued

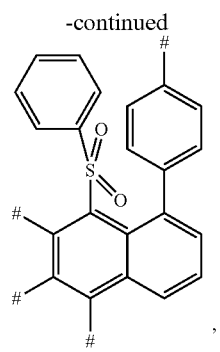

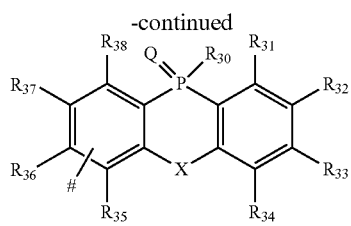

in which # represents a bonding position in the Chemical Formula 1.

According to one embodiment of the compound of the present disclosure, the phosphoroso-containing group is selected from the group consisting of the following groups:

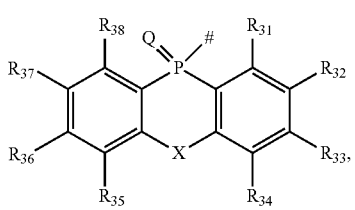

in which, X is selected from the group consisting of O, S, —$BR_{41}$, —$C(R_{41})_2$, —$Si(R_{41})_2$, and —$NR_{41}$; $R_{30}$, $R_{31}$, $R_{32}$, $R_{33}$, $R_{34}$, $R_{35}$, $R_{36}$, $R_{37}$, $R_{38}$, $R_{39}$, $R_{40}$, and $R_{41}$ are each independently selected from the group consisting of a hydrogen atom, a substituted or unsubstituted C1-C20 alkyl group, a substituted or unsubstituted C3-C20 cycloalkyl group, a substituted or unsubstituted C1-C20 alkoxy group, a substituted or unsubstituted C3-C20 heterocyclic group, a substituted or unsubstituted C6-C40 aryl group, and a substituted or unsubstituted C2-C40 heteroaryl group; and # indicates a bonding position in the Chemical Formula 1.

According to one embodiment of the compound of the present disclosure, the compound is selected from the group consisting of the following compounds:

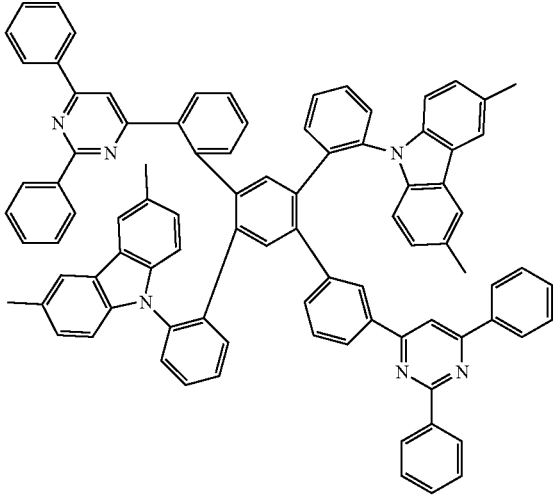

-continued
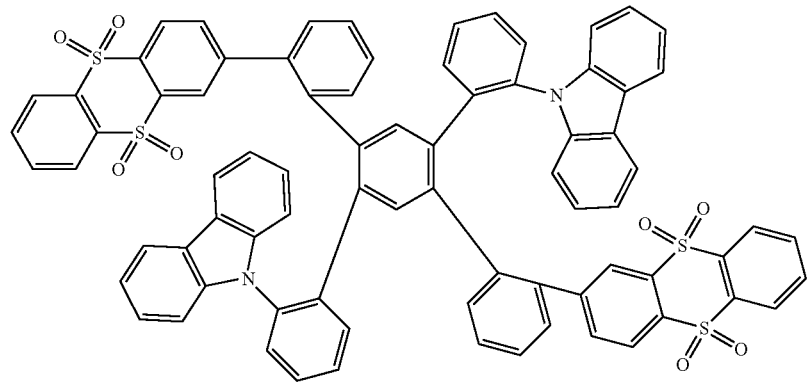
P3
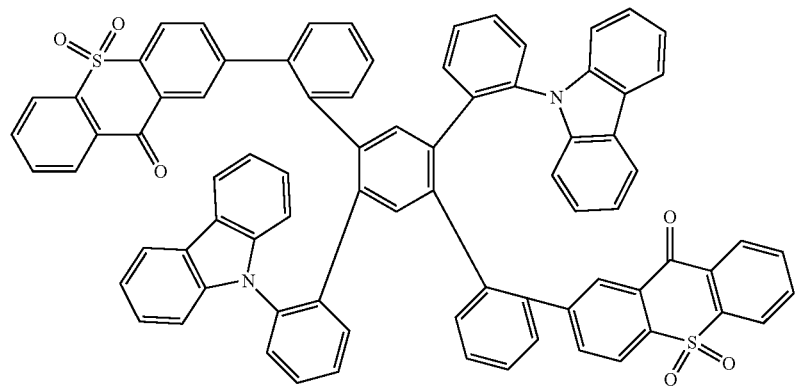
P4
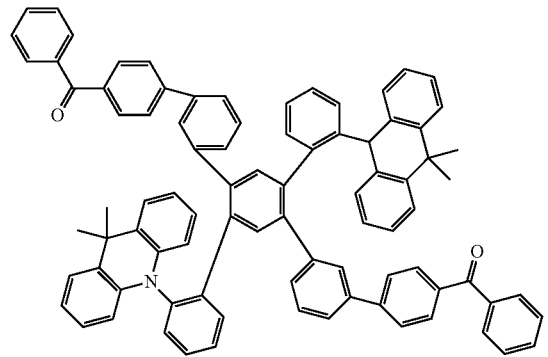
P5
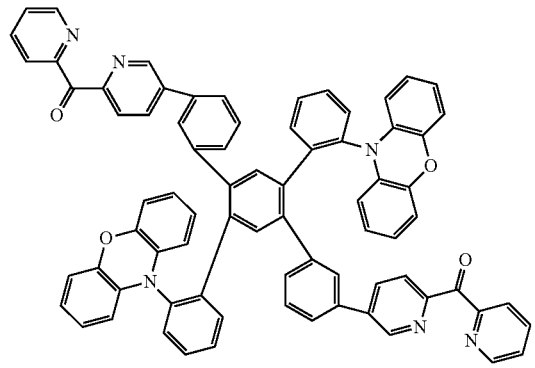
P6
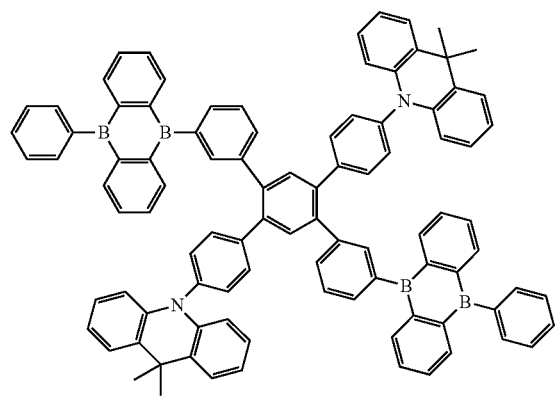
P7
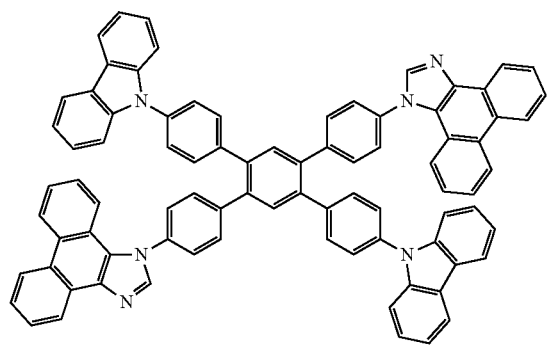
P8

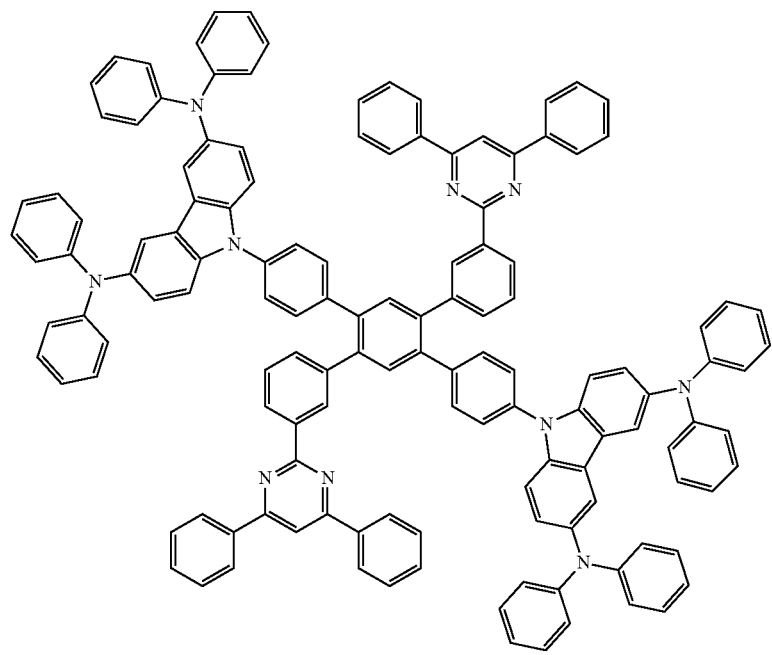
P9
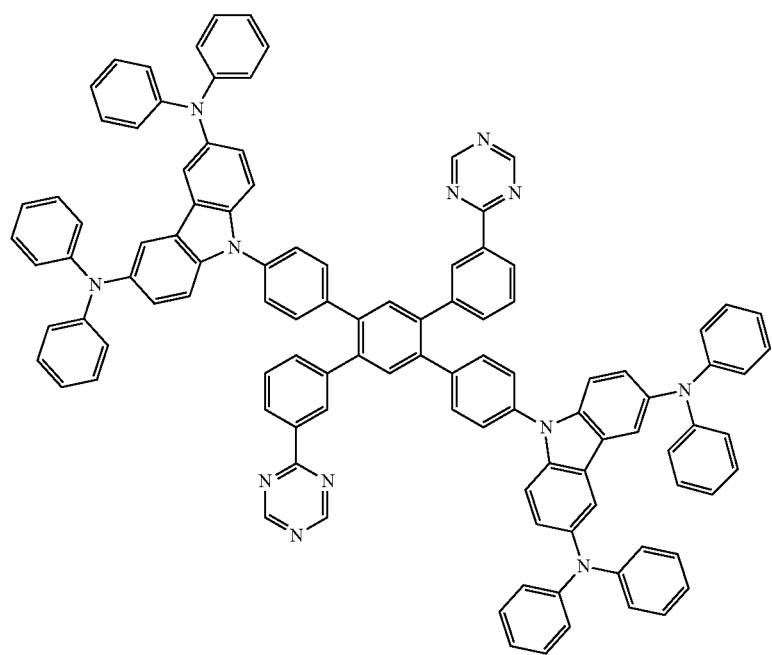
P10

P11
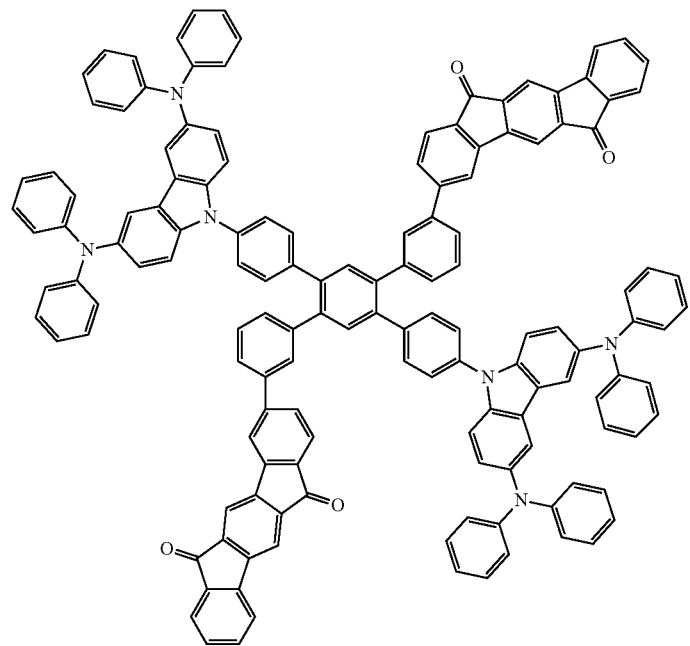
P12
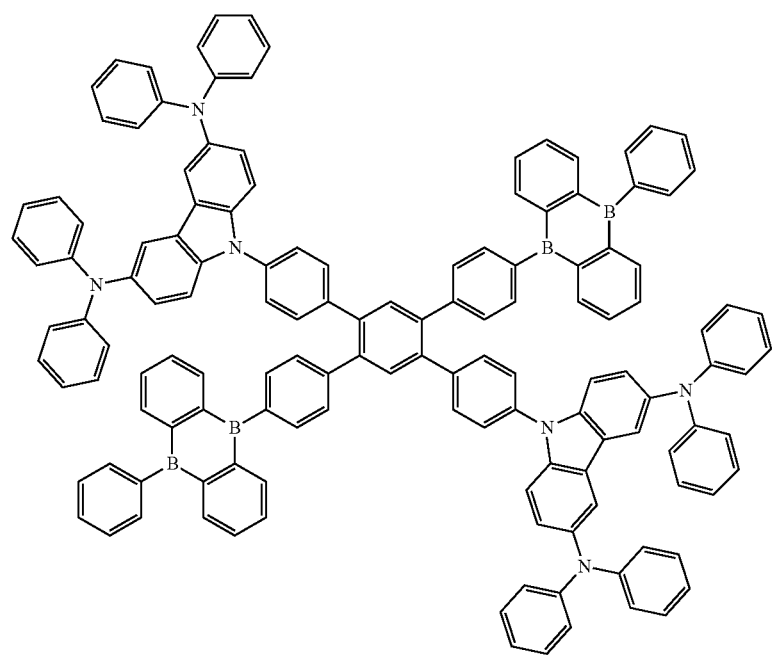

-continued
P13
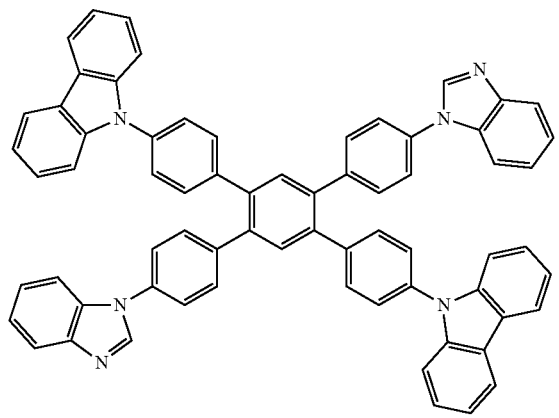
P14
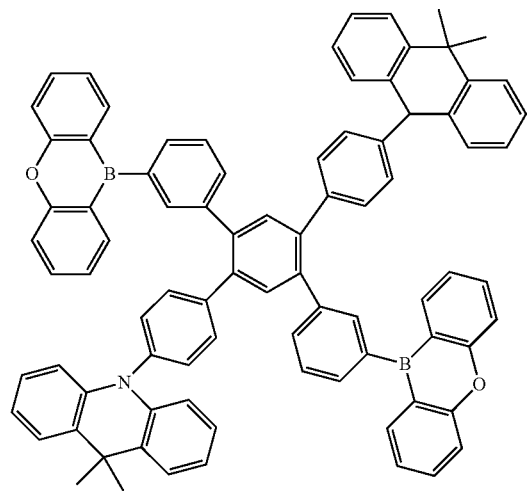
P15
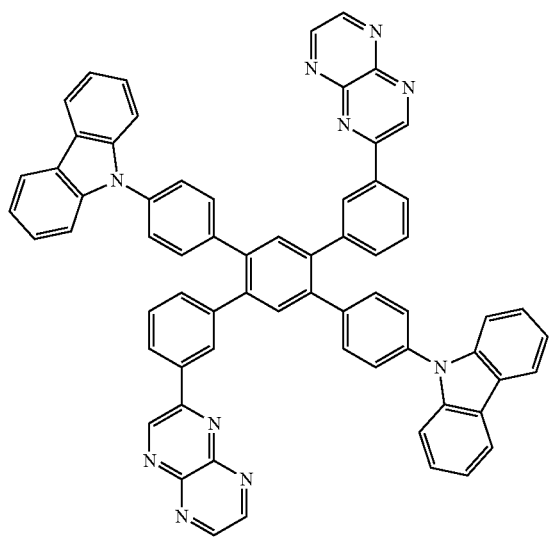
P16
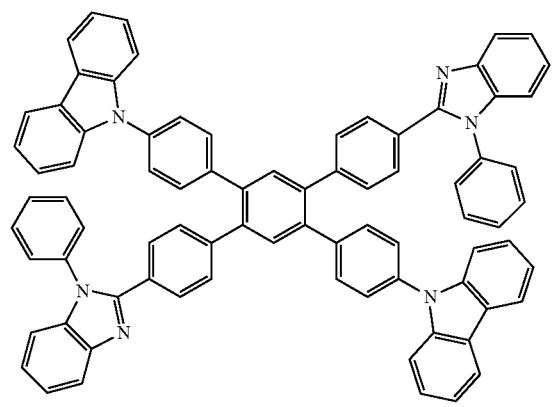
P17
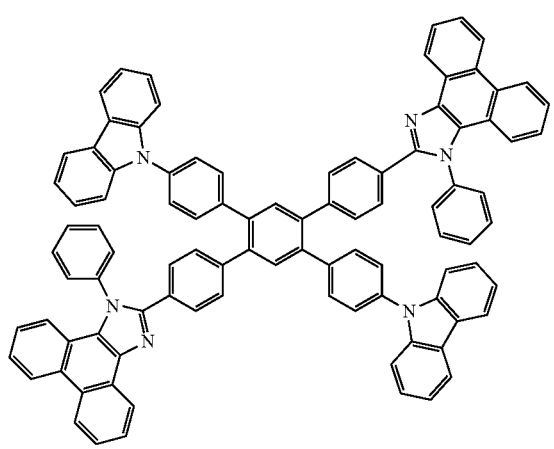
P18
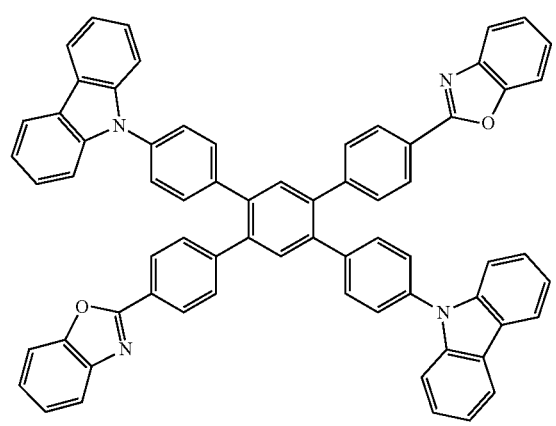

-continued
P19
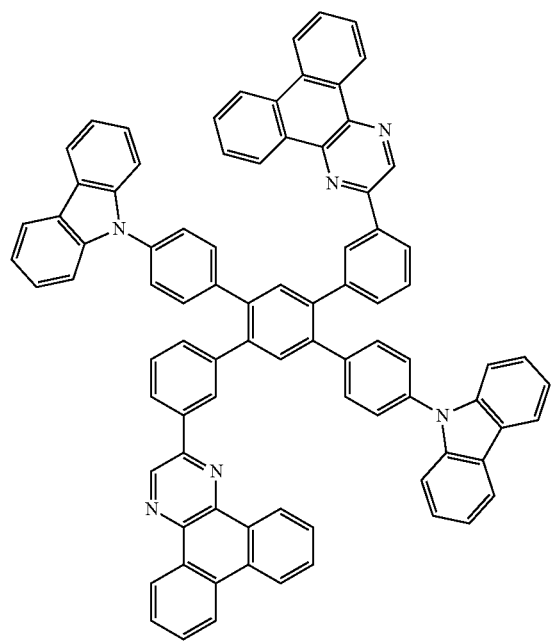
P20
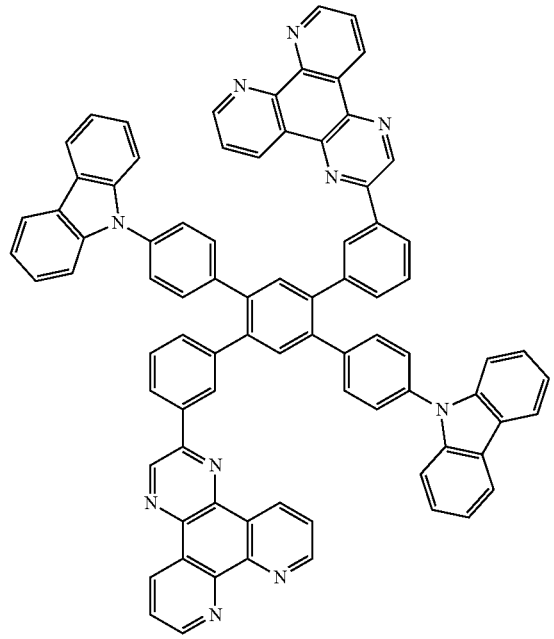
P21
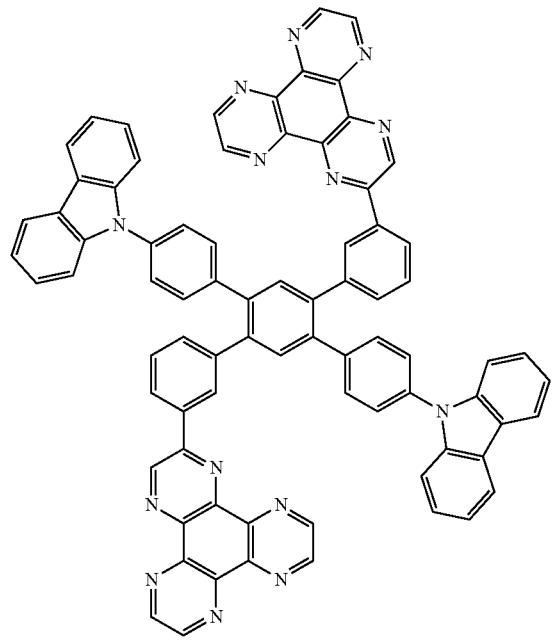
P22
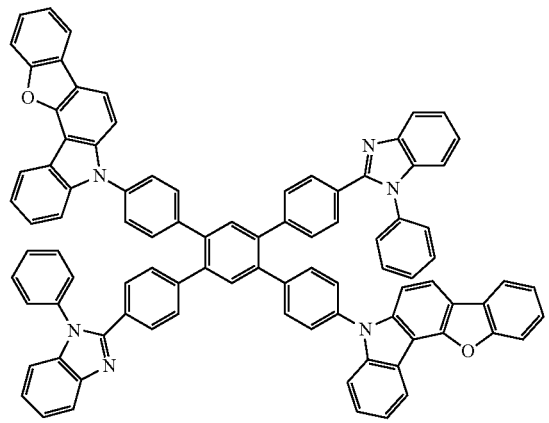

P23
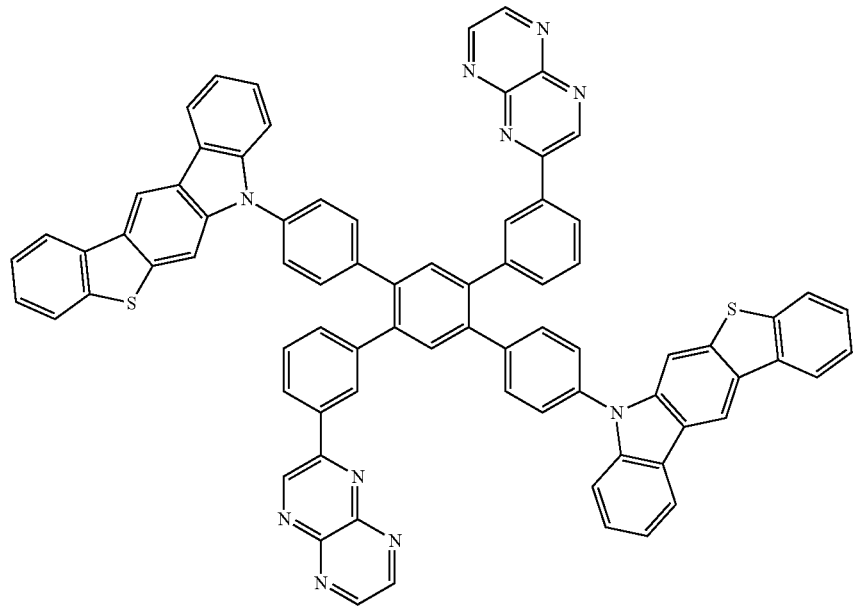
P24
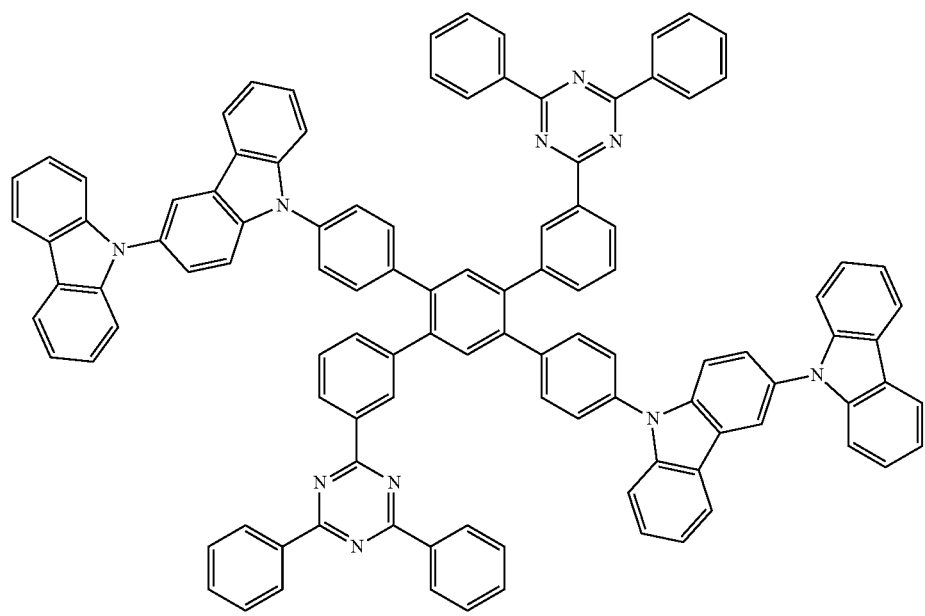

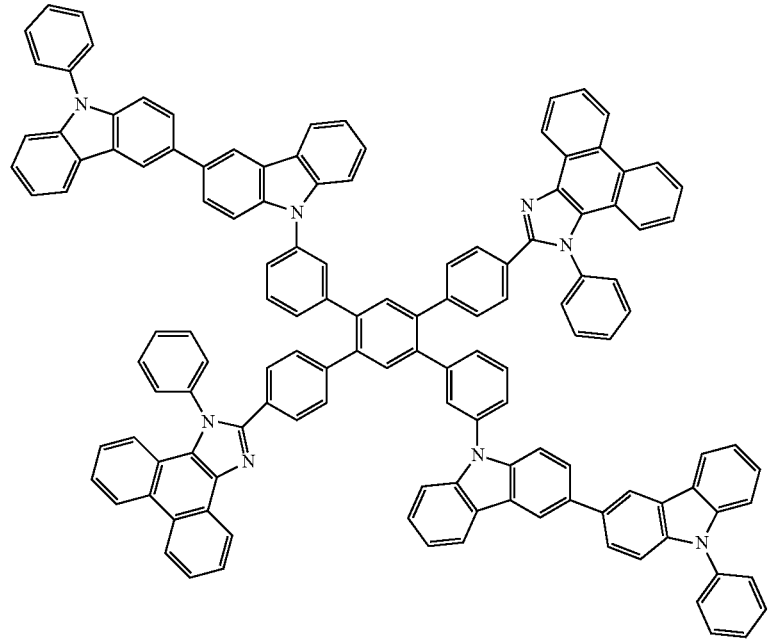
P25
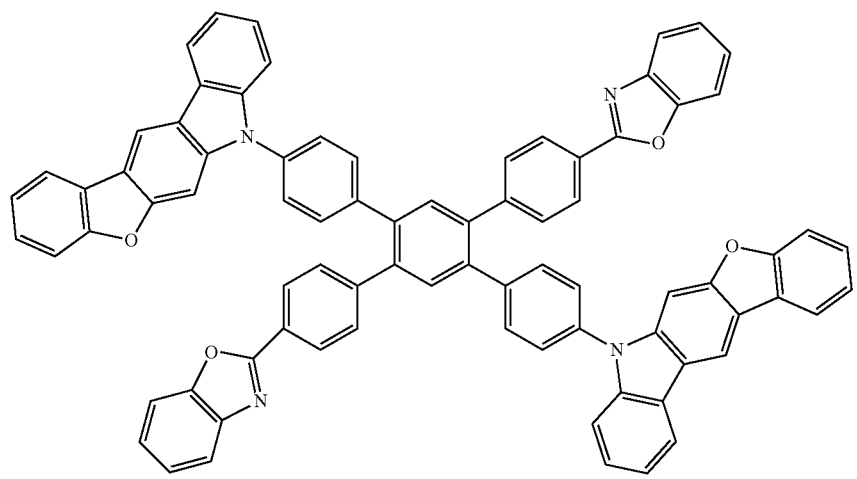
P26

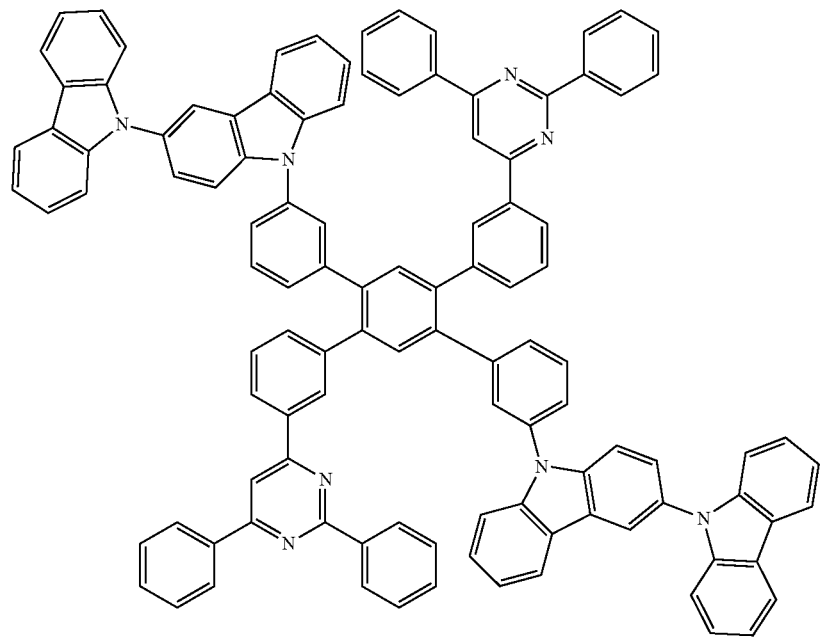
P27
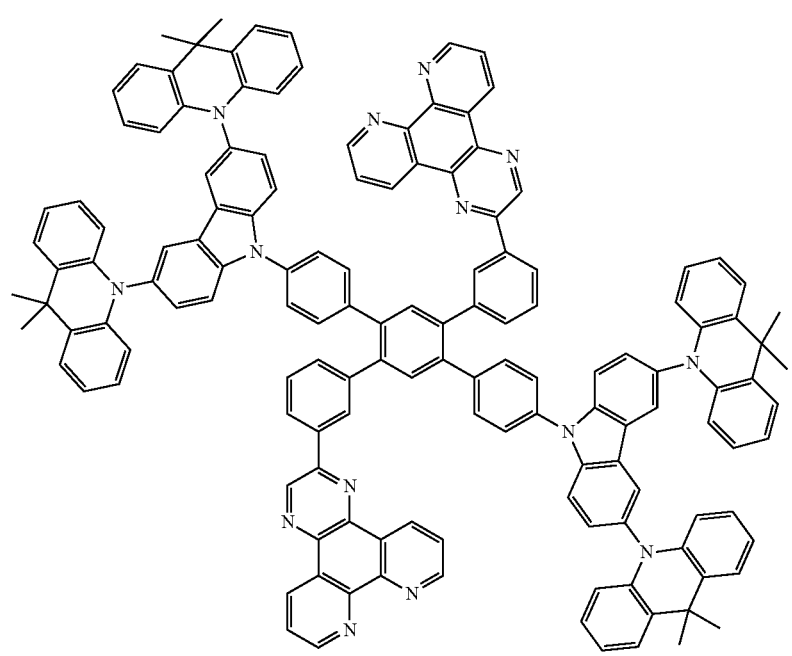
P28

-continued
P29
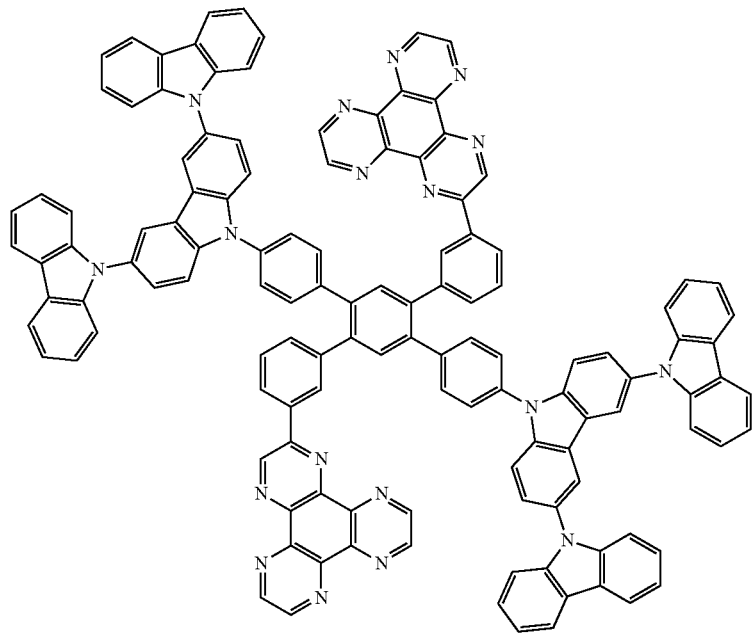
P30
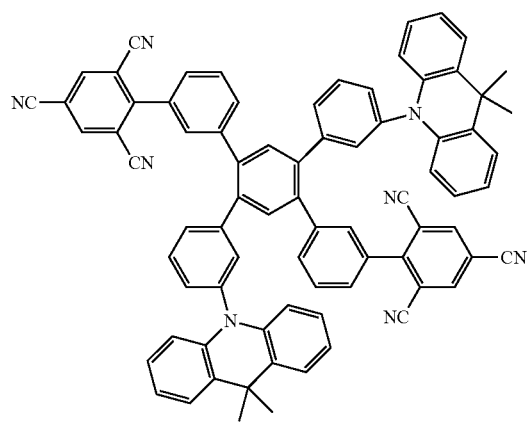
P31
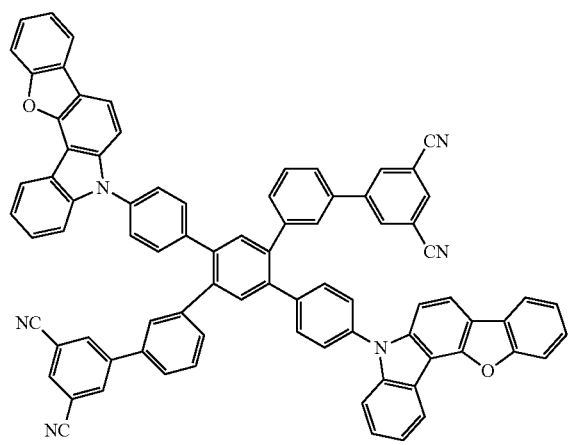
P32
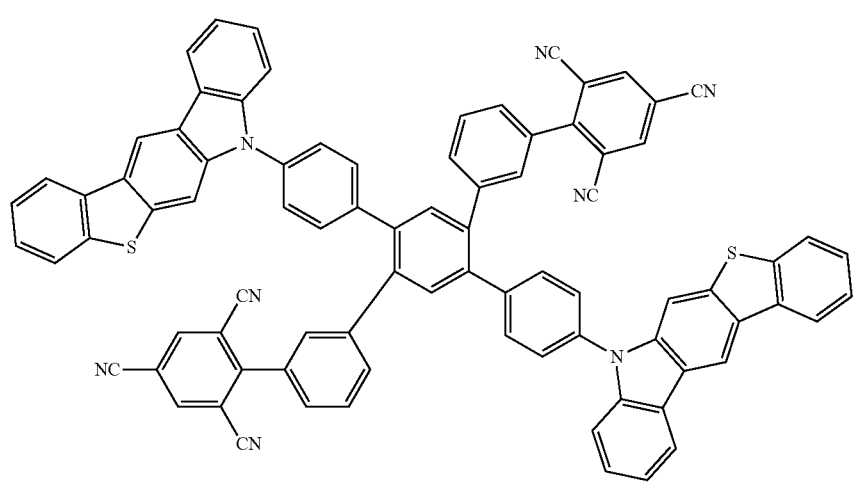

-continued
P33
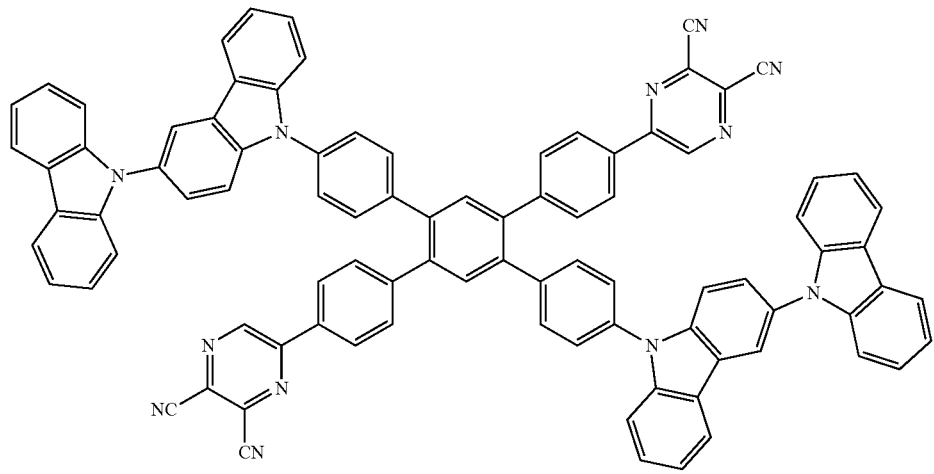
P34
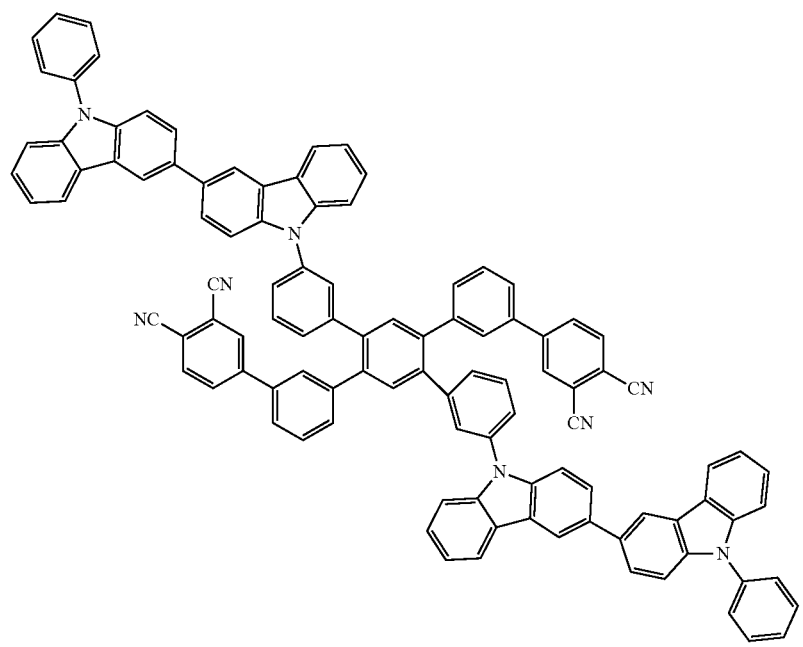
P35
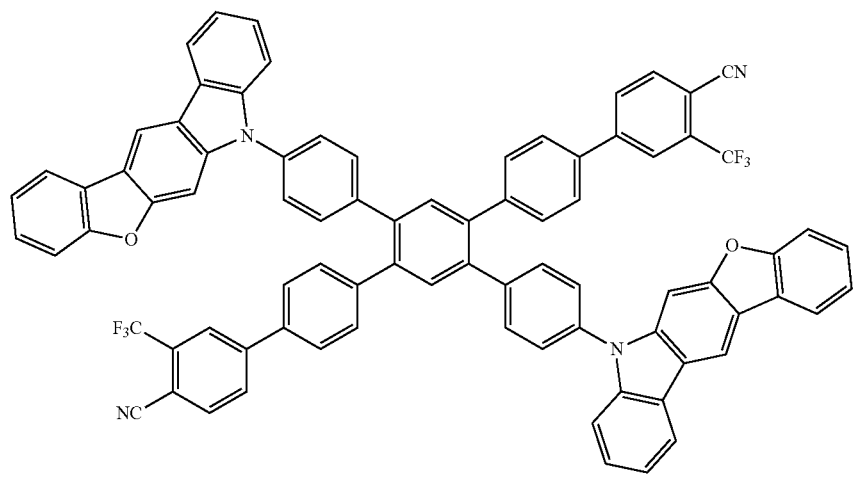

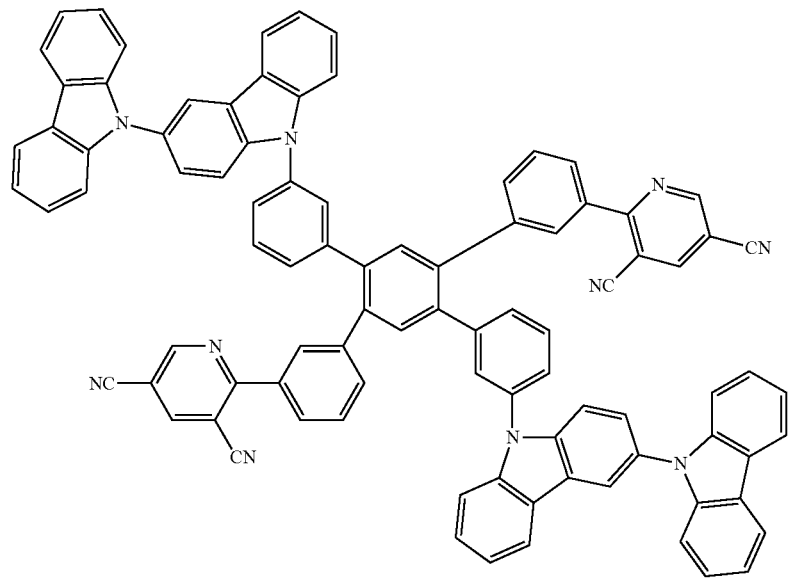
P36
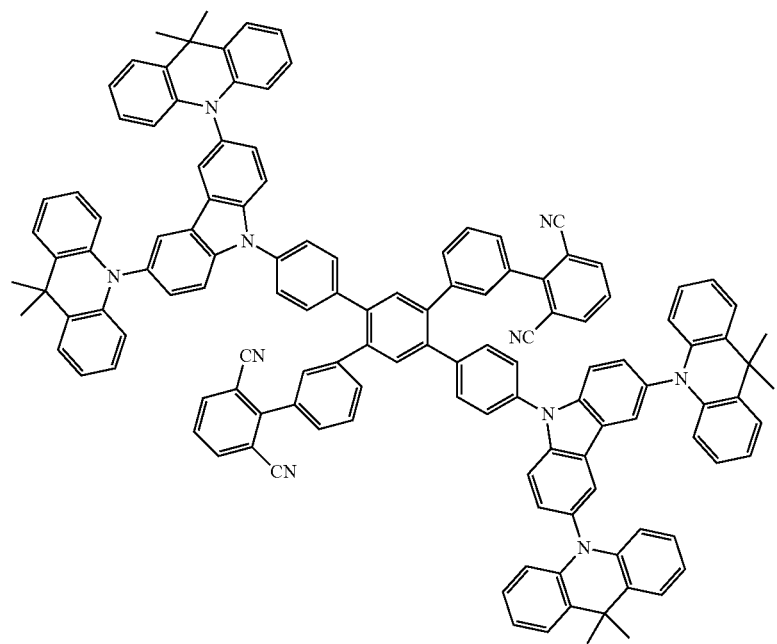
P37

P38
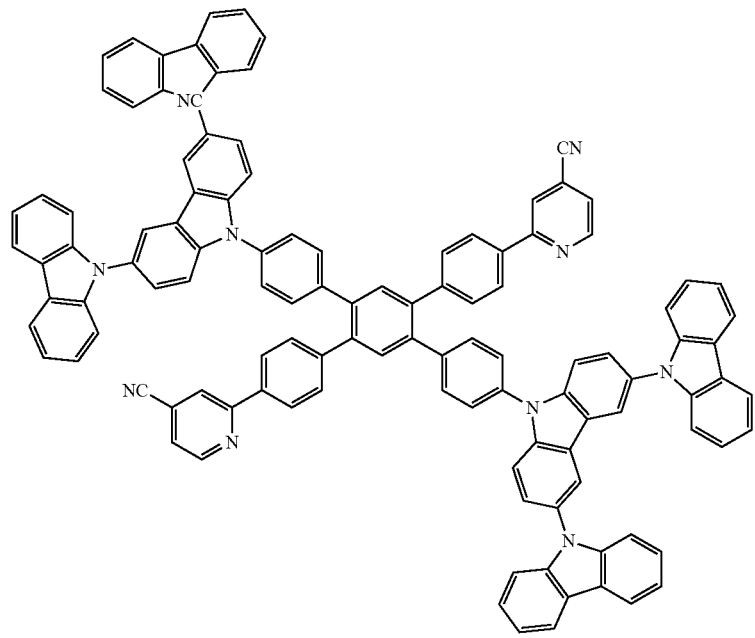
P39
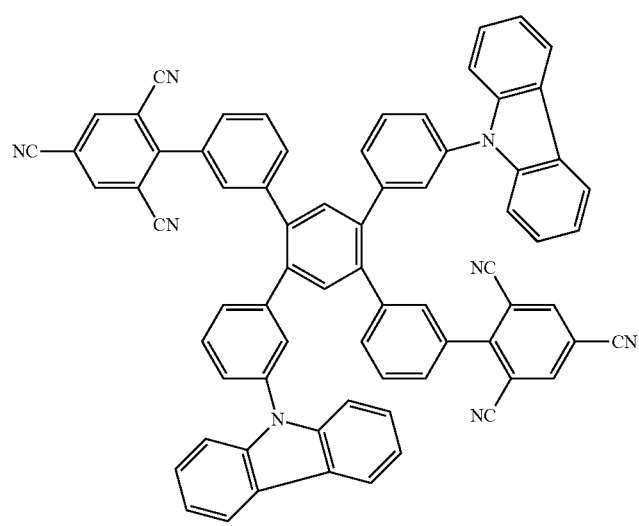

-continued
P40
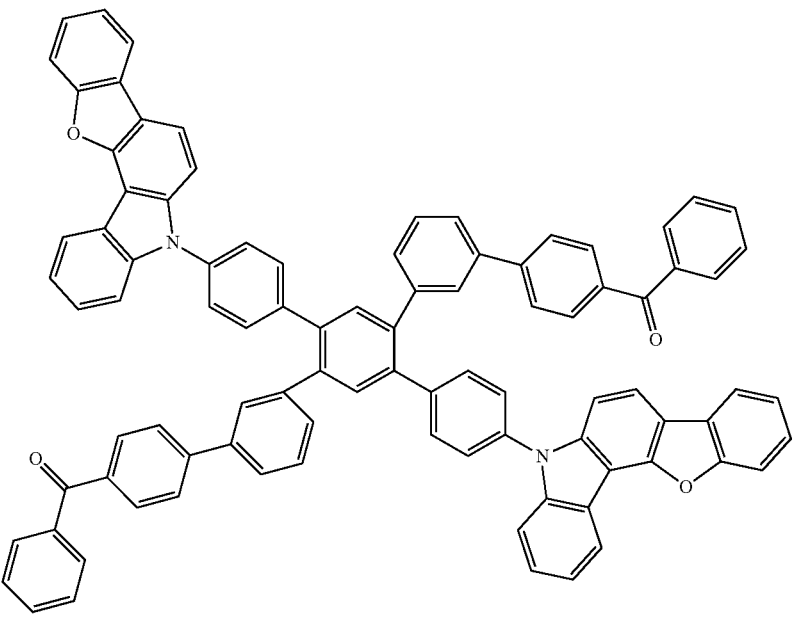
P41
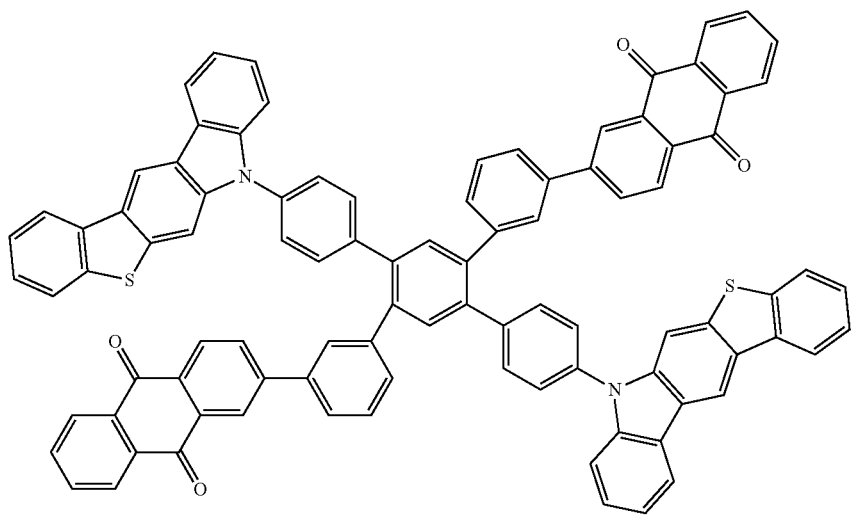
P42
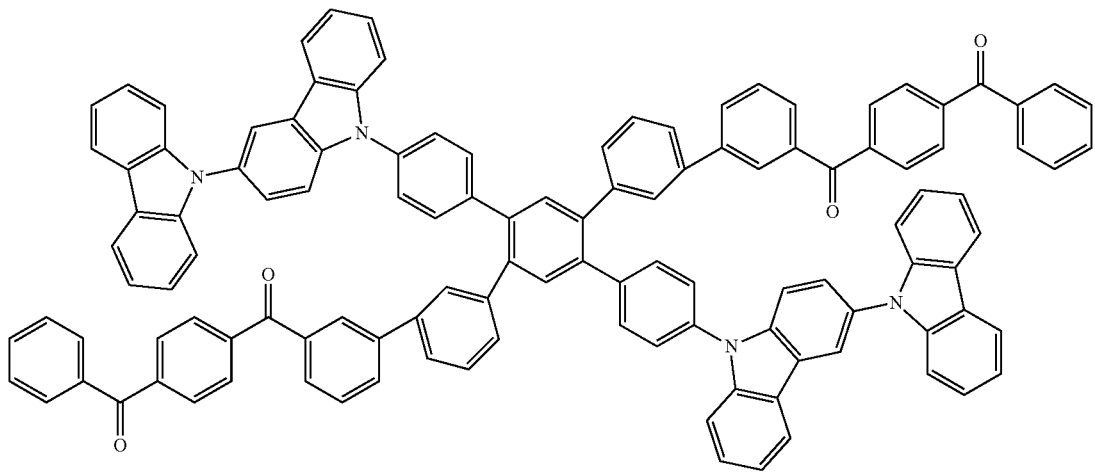

P43
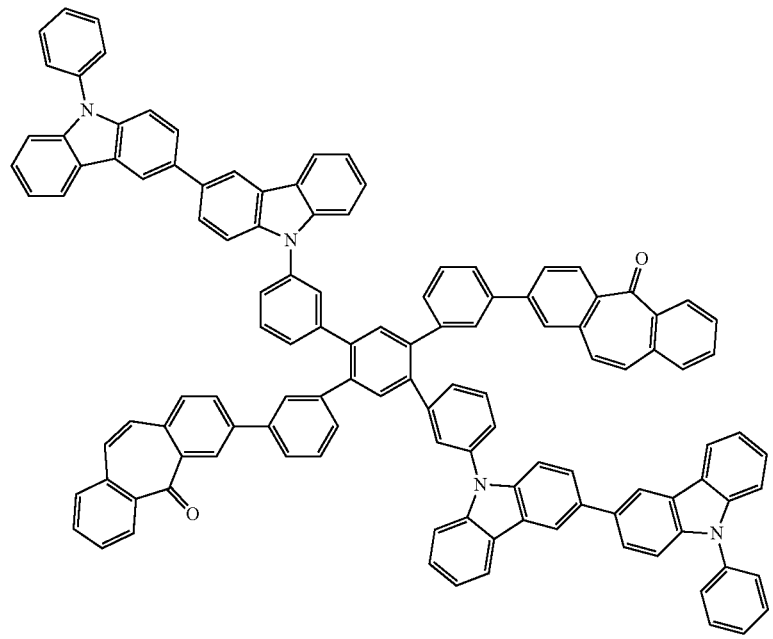
P44
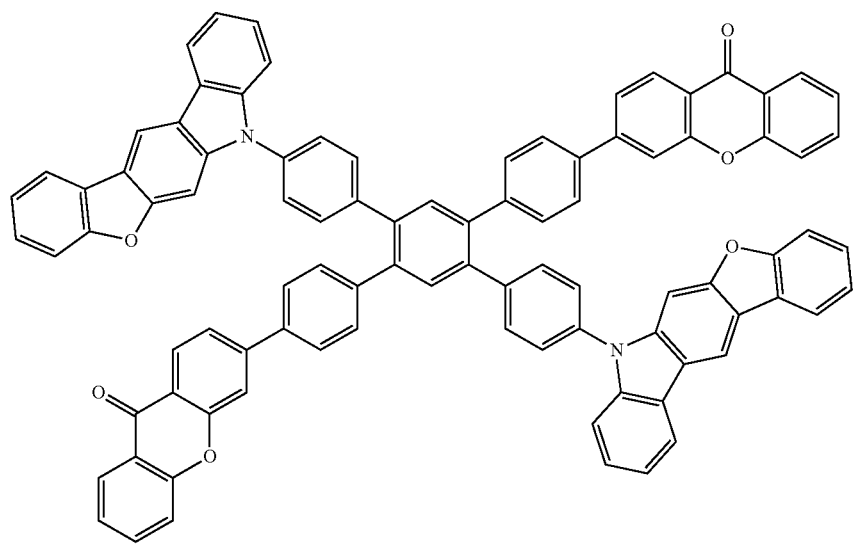

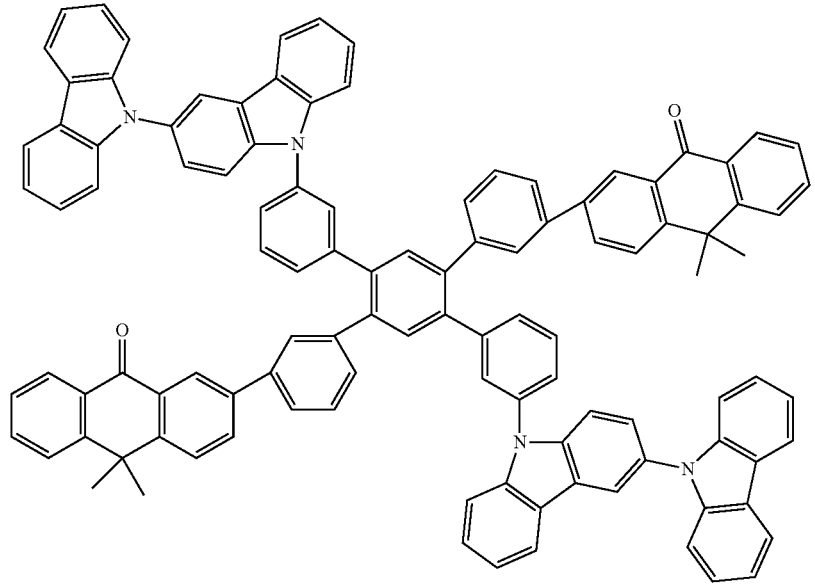
P45
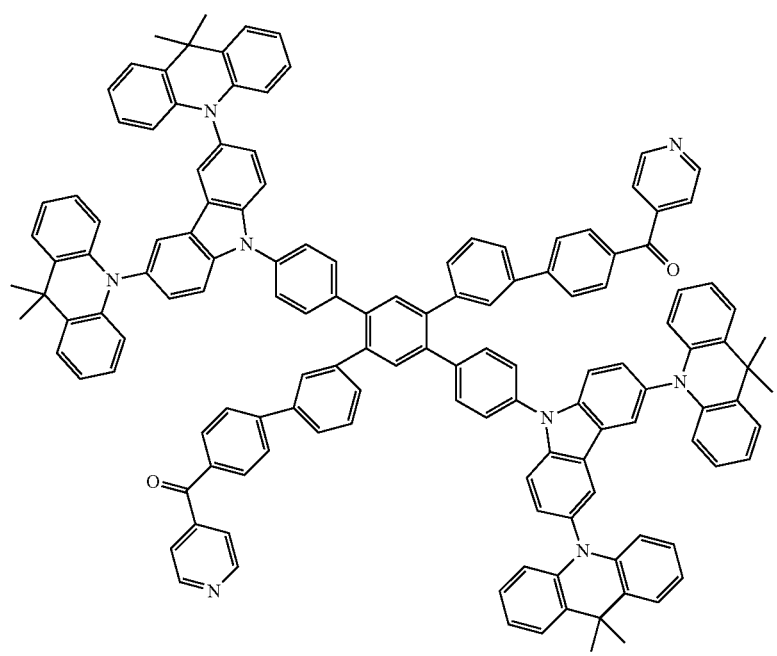
P46

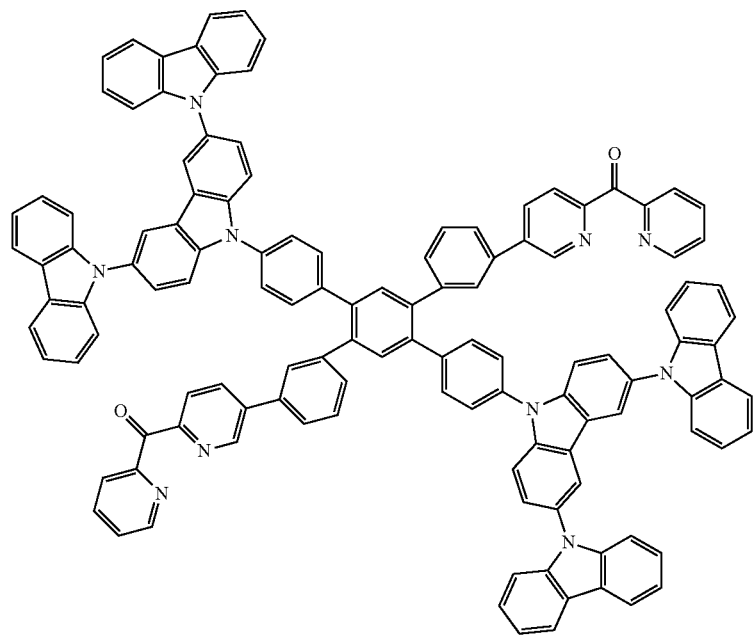
P47
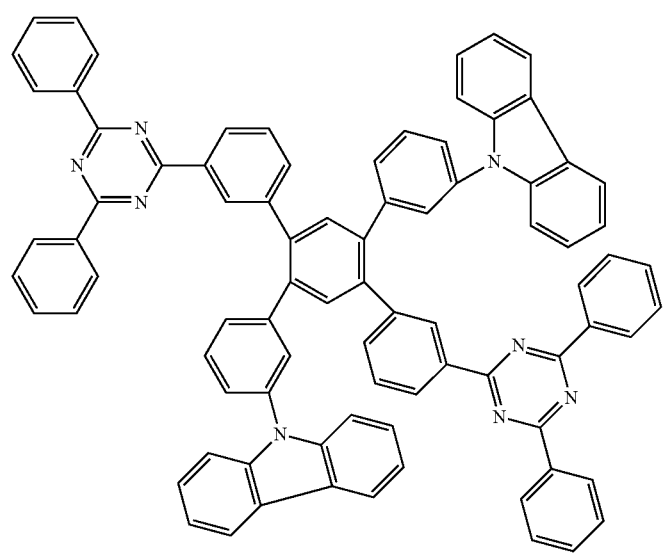
P48

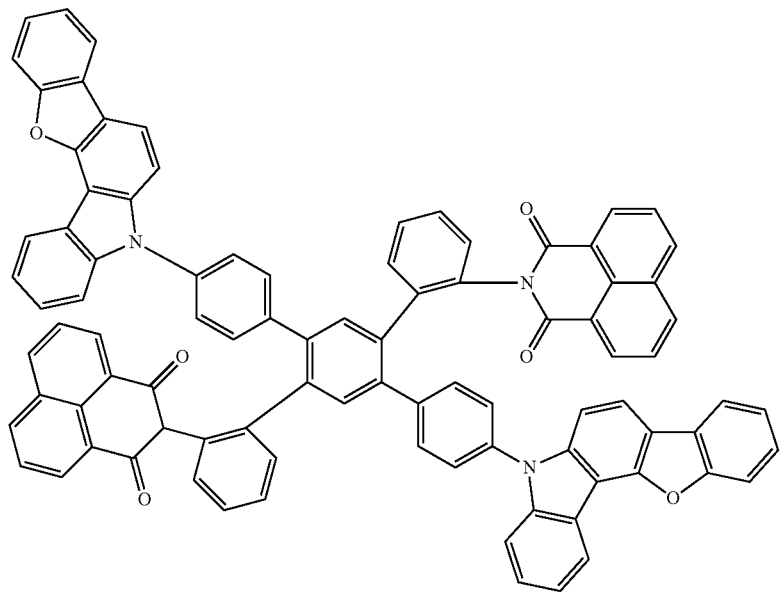
P49
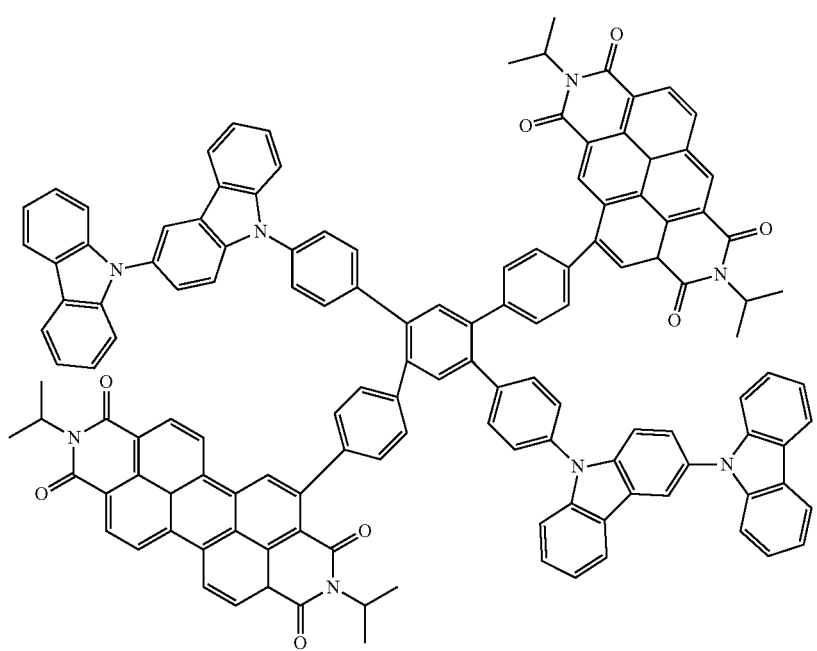
P50

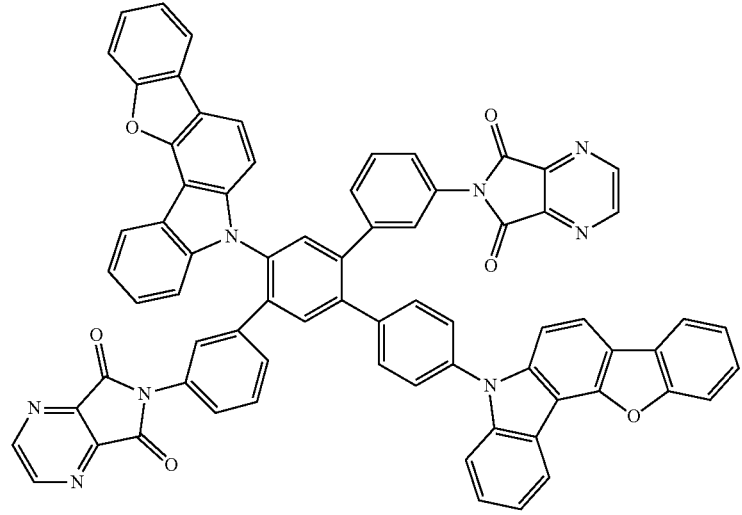
P51
P52

-continued
P53
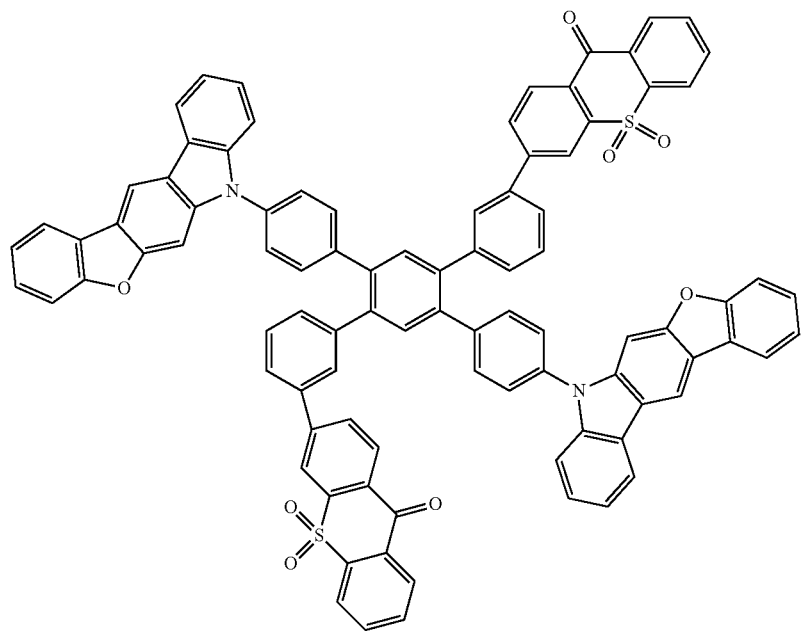
P54
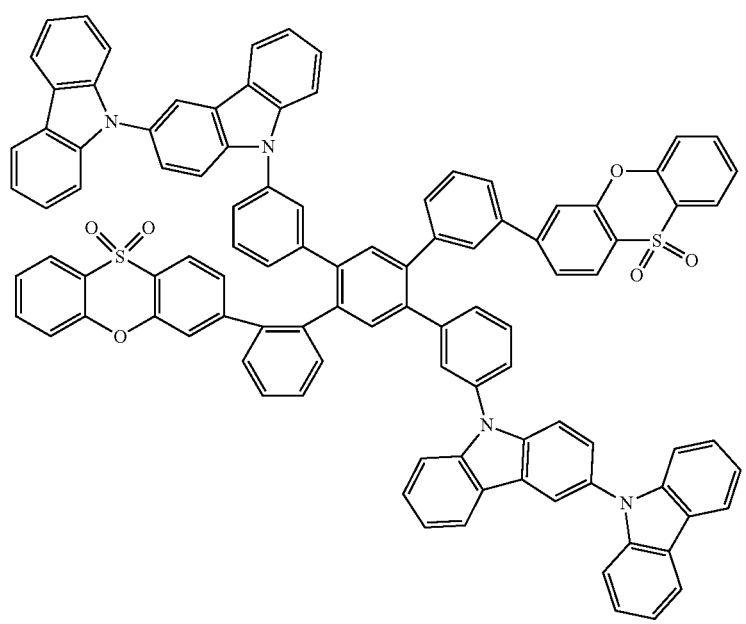

P55
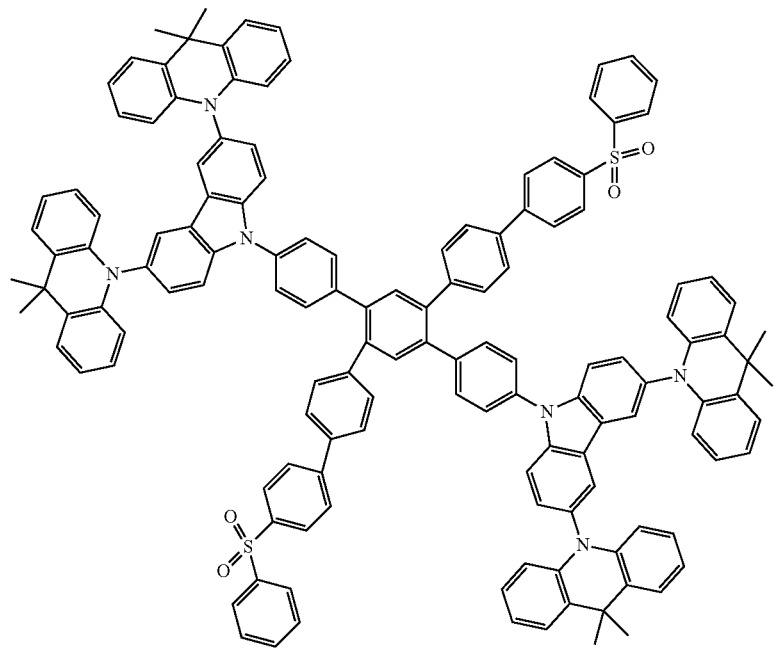
P56
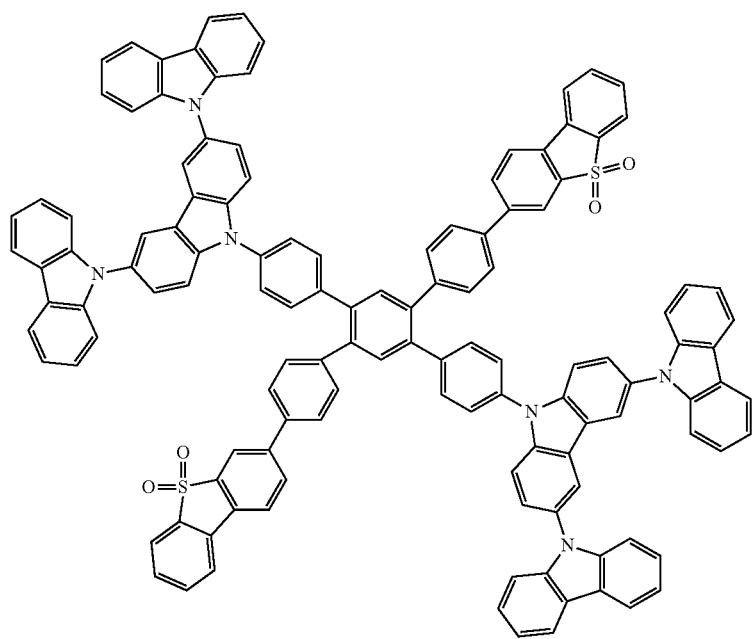

P57
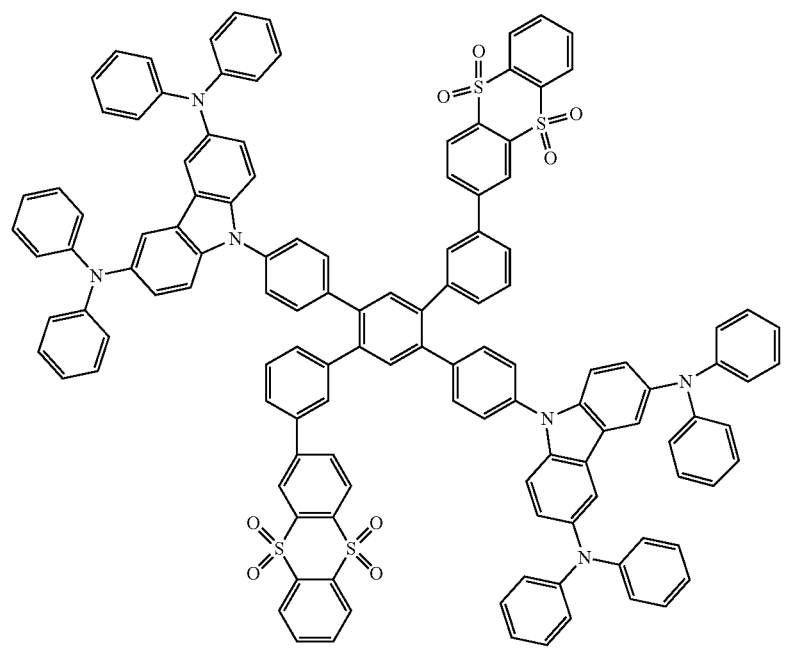
P58
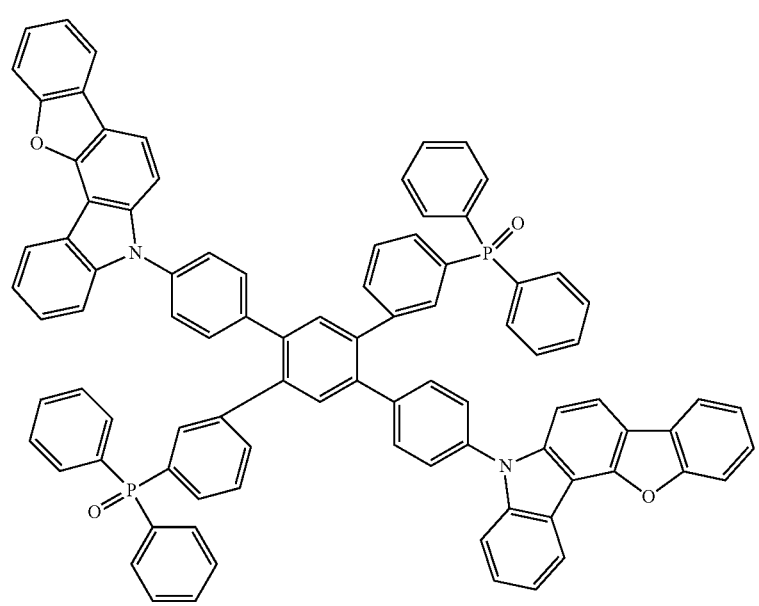

-continued
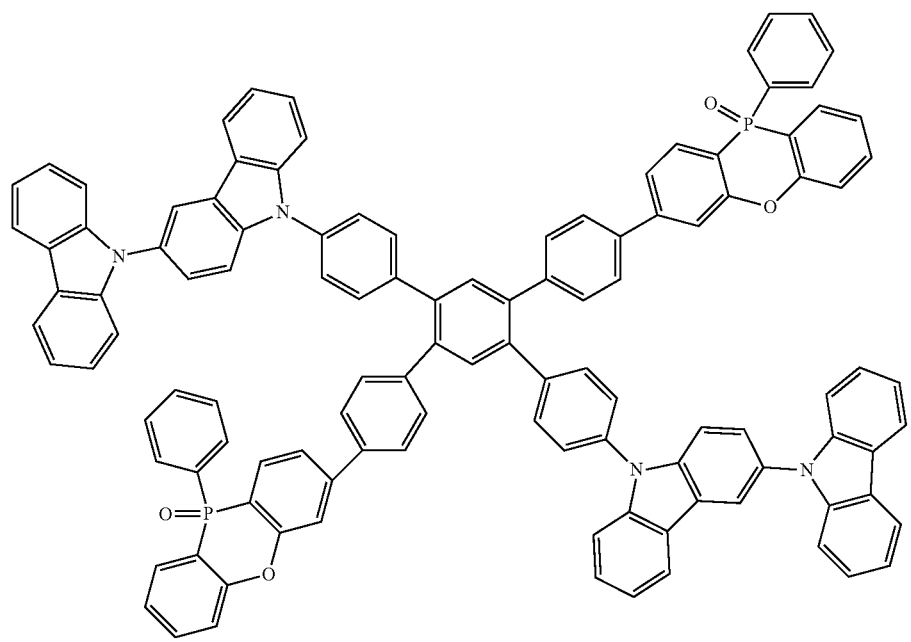
P59
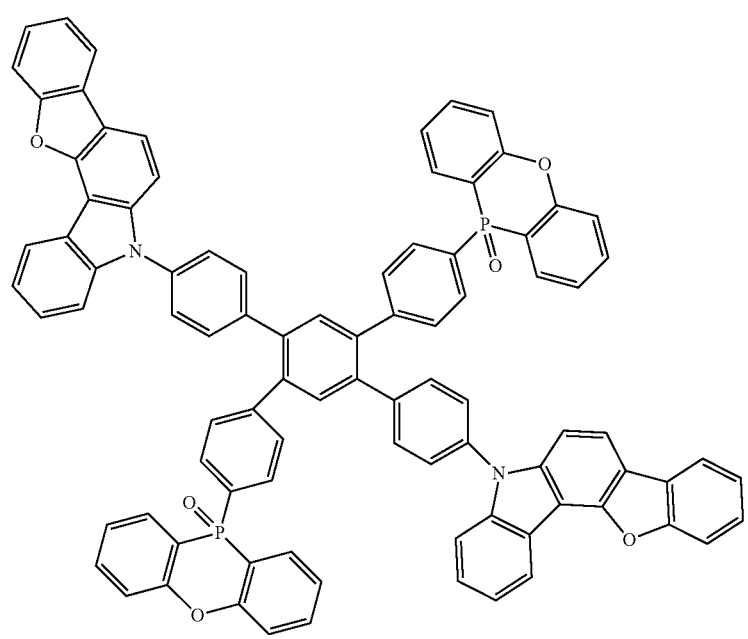
P60

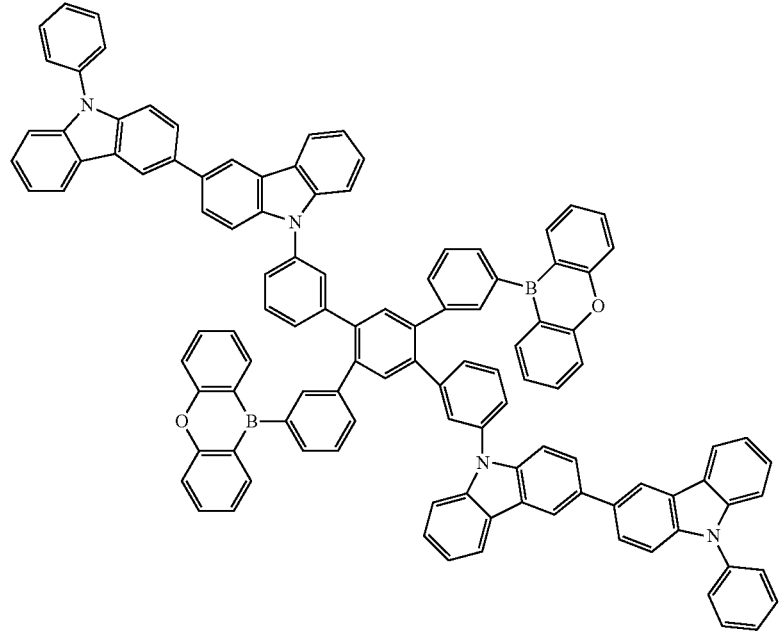
P61
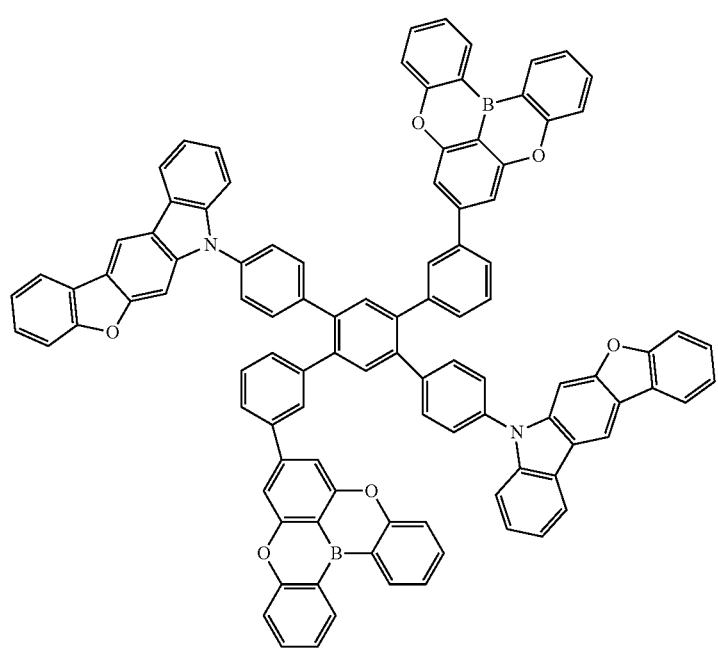
P62

-continued
P63
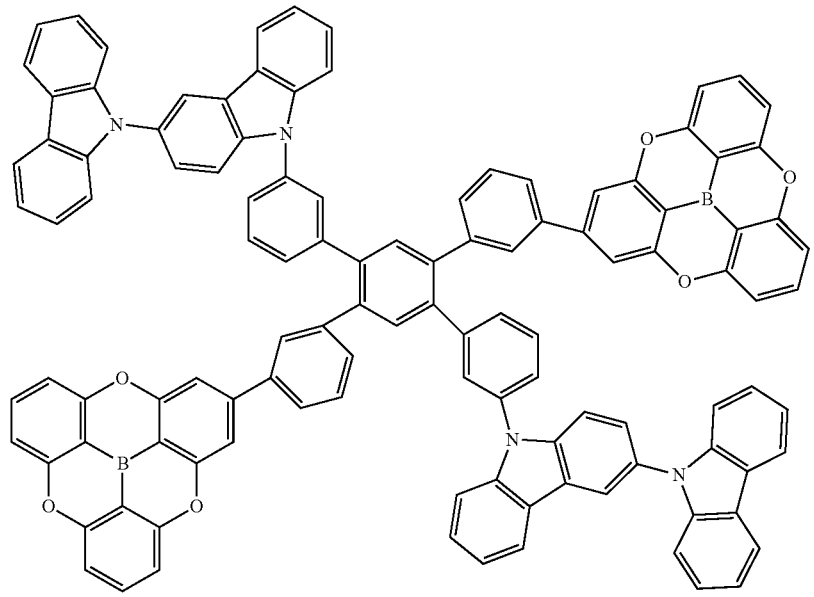
P64
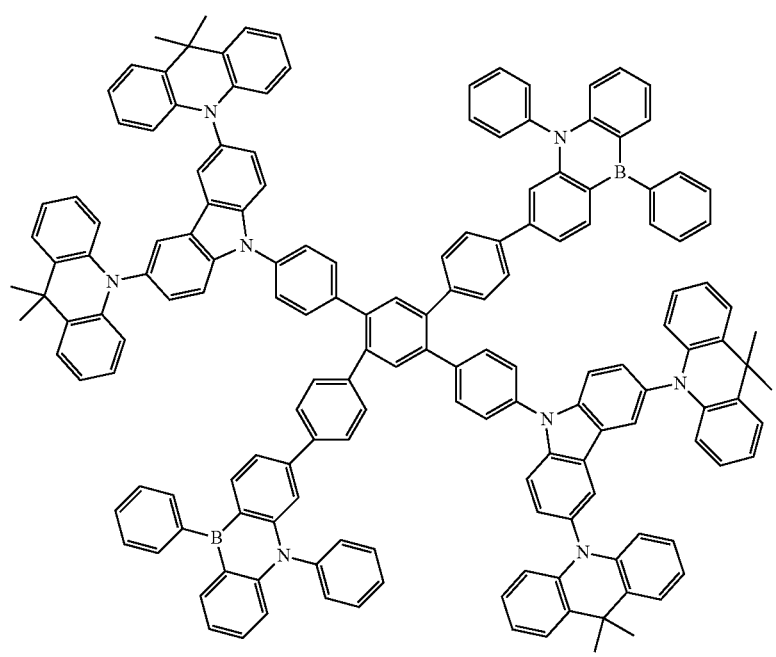

P65
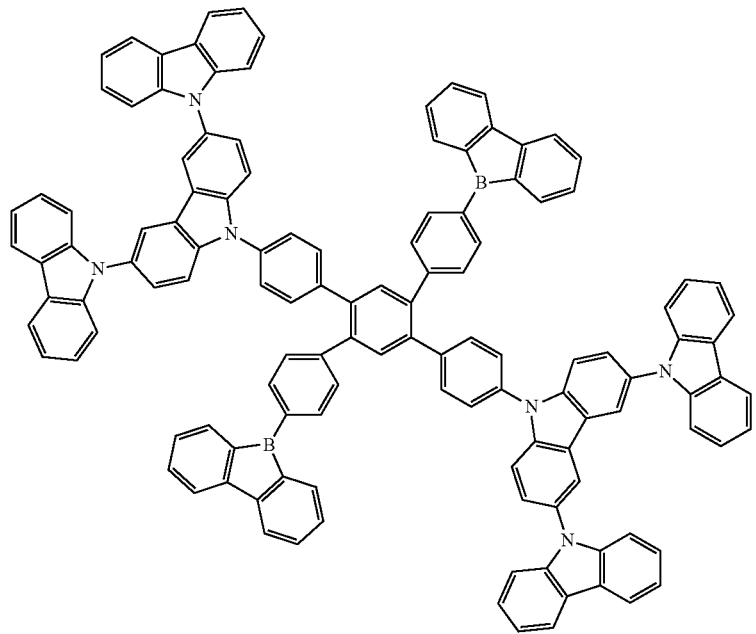
P66
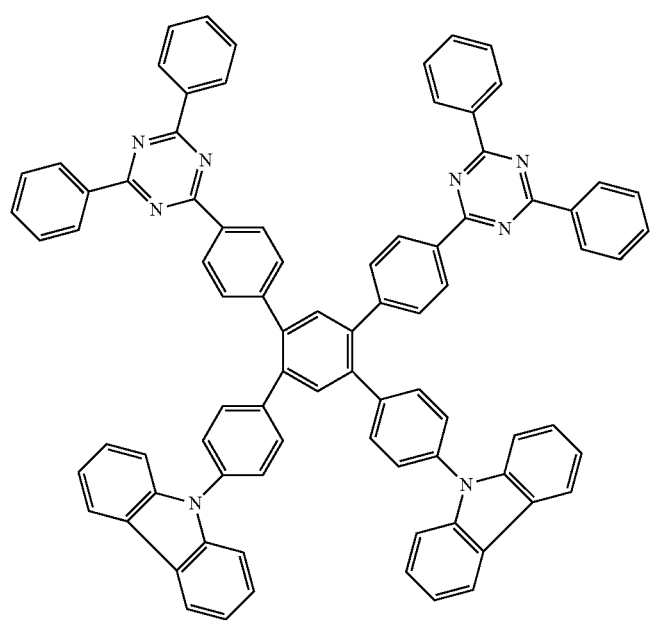

-continued
P67
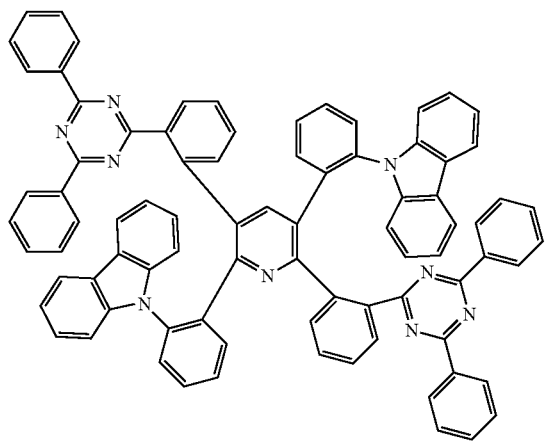
P68
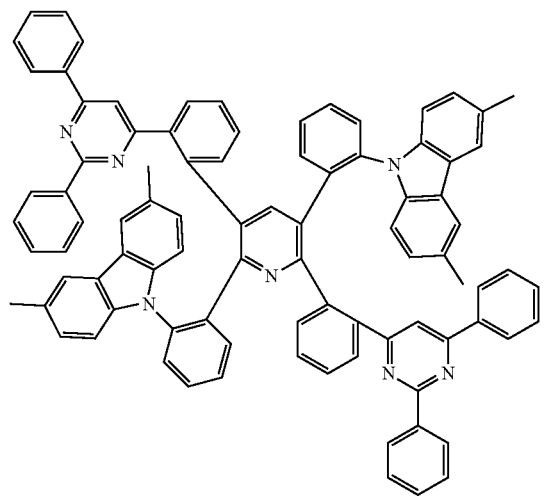
P69
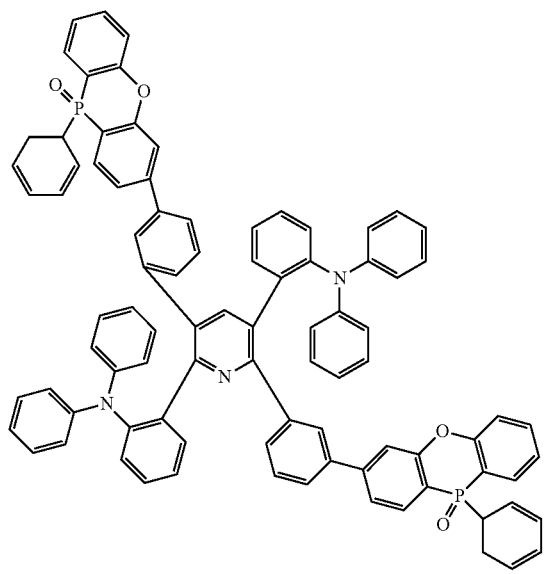
P70
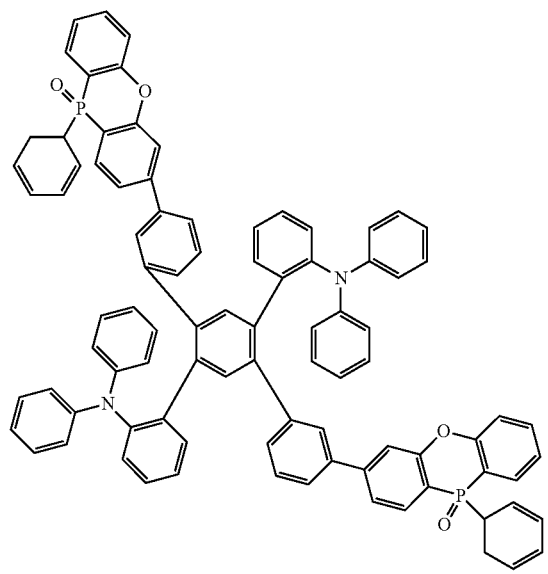
P71
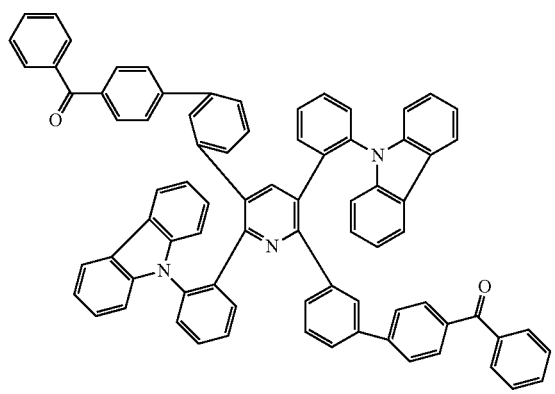
P72
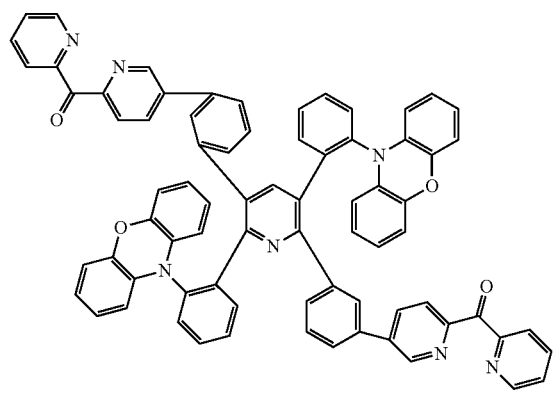

P73
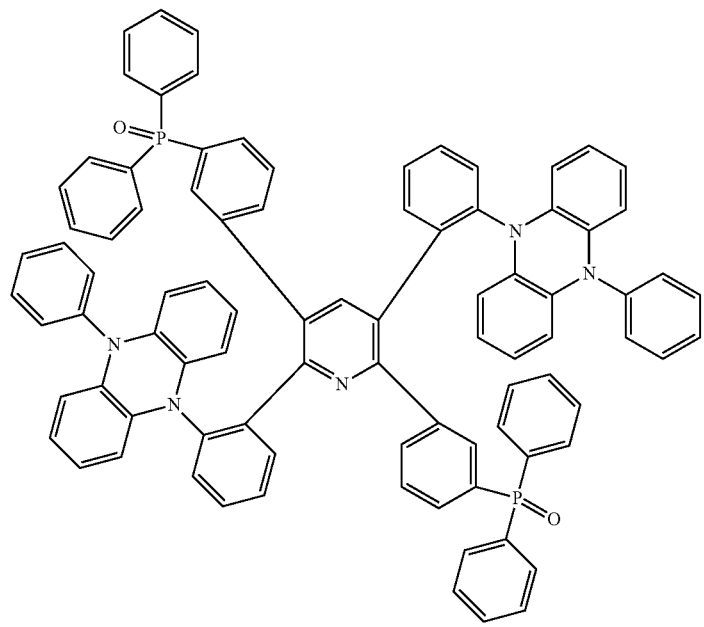
P74
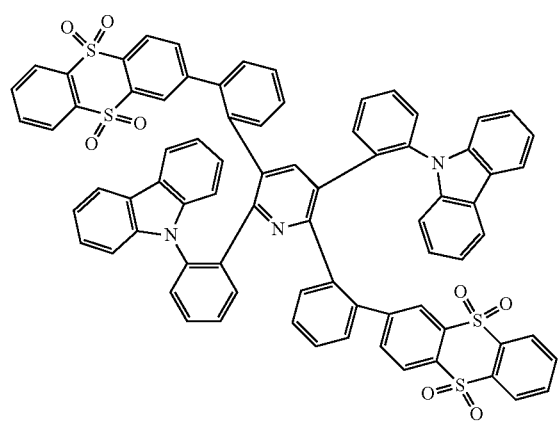
P75
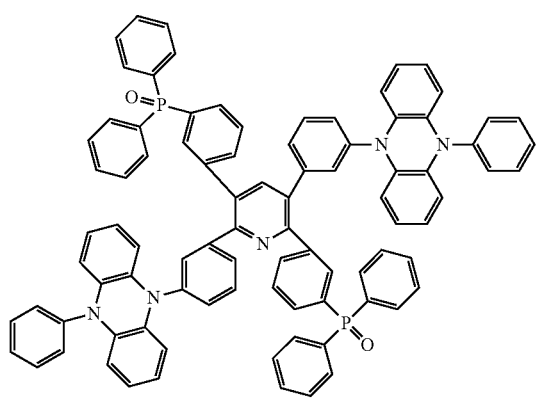

-continued
P76
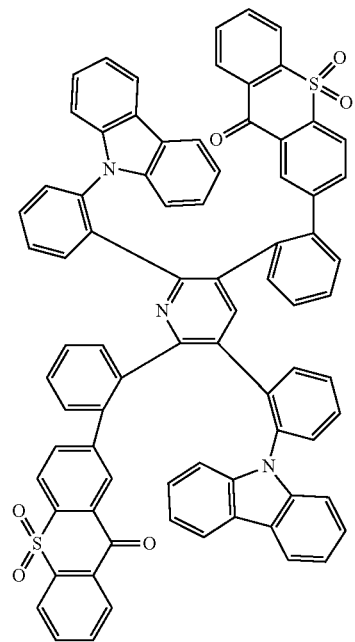
P77
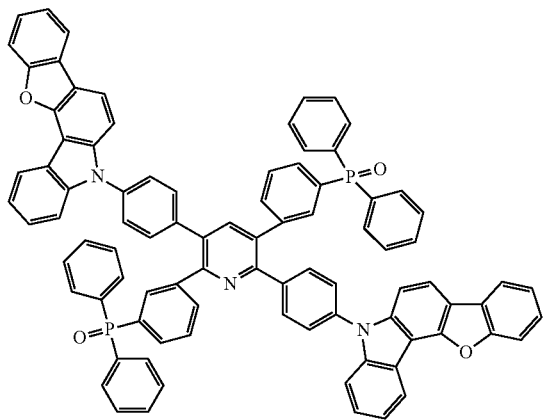
P78
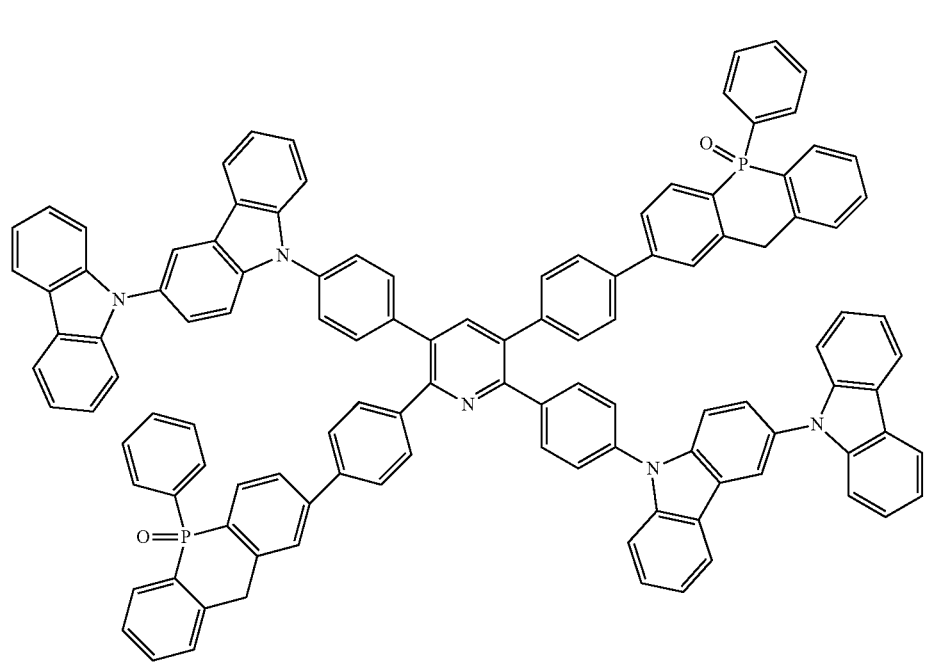

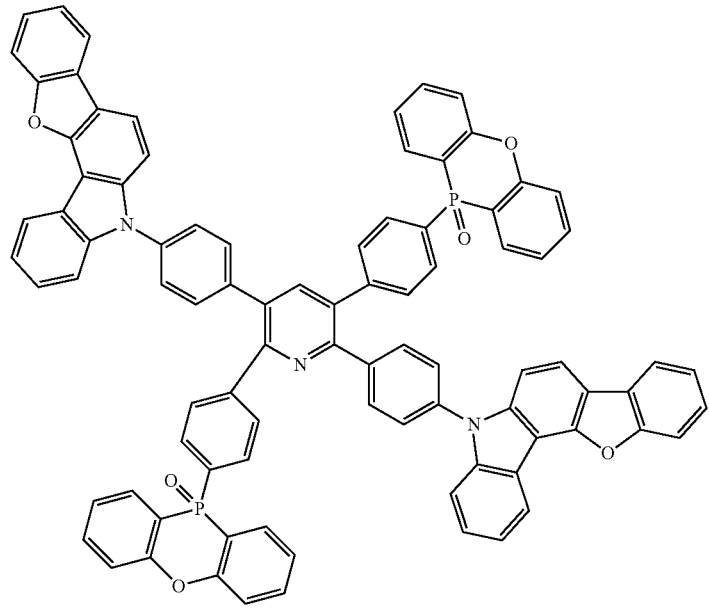
P79
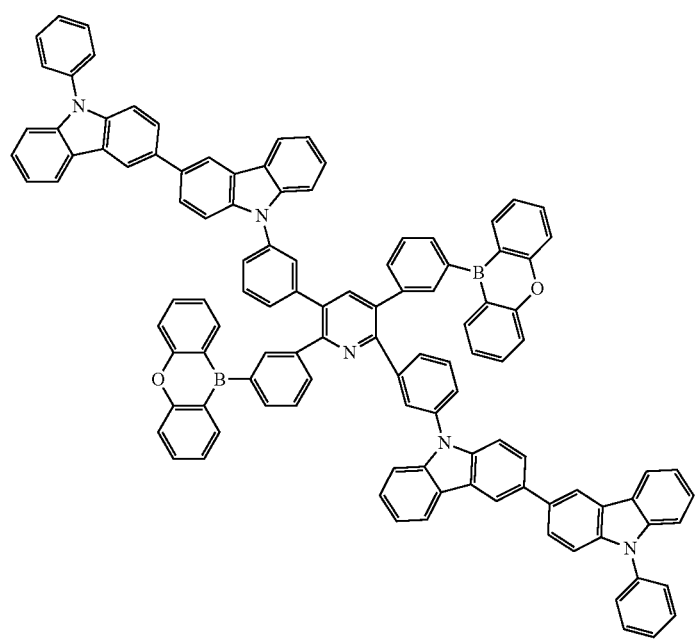
P80

P81
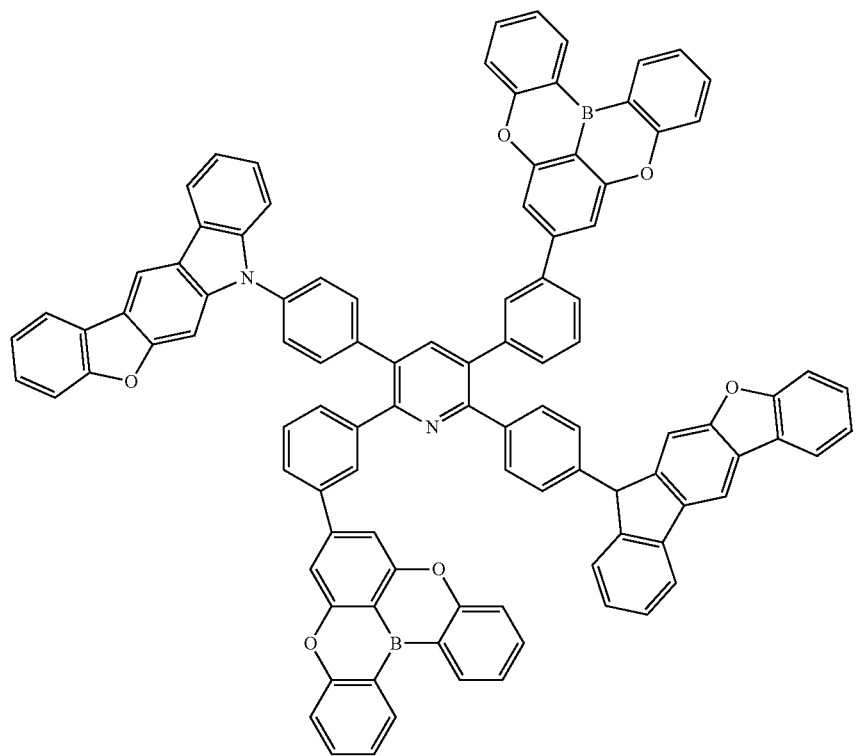
P82
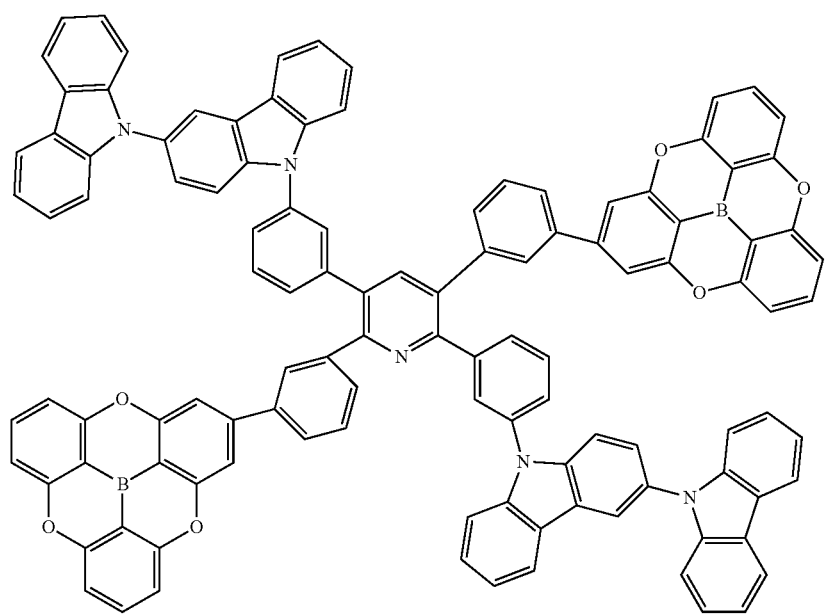

P83
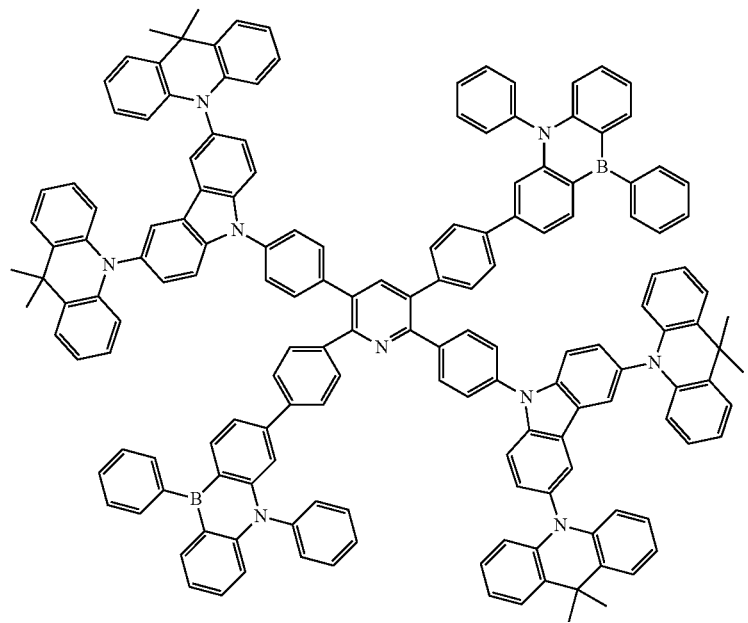
P84
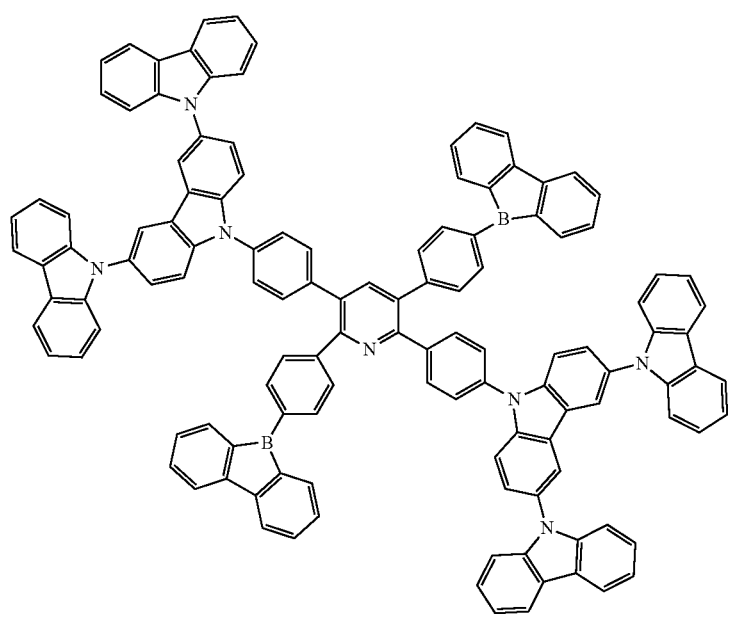

P85
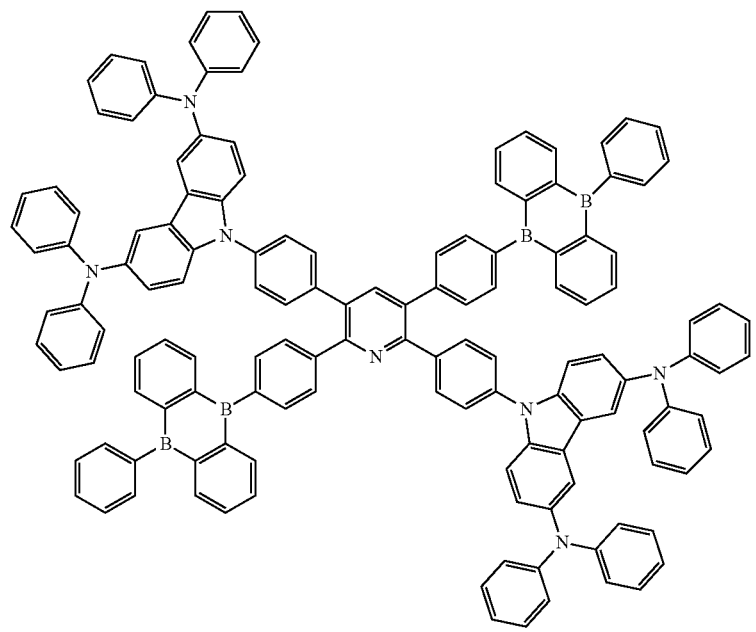
P86
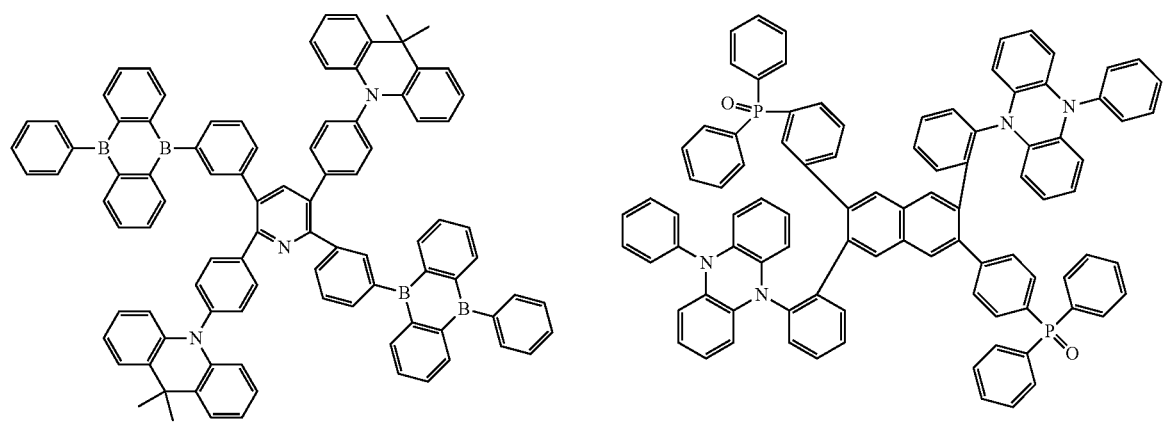
P87
P88
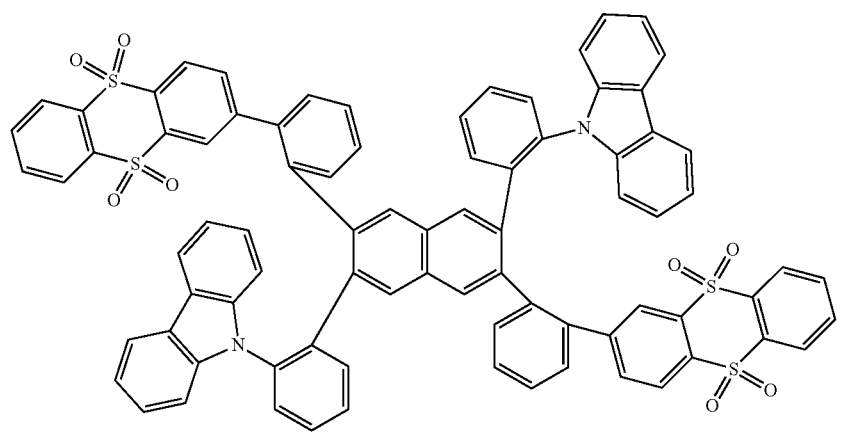

-continued
P89
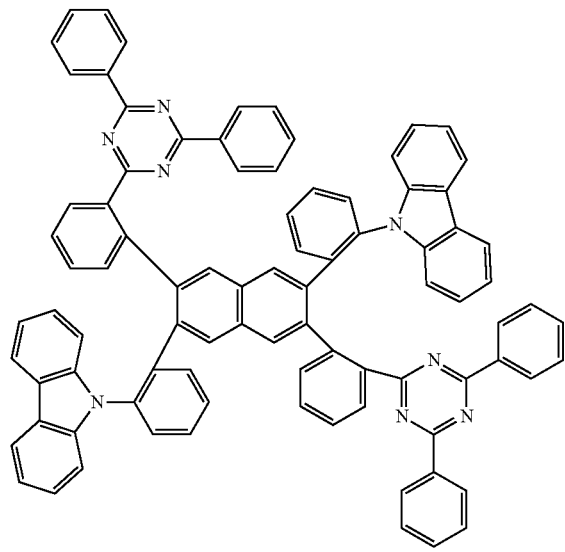
P90
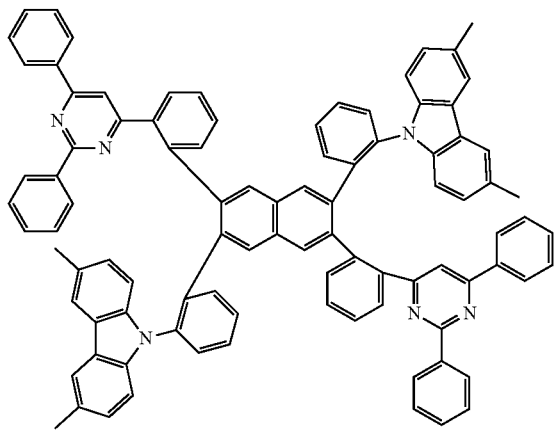
P91
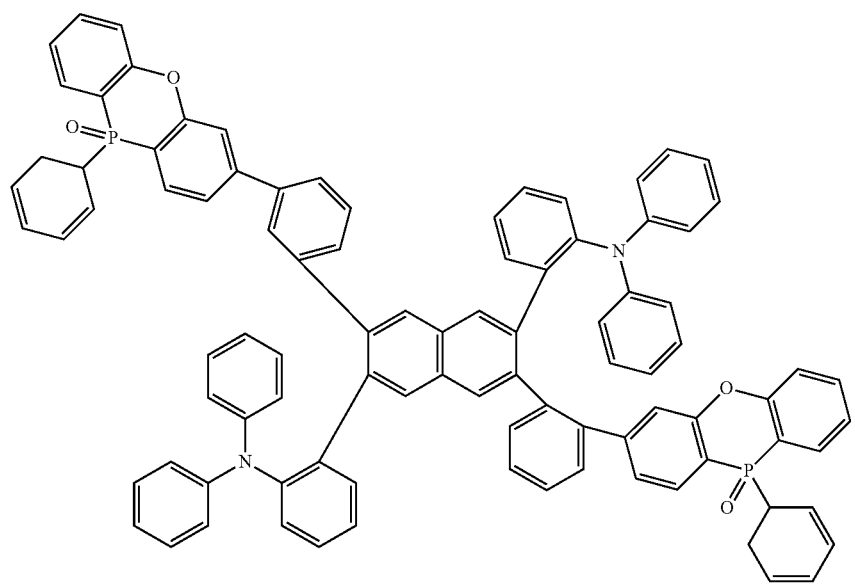
P92
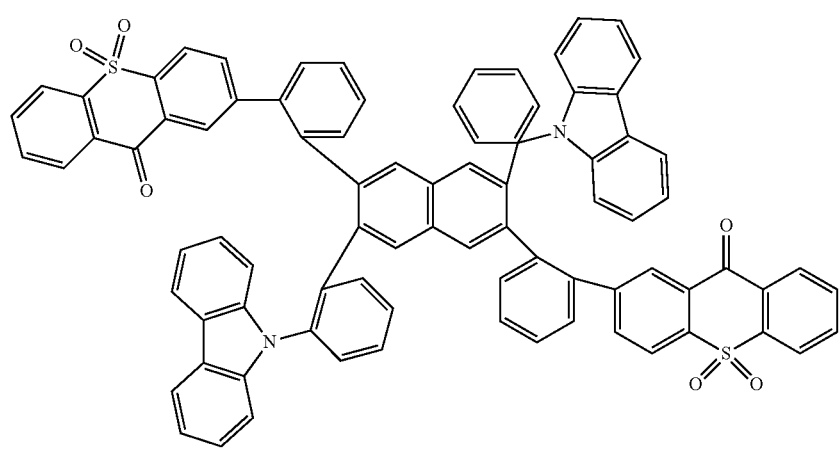

-continued
P93
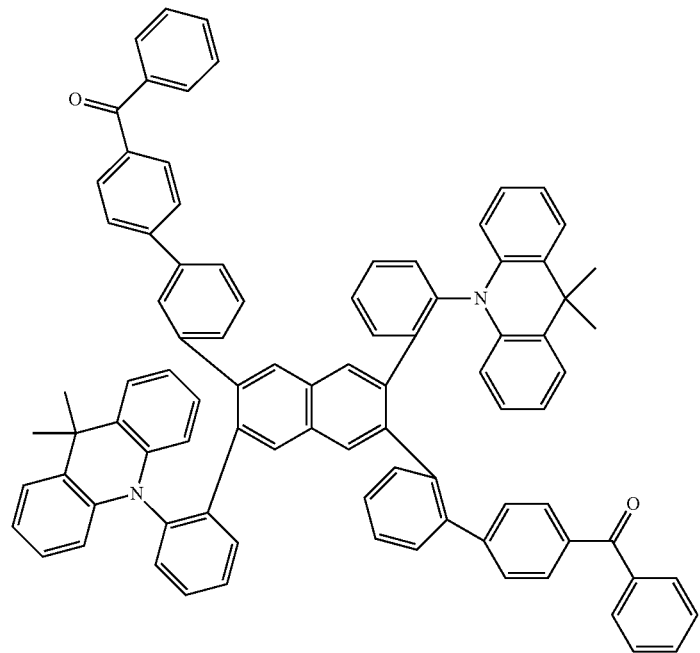
P94
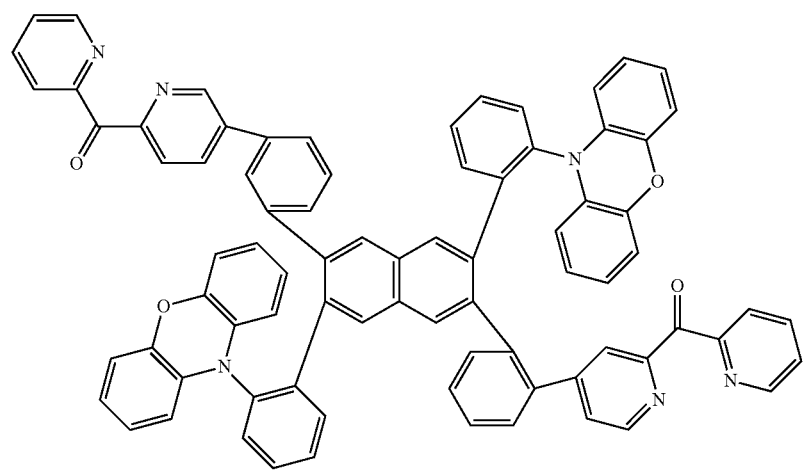

-continued
P95
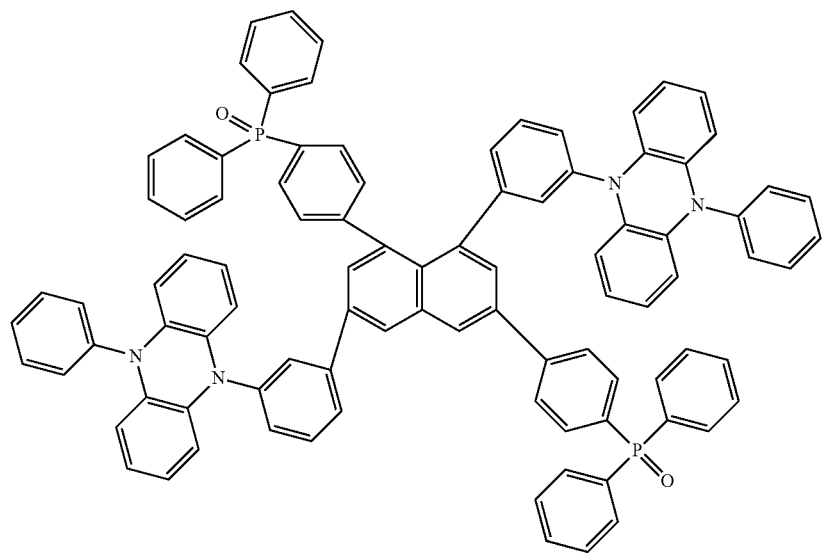
P96
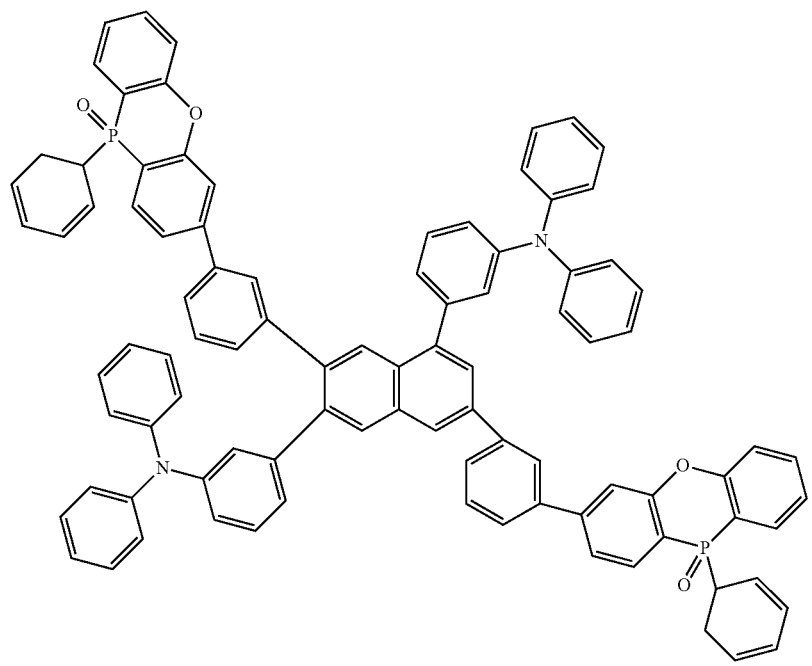

P97
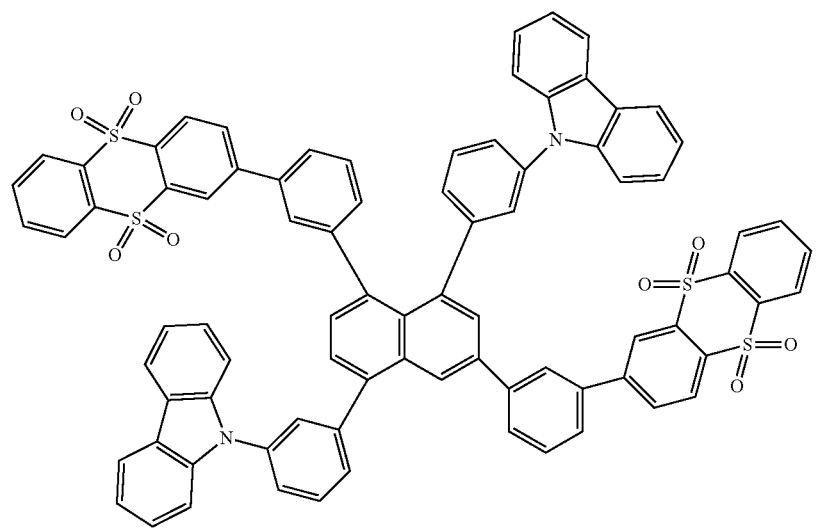
P98
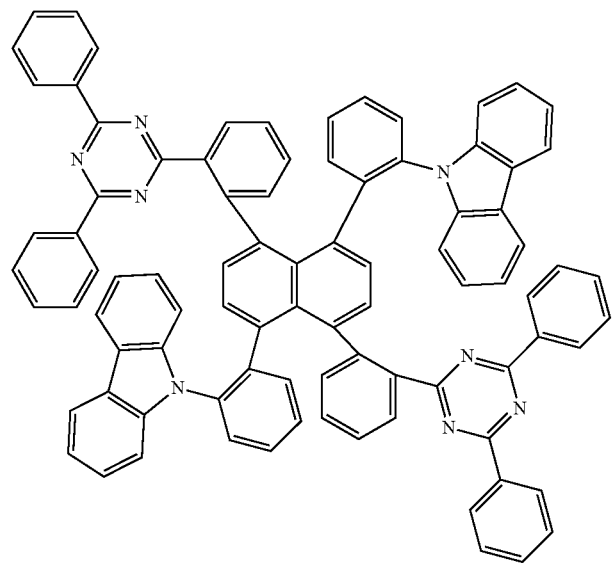

P99
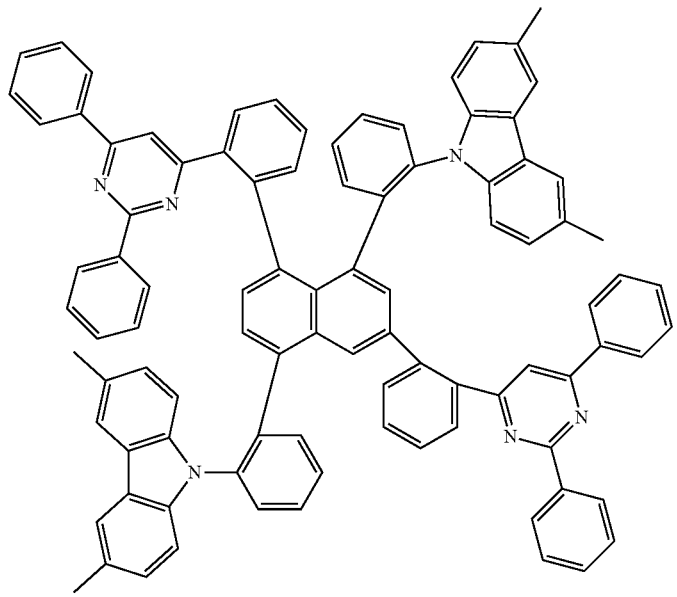
P100
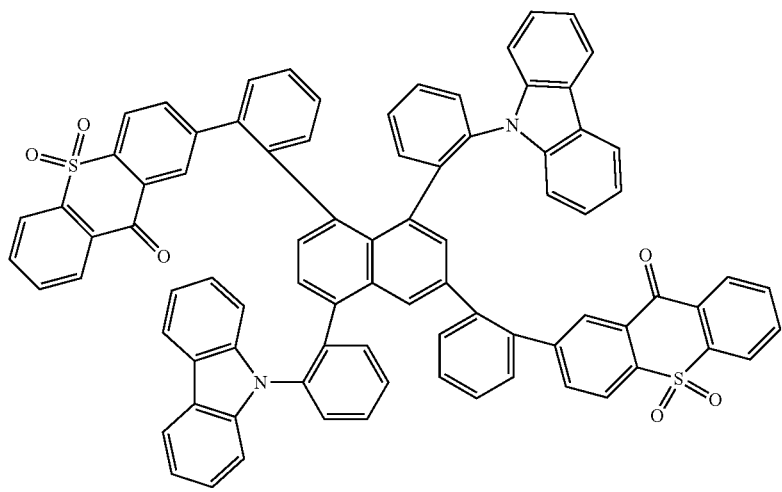
P101
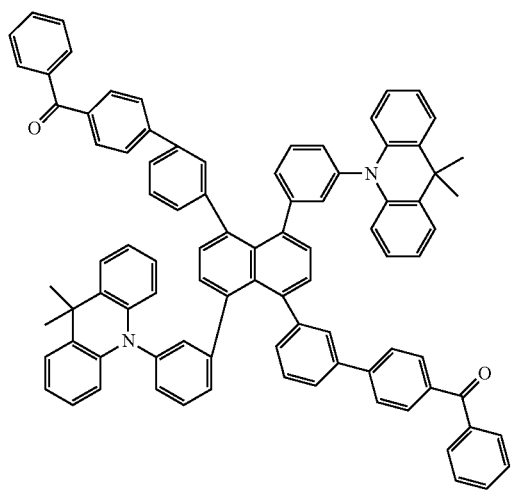
P102
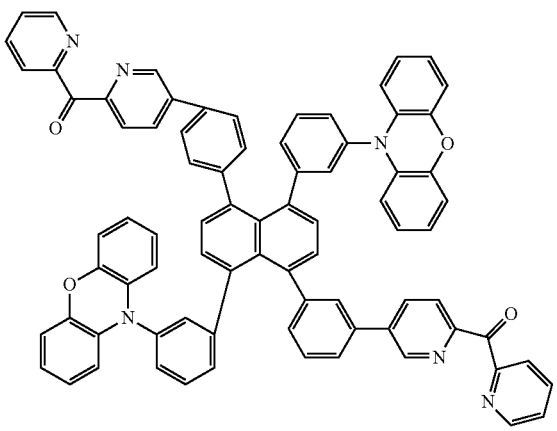

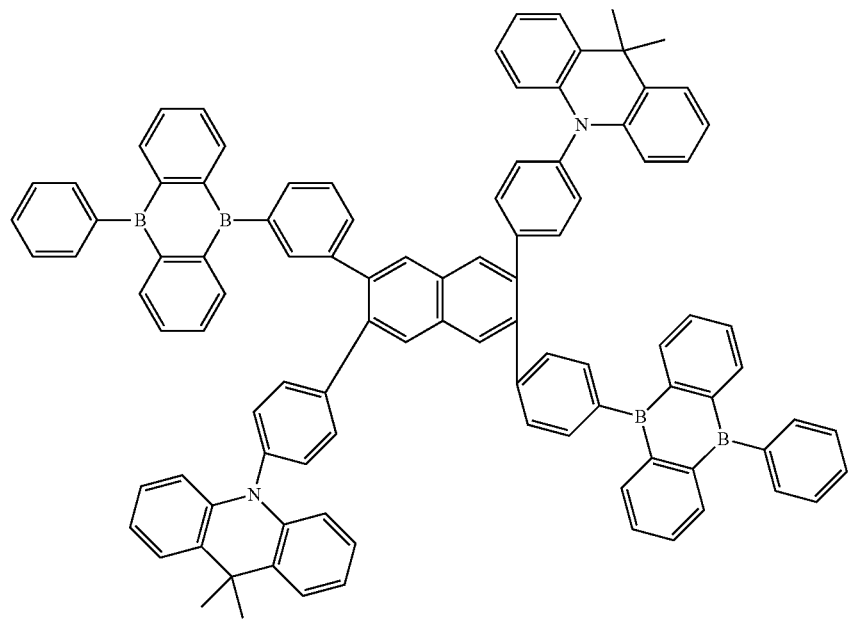

P103

According to one embodiment of the compound of the present disclosure, an energy level difference between a lowest singlet energy level S1 and a lowest triplet energy level T1 of the compound satisfies: $\Delta E_{ST}=E_{S1}-E_{T1} \leq 0.30$ eV.

The compound of the present disclosure has TADF properties, and can be used as a host or guest material for an OLED light-emitting layer.

The present disclosure also provides methods for preparing representative compounds P7, P39, P66, P71, and P103. In the following synthesis examples, the used intermediates S1, S2, S5, S7, S8, S11, 512, 514, 518, 519, 521, S22, S23, S25 and S26 are all commercially available.

Synthesis of Compound 7

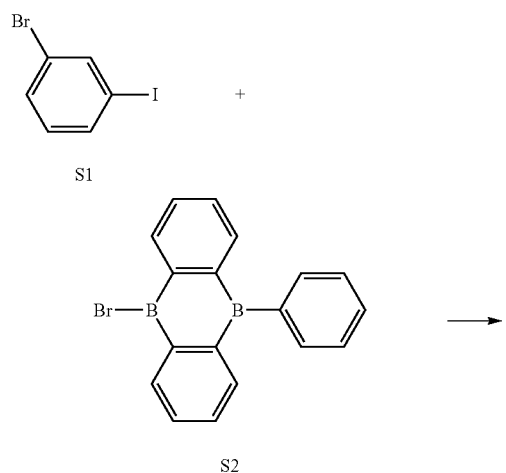

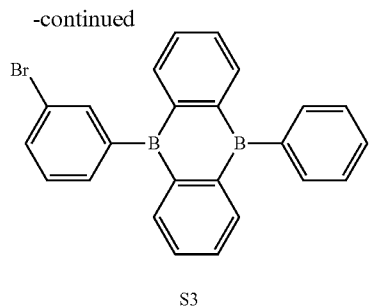

S3

At −78° C., S1 (1.8 mmol) was dissolved in diethyl ether (100 mL), and an n-hexane solution of n-BuLi (1.95 mmol) was added dropwise to the solution. The reaction solution was continuously stirred for 2 h, slowly warmed to room temperature, and stirred at room temperature for 1 h. The reaction solution was again cooled to −78° C., and 45 mL toluene solution of S2 (2.2 mmol) was added dropwise with stirring. The reaction solution was slowly warmed to room temperature and stirred overnight. All solvents were removed by distillation under reduced pressure, and the crude product was collected. The crude product was respectively washed with methanol (3×40 mL) and pentane (3×40 mL), and then the crude product was collected again. The crude product was purified by silica gel chromatography column, using hexane: chloroform (6:1) as eluent, to obtain S3 (0.97 mmol, 54%). MALDI-TOF MS: $C_{24}H_{17}B_2Br$, m/z calculated: 406.1; measured: 406.3.

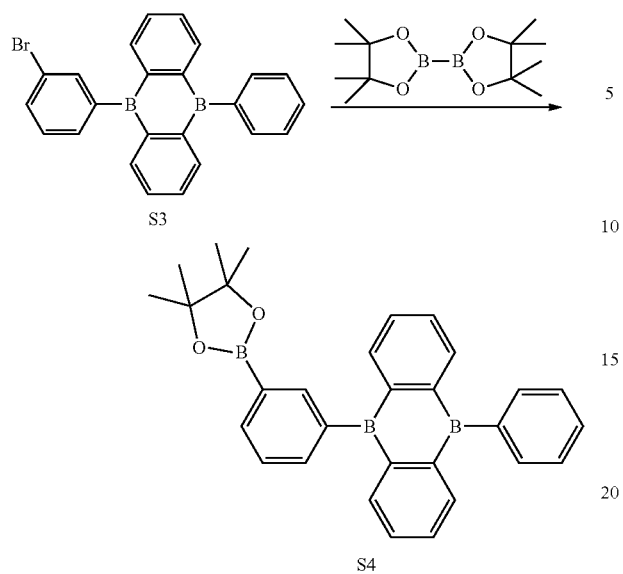

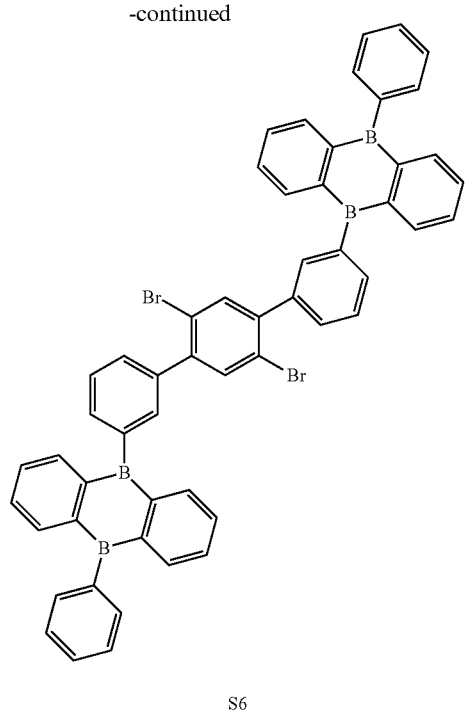

In a 100 ml three-necked flask, S3 (1.5 mmol), bis(pinacolato)diboron (1.8 mmol), (1,1'-bis(diphenylphosphino)ferrocene) dichloropalladium (II) (0.04 mmol), and potassium acetate (10 mmol) were first added separately, degassing and nitrogen replacement were repeated three times while stirring, and 6 mL tetrahydrofuran was added through a syringe. Under stirring at a certain rotation speed, the obtained mixed solution reactant was heated to reflux at a reaction temperature of 80° C. for 5 h; after the reaction was completed, it was cooled to room temperature, added with 5 ml water, and extracted with diethyl ether. The obtained organic phase was dried with anhydrous sodium sulfate, evaporated to remove the solvent, and purified by using column chromatography to obtain an intermediate S4 (1.2 mmol, 80%).

MALDI-TOF MS: $C_{30}H_{29}B_3O_2$, m/z calculated: 454.2; measured: 454.5.

Under nitrogen protection, compound S5 (4.5 mmol), compound S4 (9.6 mmol), $[Pd_2(dba)_3] \cdot CHCl_3$ (0.18 mmol), and $HP(tBu)_3 \cdot BF_4$ (0.36 mmol) were weighed and added to a 250 mL two-necked flask. 80 mL toluene (previously treated with $N_2$ for 15 min for removing oxygen) was injected to the two-necked flask, then 8 mL aqueous solution (1M) of $K_2CO_3$ (previously treated with $N_2$ for 15 min to remove oxygen) was added dropwise, and stirred at room temperature overnight. After the reaction was finished, 20 mL deionized water was added, and then a few drops of 2M HCl were added. The solution was extracted with dichloromethane, and the organic phase was collected and dried with anhydrous $Na_2SO_4$. The dried solution was filtered, and the solvent was removed by a rotary evaporator to obtain a crude product. The crude product was purified by silica gel chromatography column to finally obtain a solid S6 (3.4 mmol, 75%).

MALDI-TOF MS: $C_{54}H_{36}B_4Br_2$, m/z calculated: 887.9; measured: 888.2.

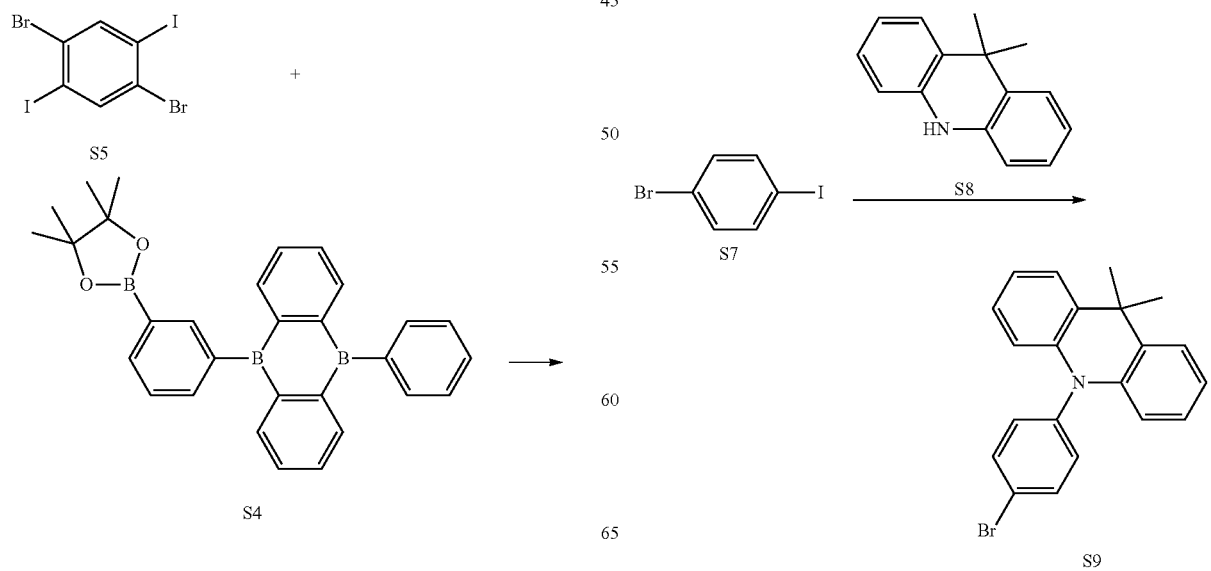

S7 (2.5 mmol), S8 (2.6 mmol), (dibenzylideneacetone) dipalladium (0) (0.12 mmol), sodium tert-butoxide (4 mmol), and tri-tert-butylphosphine tetrafluoroborate (0.25 mmol) were put into a 100 ml three-necked flask, degassing and nitrogen replacement were repeated three times rapidly while stirring, and 40 ml toluene was added through a syringe. The mixture was heated to reflux for 3 h under nitrogen flow. After reaction, the reaction solution was cooled to room temperature, added with water, extracted with dichloromethane, and washed with saturated brine. The organic layer was dried over anhydrous sodium sulfate, distillated to remove the solvent, and purified by column chromatography to obtain an intermediate S9 (1.85 mmol, 74%).

MALDI-TOF MS: $C_{21}H_{18}BrN$, m/z calculated: 363.1; measured: 363.4.

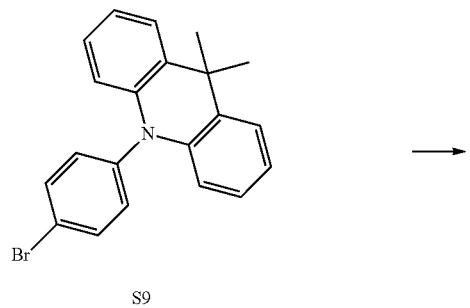

S9

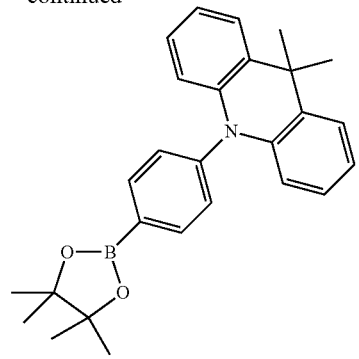

S10

In a 100 ml three-necked flask, S9 (1.8 mmol), bis(pinacolato)diboron (2.2 mmol), (1,1'-bis(diphenylphosphino)ferrocene) dichloropalladium (II) (0.05 mmol), and potassium acetate (12 mmol) were first added separately, degassing and nitrogen replacement were quickly repeated for 3 times while stirring, and 8 mL tetrahydrofuran was added through a syringe. Under stirring at a certain rotation speed, the obtained mixed solution reactant was heated to reflux at a reaction temperature of 80° C. for 5 h; after the reaction was completed, it was cooled to room temperature, 6 ml water added, and extracted with diethyl ether, the obtained organic phase was dried with anhydrous sodium sulfate, evaporated to remove the solvent, and purified using column chromatography to obtain an intermediate S10 (1.4 mmol, 78%).

MALDI-TOF MS: $C_{27}H_{30}BNO_2$, m/z calculated: 411.2; measured: 411.3.

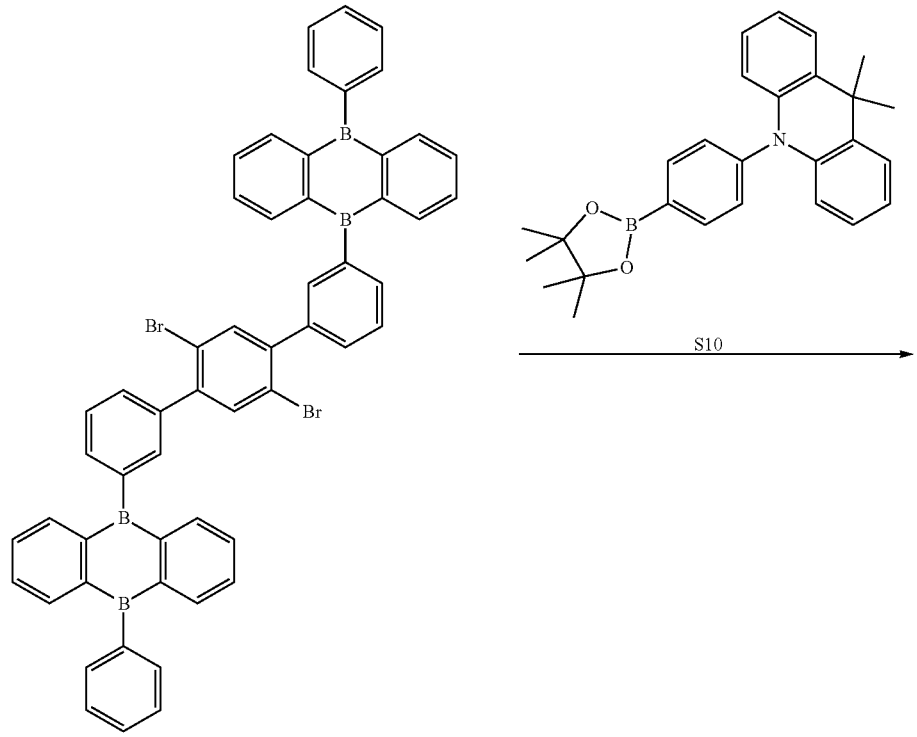

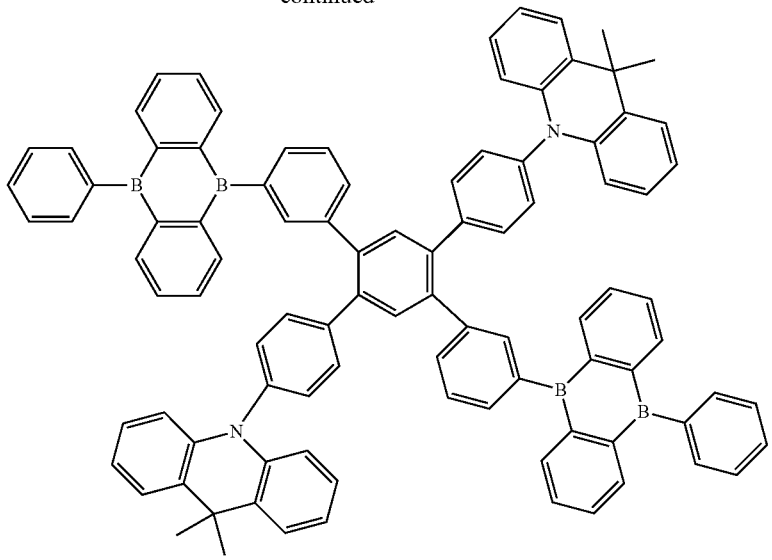

P7

Under nitrogen protection, compounds S6 (2.0 mmol), S4 (4.5 mmol), [Pd$_2$(dba)$_3$]·CHCl$_3$ (0.08 mmol) and HP(tBu)$_3$·BF$_4$ (0.16 mmol) were weighed and added to a 250 mL two-necked flask. 80 mL toluene (previously treated with N$_2$ for 15 min to remove oxygen) was injected to the two-neck flask, and then 8 mL aqueous solution (1M) of K$_2$CO$_3$ (previously treated with N$_2$ for 15 min to remove oxygen) was added dropwise, and stirred at room temperature overnight. After the reaction was completed, 20 mL deionized water was added, and then a few drops of 2M HCl were added. The reaction solution was extracted with dichloromethane, and the organic phase was collected and dried with anhydrous Na$_2$SO$_4$. The dried solution was filtered, and the solvent was removed on a rotary evaporator to obtain a crude product. The crude product was purified by silica gel chromatography column to obtain a solid P7 (1.4 mmol, 70%).

MALDI-TOF MS: C$_{96}$H$_{72}$B$_4$N$_2$, m/z calculated: 1296.6; measured: 1296.8.

Elemental analysis results: C, 88.91; H, 5.60; B, 3.33; N, 2.16; measured: C, 88.94; H, 5.61; B, 3.31; N, 2.14.

Synthesis of Compound P39

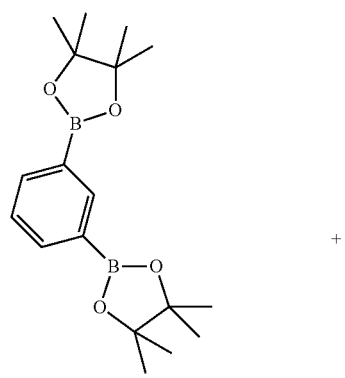

S11

+

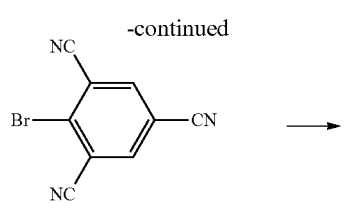

S12

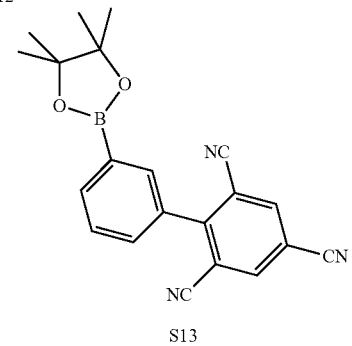

S13

Under nitrogen protection, compound S11 (3.5 mmol), compound S12 (3.8 mmol), [Pd$_2$(dba)$_3$]·CHCl$_3$ (0.15 mmol), and HP(tBu)$_3$·BF$_4$ (0.3 mmol) were weighed and added to a 250 mL two-necked flask. 25 mL toluene (previously treated with N$_2$ for 15 min to remove oxygen) was injected to the two-necked flask, then 3 mL aqueous solution (1M) of K$_2$CO$_3$ (previously treated with N$_2$ for 15 min to remove oxygen) was added dropwise, and stirred at room temperature overnight. After the reaction was completed, 25 mL deionized water was added, and then a few drops of 2M HCl were added. The solution was extracted with dichloromethane, and the organic phase was collected and dried with anhydrous Na$_2$SO$_4$. The dried solution was filtered, and the solvent was removed on a rotary evaporator to obtain a crude product. The crude product was purified by a silica gel chromatography column to finally obtain a solid S13 (2.4 mmol, 68%).

MALDI-TOF MS: C$_{21}$H$_{18}$BN$_3$O$_2$, m/z calculated: 355.2; measured: 355.5.

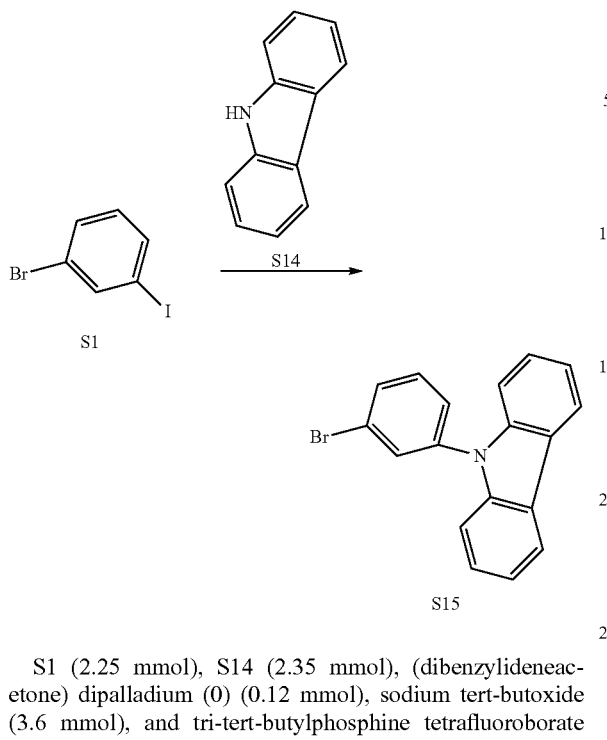

S1 (2.25 mmol), S14 (2.35 mmol), (dibenzylideneacetone) dipalladium (0) (0.12 mmol), sodium tert-butoxide (3.6 mmol), and tri-tert-butylphosphine tetrafluoroborate (0.25 mmol) were put into a 100 ml three-necked flask, degassing and nitrogen replacement were repeated three times rapidly while stirring, and 35 ml toluene was added through a syringe. The mixture was heated to reflux for 3 h under nitrogen gas flow. After reaction, the reaction solution was cooled to room temperature, added with water, and the reaction solution was extracted with dichloromethane and washed with saturated brine. The organic layer was dried with anhydrous sodium sulfate, distillated to remove the solvent, and purified by column chromatography to obtain an intermediate S15 (1.73 mmol, 77%).

MALDI-TOF MS: $C_{24}H_{24}BNO_2$, m/z calculated: 369.2; measured: 369.5.

In a 100 ml three-necked flask, S15 (1.35 mmol), bis(pinacolato)diboron (1.65 mmol), (1,1'-bis(diphenylphosphino)ferrocene) dichloropalladium (II) (0.05 mmol), and potassium acetate (9 mmol) were first added separately, degassing and nitrogen replacement were quickly repeated for 3 times while stirring, and 6 mL tetrahydrofuran was added through a syringe. Under stirring at a certain rotation speed, the obtained mixed solution reactant was heated to reflux at a reaction temperature of 80° C. for 5 h. After the reaction was completed, it was cooled to room temperature, added with 6 ml water, and extracted with diethyl ether, the obtained organic phase was dried with anhydrous sodium sulfate, evaporated to remove the solvent, and purified using column chromatography to obtain an intermediate S16 (1.1 mmol, 81%).

MALDI-TOF MS: $C_{24}H_{24}BNO_2$, m/z calculated: 369.2; measured: 369.3.

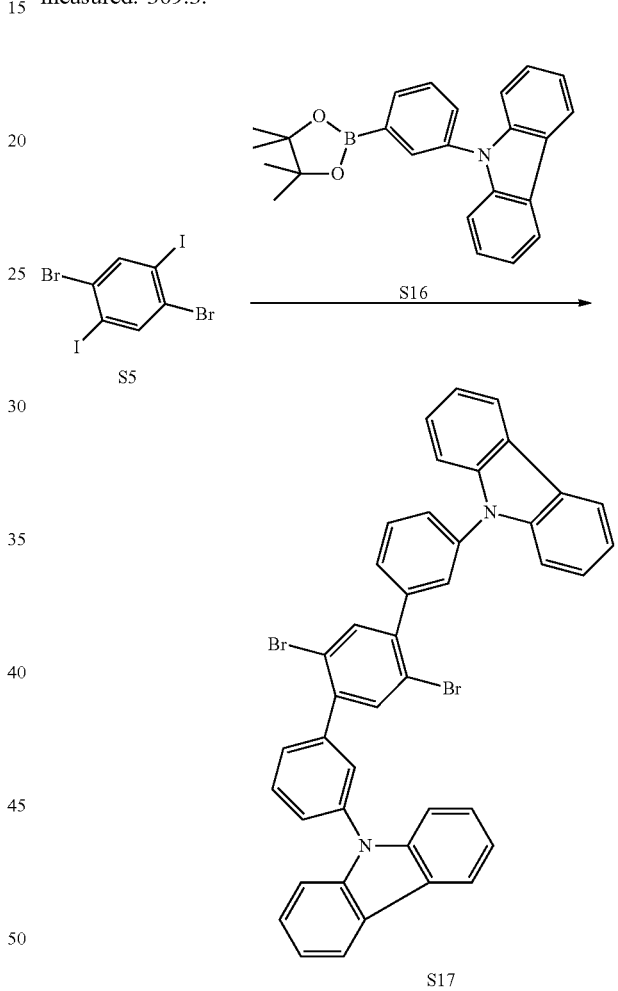

Under nitrogen protection, compound S5 (3.6 mmol), compound S16 (7.8 mmol), $[Pd_2(dba)_3]·CHCl_3$ (0.15 mmol), and $HP(tBu)_3·BF_4$ (0.30 mmol) were weighed and added to a 250 mL two-necked flask. 100 mL toluene (previously treated with $N_2$ for 15 min to remove oxygen) was injected to the two-neck flask, then 6.5 mL aqueous solution (1M) of $K_2CO_3$ (previously treated with $N_2$ for 15 min to remove oxygen) was added dropwise, and stirred at room temperature overnight. After the reaction was completed, 25 mL deionized water was added, and then a few drops of 2M HCl were added. The reaction solution was extracted with dichloromethane, and the organic phase was collected and dried with anhydrous $Na_2SO_4$. The dried solution was filtered, and the solvent was removed on a rotary evaporator to obtain a crude product. The crude product was purified by silica gel chromatography column to obtain a solid P17 (2.5 mmol, 69%).

MALDI-TOF MS: $C_{42}H_{26}Br_2N_2$: m/z calculated: 716.0; measured: 716.2.

crude product. The crude product was purified by a silica gel chromatography column to finally obtain a solid S39 (0.8 mmol, 66%).

MALDI-TOF MS: $C_{72}H_{38}N_8$, m/z calculated: 1014.3; measured: 1014.5.

Elementary analysis results: C, 85.19; H, 3.77; N, 11.04; measured: C, 85.21; H, 3.76; N, 11.01.

Synthesis of Compound P66

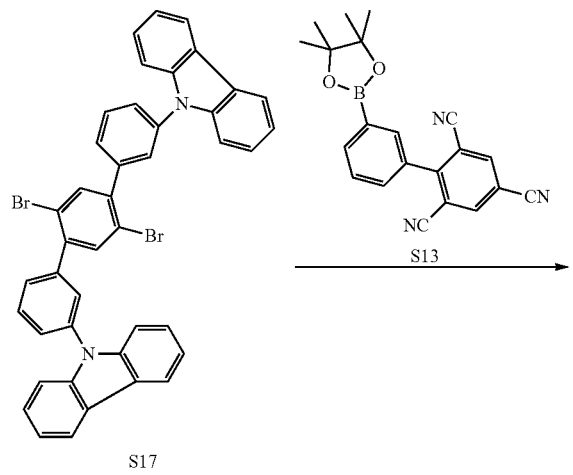

S17

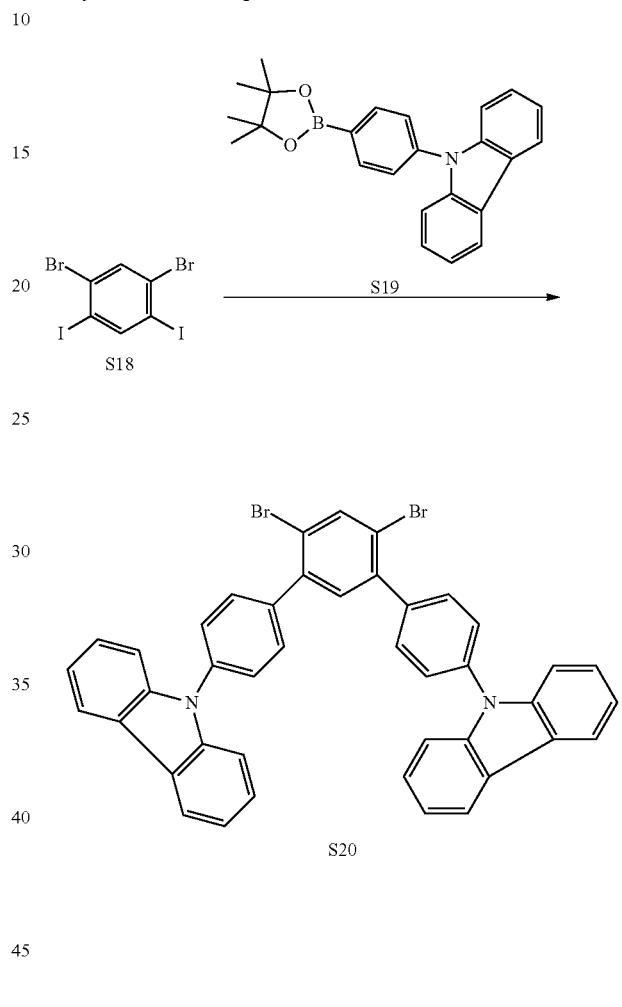

P39

Under nitrogen protection, compound S17 (1.2 mmol), compound S13 (2.7 mmol), [Pd$_2$(dba)$_3$]·CHCl$_3$ (0.06 mmol), and HP(tBu)$_3$·BF$_4$ (0.12 mmol) were weighed and added to a 250 mL two-necked flask. 50 mL toluene (previously treated with N$_2$ for 15 min to remove oxygen) was injected to the two-necked flask, then 6 mL aqueous solution (1M) of K$_2$CO$_3$ (previously treated with N$_2$ for 15 min to remove oxygen) was added dropwise, and stirred at room temperature overnight. After the reaction was completed, 15 mL deionized water was added and then a few drops of 2M HCl were added. The solution was extracted with dichloromethane, and the organic phase was collected and dried with anhydrous Na$_2$SO$_4$. The dried solution was filtered, and the solvent was removed by a rotary evaporator to give a Under nitrogen protection, compound S18 (2.2 mmol), compound S19 (4.8 mmol), [Pd$_2$(dba)$_3$]·CHCl$_3$ (0.10 mmol), and HP(tBu)$_3$·BF$_4$ (0.20 mmol) were weighed and added to a 250 mL two-necked flask. 70 mL toluene (previously treated with N$_2$ for 15 min to remove oxygen) was injected to the two-neck flask, and then 5 mL aqueous solution (1M) of K$_2$CO$_3$ (previously treated with N$_2$ for 15 min to remove oxygen) was added dropwise, and stirred at room temperature overnight. After the reaction was completed, 20 mL deionized water was added, and then a few drops of 2M HCl were added. The reaction solution was extracted with dichloromethane, and the organic phase was collected and dried with anhydrous Na$_2$SO$_4$. The dried solution was filtered, and the solvent was removed on a rotary evaporator to obtain a crude product. The crude product was purified by silica gel chromatography column to obtain a solid P20 (1.5 mmol, 68%).

MALDI-TOF MS: $C_{42}H_{26}Br_2N_2$: m/z calculated: 716.0; measured: 716.3.

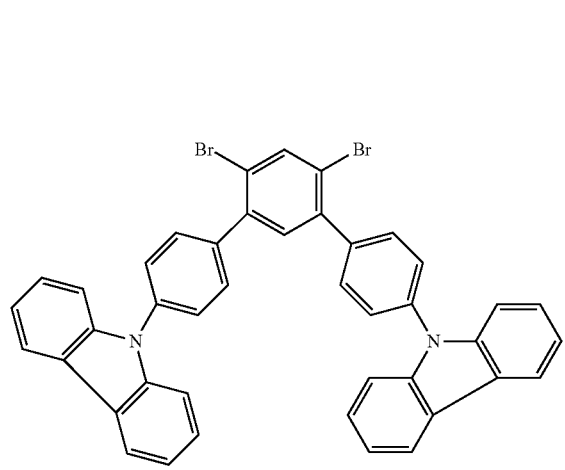

S20

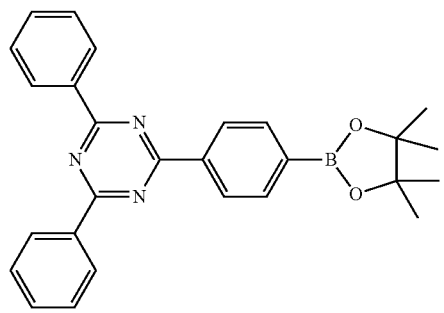

S21

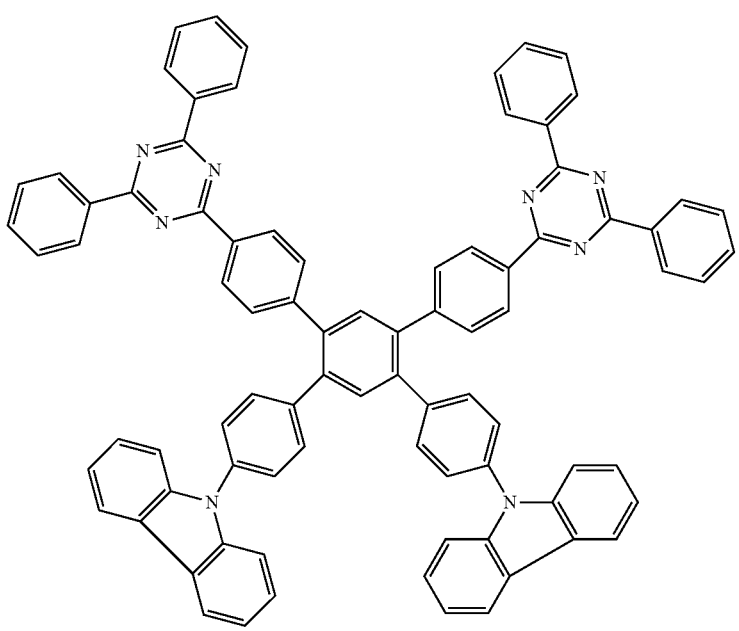

P66

Under nitrogen protection, compound S20 (1.8 mmol), compound S21 (3.9 mmol), [Pd$_2$(dba)$_3$]·CHCl$_3$ (0.10 mmol), and HP(tBu)$_3$·BF$_4$ (0.20 mmol) were weighed and added to a 250 mL two-necked flask. 60 mL toluene (previously treated with N$_2$ for 15 min to remove oxygen) was injected to the two-neck flask, and then 5 mL aqueous solution (1M) of K$_2$CO$_3$ (previously treated with N$_2$ for 15 min to remove oxygen) was added dropwise, and stirred at room temperature overnight. After the reaction was completed, 15 mL deionized water was added, and then a few drops of 2M HCl were added. The reaction solution was extracted with dichloromethane, and the organic phase was collected and dried with anhydrous Na$_2$SO$_4$. The dried solution was filtered, and the solvent was removed on a rotary evaporator to obtain a crude product. The crude product was purified by silica gel chromatography column to obtain a solid P66 (1.3 mmol, 72%).

MALDI-TOF MS: C$_{84}$H$_{54}$N$_8$, m/z calculated: 1174.4; measured: 1174.5.

Elementary analysis results: C, 85.84; H, 4.63; N, 9.53; measured: C, 85.86; H, 4.64; N, 9.50.

Synthesis of Compound P71

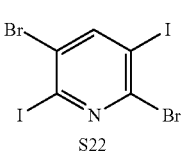

S22

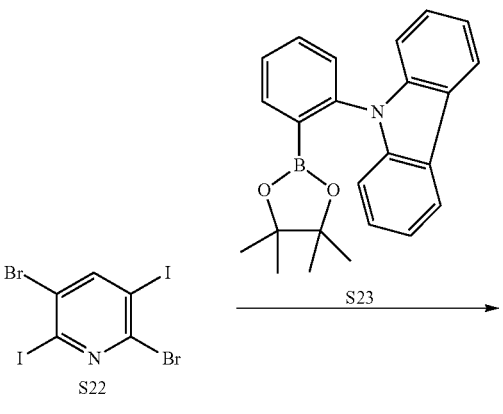

S23

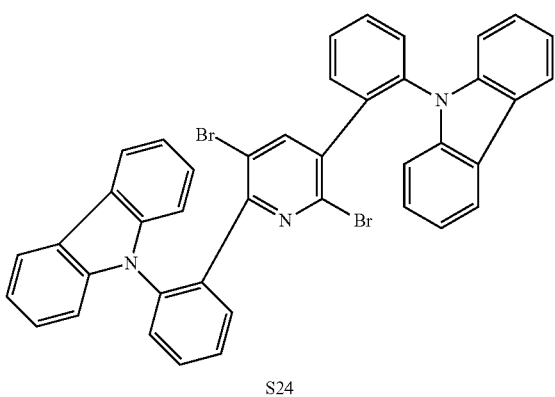

S24

Under nitrogen protection, compound S22 (2.5 mmol), compound S23 (5.5 mmol), [Pd$_2$(dba)$_3$]·CHCl$_3$ (0.12 mmol), and HP(tBu)$_3$·BF$_4$ (0.24 mmol) were weighed and added to a 250 mL two-necked flask. 80 mL toluene (previously treated with N$_2$ for 15 min to remove oxygen) was injected to the two-neck flask, and then 5.8 mL aqueous solution (1M) of K$_2$CO$_3$ (previously treated with N$_2$ for 15 min to remove oxygen) was added dropwise, and stirred at room temperature overnight. After the reaction was completed, 25 mL deionized water was added, and then a few drops of 2M HCl were added. The reaction solution was extracted with dichloromethane, and the organic phase was collected and dried with anhydrous Na$_2$SO$_4$. The dried solution was filtered, and the solvent was removed on a rotary evaporator to obtain a crude product. The crude product was purified by silica gel chromatography column to obtain a solid S24 (1.9 mmol, 76%).

MALDI-TOF MS: C$_{42}$H$_{26}$Br$_2$N$_2$: m/z calculated: 716.0; measured: 716.3.

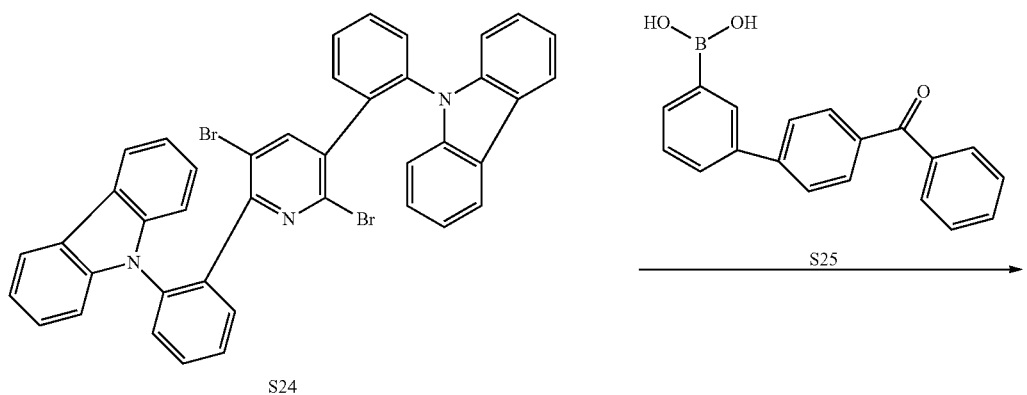

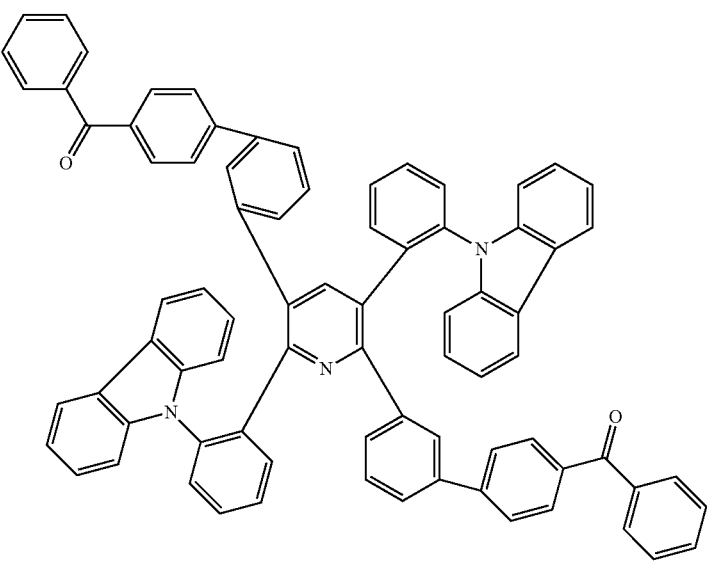

P71

Under nitrogen protection, compound S24 (3.3 mmol), compound S25 (7.2 mmol), [Pd$_2$(dba)$_3$]·CHCl$_3$ (0.15 mmol), and HP(tBu)$_3$·BF$_4$ (0.30 mmol) were weighed and added to a 250 mL two-necked flask. 100 mL toluene (previously treated with N$_2$ for 15 min to remove oxygen) was injected to the two-neck flask, and then 8 mL aqueous solution (1M) of K$_2$CO$_3$ (previously treated with N$_2$ for 15 min to remove oxygen) was added dropwise, and stirred at room temperature overnight. After the reaction was completed, 30 mL deionized water was added, and then a few drops of 2M HCl were added. The reaction solution was extracted with dichloromethane, and the organic phase was collected and dried with anhydrous Na$_2$SO$_4$. The dried solution was filtered, and the solvent was removed on a rotary evaporator to obtain a crude product. The crude product was purified by silica gel chromatography column to obtain a solid P71 (2.7 mmol, 82%).

MALDI-TOF MS: C$_{79}$H$_{51}$N$_3$O$_2$: m/z calculated: 1073.4; measured: 1075.6.

Elementary analysis results: C, 88.32; H, 4.79; N, 3.91; O, 2.98; measured: C, 88.35; H, 4.81; N, 3.89; O, 2.95.

Synthesis of Compound P103

Under nitrogen protection, compound S26 (1.5 mmol), compound S4 (3.2 mmol), [Pd$_2$(dba)$_3$]·CHCl$_3$ (0.08 mmol), and HP(tBu)$_3$·BF$_4$ (0.15 mmol) were weighed and added to a 250 mL two-necked flask. 50 mL toluene (previously treated with N$_2$ for 15 min to remove oxygen) was injected to the two-neck flask, and then 3.5 mL aqueous solution (1M) of K$_2$CO$_3$ (previously treated with N$_2$ for 15 min to remove oxygen) was added dropwise, and stirred at room temperature overnight. After the reaction was completed, 15 mL deionized water was added, and then a few drops of 2M HCl were added. The reaction solution was extracted with dichloromethane, and the organic phase was collected and dried with anhydrous Na$_2$SO$_4$. The dried solution was filtered, and the solvent was removed on a rotary evaporator to obtain a crude product. The crude product was purified by silica gel chromatography column to obtain a solid S27 (1.2 mmol, 80%).

MALDI-TOF MS: C$_{58}$H$_{38}$B$_4$Br$_2$: m/z calculated: 936.2; measured: 936.3.

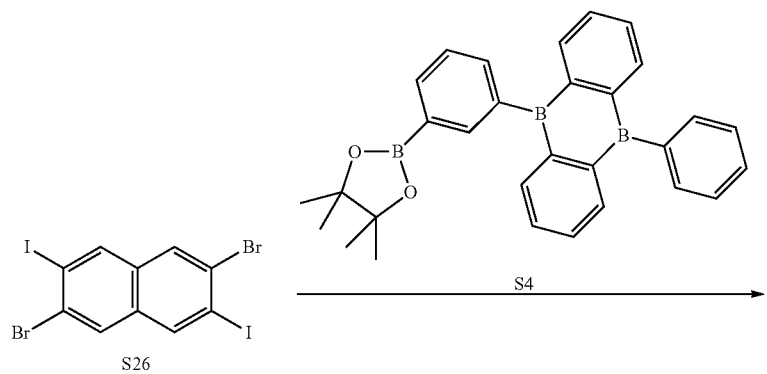

S26

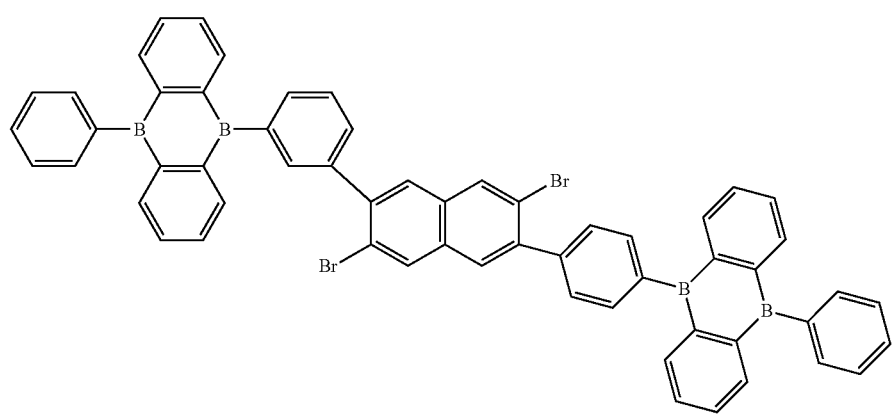

S27

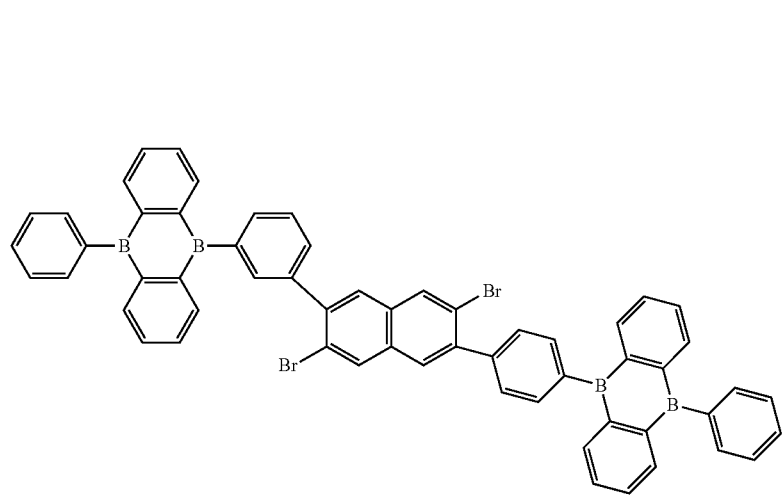

S27

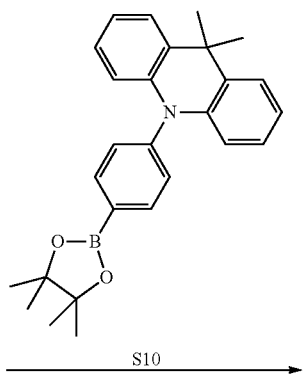

S10

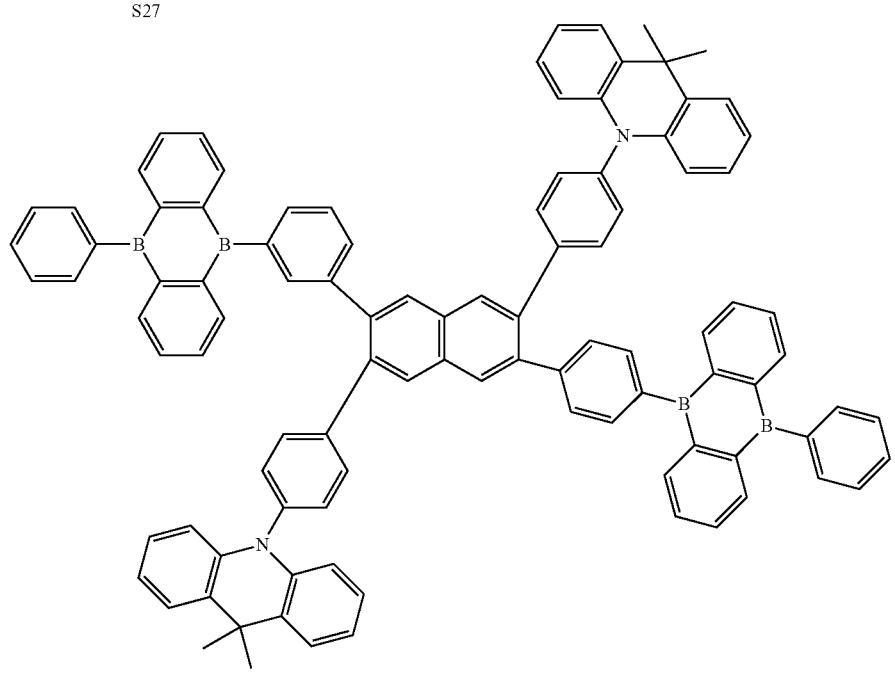

P103

Under nitrogen protection, compound S27 (1.3 mmol), compound S10 (2.9 mmol), [Pd$_2$(dba)$_3$]·CHCl$_3$ (0.08 mmol), and HP(tBu)$_3$·BF$_4$ (0.16 mmol) were weighed and added to a 250 mL two-necked flask. 40 mL toluene (previously treated with N$_2$ for 15 min to remove oxygen) was injected to the two-neck flask, and then 4 mL aqueous solution (1M) of K$_2$CO$_3$ (previously treated with N$_2$ for 15 min to remove oxygen) was added dropwise, and stirred at room temperature overnight. After the reaction was completed, 15 mL deionized water was added, and then a few drops of 2M HCl were added. The reaction solution was extracted with dichloromethane, and the organic phase was collected and dried with anhydrous Na$_2$SO$_4$. The dried solution was filtered, and the solvent was removed on a rotary evaporator to obtain a crude product. The crude product was purified by silica gel chromatography column to obtain a solid P103 (0.98 mmol, 75%).

MALDI-TOF MS: C$_{100}$H$_{74}$B$_4$N$_2$: m/z calculated: 1346.6; measured: 1346.8.

Elementary analysis results: C, 89.17; H, 5.54; B, 3.21; N, 2.08; measured: C, 89.19; H, 5.57; B, 3.18; N, 2.06.

Example 1 to Example 8

With respect to compounds P7, P14, P30, P39, P48, P56, P86, P89, and P103, the distributions of the molecular frontier orbitals HOMO and LUMO were optimized and calculated by applying a density functional theory (DFT) and using a Gaussian 09 software with B3LYP/6-31G calculation level. Meanwhile, the singlet energy level S$_1$ and the triplet energy level T$_1$ were simulated and calculated based on a time-dependent density functional theory (TDDFT).

TABLE 1

Relevant Performance Data of Compounds

| Example | Compound | HOMO (eV) | LUMO (eV) | Eg (eV) | $S_1$ (eV) | $T_1$ (eV) | $\Delta E_{ST}$ (eV) |
|---|---|---|---|---|---|---|---|
| Example 1 | P7 | −5.82 | −2.92 | 2.70 | 2.452 | 2.451 | 0.001 |
| Example 2 | P14 | −5.78 | −2.76 | 3.02 | 3.27 | 3.16 | 0.11 |
| Example 3 | P30 | −5.65 | −2.68 | 2.97 | 2.622 | 2.620 | 0.002 |
| Example 4 | P39 | −5.93 | −2.98 | 2.95 | 2.98 | 2.93 | 0.05 |
| Example 5 | P48 | −5.87 | −2.75 | 3.12 | 3.52 | 3.25 | 0.27 |
| Example 6 | P56 | −5.45 | −2.48 | 2.97 | 2.63 | 2.59 | 0.04 |
| Example 7 | P86 | −5.93 | −3.02 | 2.91 | 2.506 | 2.505 | 0.001 |
| Example 8 | P89 | −5.75 | −2.72 | 3.03 | 2.79 | 2.70 | 0.09 |
| Example 9 | P103 | −5.60 | −2.65 | 2.95 | 2.64 | 2.58 | 0.06 |

Notes:
$S_1$ represents a singlet energy level, $T_1$ represents a triplet energy level, and $E_g$ represents a HOMO-LUMO energy level difference.

It can be seen from Table 1 that the $\Delta E_{ST}$ of each of the compounds is less than 0.3 ev, which means a smaller singlet-triplet energy level difference, such that these compounds have the properties of the TADF materials, and can be used as a guest material of the organic light-emitting layer. In addition, the compounds of the present disclosure all have higher singlet energy level and higher triplet energy level, and thus are also suitable as a host material in the light-emitting layer.

The present disclosure also provides a display panel including an organic light-emitting device, the organic light-emitting device includes an anode, a cathode disposed opposite to the anode, and a light-emitting layer disposed between the anode and the cathode, and a light-emitting material of the light-emitting layer includes one or more of the compounds provided in the present disclosure.

According to an embodiment of the display panel of the present disclosure, the light-emitting material of the light-emitting layer includes a host material and a guest material, and the host material is one or more of the compounds provided in the present disclosure.

According to an embodiment of the display panel of the present disclosure, the light-emitting layer includes a red light-emitting layer, and the host material is a red light host material.

According to an embodiment of the display panel of the present disclosure, the light-emitting layer includes a green light-emitting layer, and the host material is a green light host material.

According to an embodiment of the display panel of the present disclosure, the organic light-emitting device further includes one or more of a hole injection layer, a hole transmission layer, an electron blocking layer, a hole blocking layer, an electron transmission layer, or an electron injection layer.

The hole injection layer, the hole transmission layer, and the electron blocking layer can be made of a material selected from 2,2'-dimethyl-N,N'-di-1-naphthyl-N,N'-diphenyl [1,1'-biphenyl]-4,4'-diamine (α-NPD), 4,4',4''-tris(carbazol-9-yl)triphenylamine (TCTA), 1,3-bis(N-dicarbazolyl) benzene (mCP), 4,4'-bis(N-carbazolyl)-1,1'-biphenyl (CBP), 3,3'-bis(N-carbazolyl)-1,1'-biphenyl (mCBP), 2,3,6,7,10,11-hexacyano-1,4,5,8,9,12-hexaazatriphenylene (HATCN), 4,4'-cyclohexyldi[N,N-bis(4-methylphenyl)aniline (TAPC), N,N'-bis-(1-naphthalenyl)-N,N'-bis-phenyl-(1,1'-biphenyl)-4,4'-diamine (α-NPB), N,N'-bis(naphthalene-2-yl)-N,N'-bis(phenyl)benzidine (NPB), poly(3,4-ethylenedioxythiophene)-poly(styrenesulfonate) (PEDOT:PSS), polyvinylcarbazole (PVK), 9-phenyl-3,9-bicarbazole (CCP), molybdenum trioxide ($MoO_3$), and the like, but not limited to the above materials.

The hole blocking layer, the electron transmission layer, and the electron injection layer can be made of a material selected from the group consisting of 2,8-bis(diphenylphosphoryl)dibenzothiophene (PPT), $TSPO_1$, 1,3,5-tris(1-phenyl-1H-benzimidazol-2-yl)benzene (TPBi), 2,8-bis(diphenylphosphoryl) dibenzofuran (PPF), bis[2-diphenylphosphino)phenyl]ether oxide (DPEPO), lithium fluoride (LiF), 4,6-bis(3,5-di(pyridin-3-yl)phenyl)-2-methylpyrimidine (B3PYMPM), 4,7-diphenyl-1,10-phenanthroline (Bphen), 1,3,5-tris[(pyridin-3-yl)-3-phenyl]benzene (TmPyBP), tris[2,4,6-trimethyl-3-(pyridin-3-yl)phenyl]borane (3TPYMB), 1,3-bis(3,5-di(pyridin-3-yl)phenyl)benzene (B3PYPB), 1,3-bis[3,5-di(pyridin-3-yl)phenyl]benzene (BMPYPHB), 2,4,6-tris(biphenyl-3-yl)-1,3,5-triazine (T2T), diphenyl bis[4-(pyridin-3-yl)phenyl]silane (DPPS), cesium carbonate ($Cs_2O_3$), bis(2-methyl-8-quinolinolato-N1,$O_8$)-(1,1'-biphenyl-4-olato)aluminum (BAlq), 8-hydroxyquinolinolato-lithium (Liq), tris(8-hydroxyquinoline) aluminum ($Alq_3$), or the like, but not limited to the above materials.

In an embodiment of the organic light-emitting display apparatus provided by the present disclosure, the light-emitting layer includes a host material and a guest material. The host material is selected from the group consisting of 2,8-bis(diphenylphosphoryl)dibenzothiophene, 4,4'-bis(N-carbazolyl)-1,1'-biphenyl, 3,3'-bis(N-carbazolyl)-1,1'-biphenyl, 2,8-bis(diphenylphosphoryl)dibenzofuran bis(4-(9H-carbazolyl-9-yl)phenyl)diphenylsilane, 9-(4-tert-butylphenyl)-3,6-bis(triphenylsilyl)-9H-carbazole, bis[2-diphenylphosphino)phenyl]ether, 1,3-bis[3,5-di(pyridin-3-yl)phenyl]benzene, 4,6-bis(3,5-di(pyridin-3-yl)phenyl)-2-methylpyrimidine, 9-(3-(9H-carbazolyl-9-yl)phenyl)-9H-carbazole-3-carbonitrile, 9-phenyl-9-[4-(triphenylsilyl) phenyl]-9H-fluorene, 1,3,5-tris(1-phenyl-1H-benzimidazol-2-yl)benzene, diphenyl[4-(triphenylsilyl)phenyl]phosphine oxide, 4,4',4''-tris(carbazol-9-yl)triphenylamine, 2,6-dicarbazole-1,5-pyridine, polyvinylcarbazole, polyfluorene, and combinations thereof. The guest material may be selected from the group consisting of a fluorescent material, a phosphorescent material, a thermally activated delayed fluorescent material, an aggregation-inducing light-emitting material, and combinations thereof.

In the display panel provided by the present disclosure, in an embodiment, the anode of the organic light-emitting device a metal, such as a metal selected from as the group consisting of copper, gold, silver, iron, chromium, nickel, manganese, palladium, platinum, and alloys thereof. In an embodiment, the anode comprises a metal oxide, such as a metal oxide selected from the group consisting of indium oxide, zinc oxide, indium tin oxide (ITO), indium zinc oxide (IZO), and combinations thereof. In an embodiment, the anode comprises a conductive polymer, such as a conductive polymer selected from the group consisting of polyaniline, polypyrrole, poly(3-methylthiophene) and the combinations thereof. In addition to the anode material mentioned above, the anode also can be made of any suitable material selected from the anode materials known in the related art, and combinations thereof, as long as the material of the anode is conductive to injecting holes.

In the display panel provided by the present disclosure, in an embodiment, the cathode of the organic light-emitting device comprises a metal, such as a metal selected from the group consisting of aluminum, magnesium, silver, indium, tin, titanium, and alloys thereof. In an embodiment, the cathode comprises a multiple-layer metal material, such as a multiple-layer metal material selected from the group consisting of LiF/Al, LiO$_2$/Al, BaF$_2$/Al, and combinations thereof. In addition to the cathode materials listed above, the cathode also can be made of any suitable material selected from the cathode material known in the related art, and combinations thereof, as long as the material of the cathode is conductive to injecting holes.

The organic light-emitting device can be fabricated according to methods well known in the art, which will not be described in detail herein. In the present disclosure, the organic light-emitting display device can be manufactured by forming an anode on a transparent or opaque smooth substrate, forming an organic thin layer on the anode, and further forming a cathode on the organic thin layer. The organic thin layer can be formed by a known method such as vapor deposition, sputtering, spin coating, dipping, ion plating, and the like.

Figure 3:
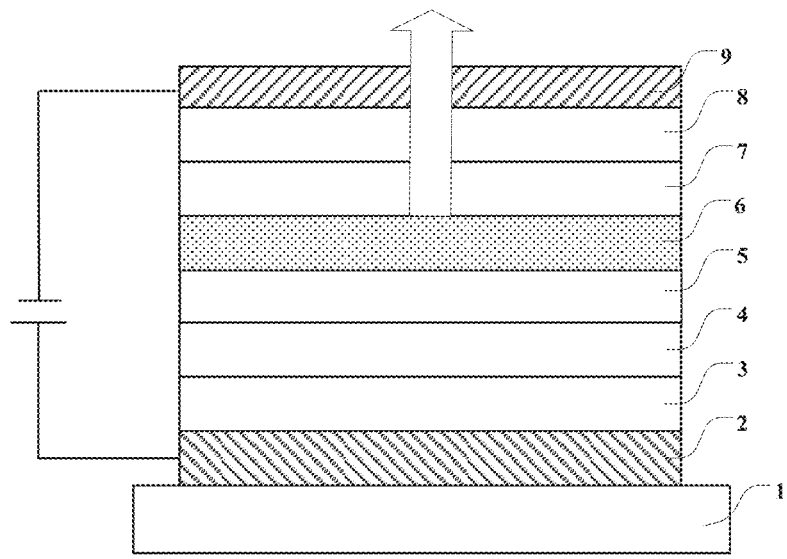
FIG. 3 is a structural schematic diagram of an OLED provided by an embodiment of the present disclosure.

The organic electroluminescent device provided by the present disclosure, as shown in FIG. 3, includes: a substrate 1, an ITO anode 2, a hole injection layer 3, a first hole transmission layer 4, a second hole transmission layer 5, a light-emitting layer 6, a first electron transmission layer 7, a second electron transmission layer 8, and a cathode 9 (silver electrode).

Example 9

The present example provides an organic electroluminescent device prepared by the following preparation steps:

1) the glass substrate 1 was cut into a size of 50 mm×50 mm×0.7 mm, ultrasonically cleaned in acetone, isopropyl alcohol and deionized water for 30 minutes, respectively, and then cleaned under UV ozone for 30 minutes; the obtained glass substrate with an indium tin oxide (ITO) anode layer 2 was mounted on a vacuum deposition apparatus;

2) the compound 1 was deposited on the ITO anode layer 2 by vacuum evaporation as the hole injection layer 3, having a thickness of 10 nm;

3) the compound 2 was deposited on the hole injection layer 3 by vacuum evaporation as the first hole transmission layer 4, having a thickness of 100 nm;

4) the compound 3 was vacuum evaporated on the first hole transmission layer 4 as the second hole transmission layer 5, having a thickness of 10 nm;

5) a light-emitting layer 6 having a thickness of 30 nm was formed on the second hole transmission layer 5 by vacuum evaporation, where the compound mCBP was used as a host material, and compound P7 was used as a dopant (a guest material) with a doping ratio of 3% (mass ratio);

6) compound 5 (an electron transmission type material) was vacuum evaporated on the light-emitting layer 6 as the first electron transmission layer 7, having a thickness of 10 nm;

7) compound 6 (an electron transmission material) was vacuum evaporated on the first electron transmission layer 7 as the second electron transmission layer 8, having a thickness of 30 nm; and 8) the silver electrode was vacuum evaporated on the second electron transmission layer 8 as the cathode 9 having a thickness of 15 nm.

Example 10

Example 10 differs from Example 9 in that compound P7 is replaced by P14.

Example 11

Example 11 differs from Example 9 in that compound P7 is replaced by P30.

Example 12

Example 12 differs from Example 9 in that compound P7 is replaced by P39.

Example 13

Example 13 differs from Example 9 in that compound P7 is replaced by P48.

Example 14

Example 14 differs from Example 9 in that compound P7 is replaced by P56.

Example 15

Example 15 differs from Example 9 in that compound P7 is replaced by P86.

Example 16

Example 16 differs from Example 9 in that compound P7 is replaced by P89.

Example 17

Example 17 differs from Example 9 in that compound P7 is replaced by P103.

Comparative Example 1

Comparative Example 1 differs from Example 9 in that compound P7 is replaced by BCzVBi.

121
122
Compound 1
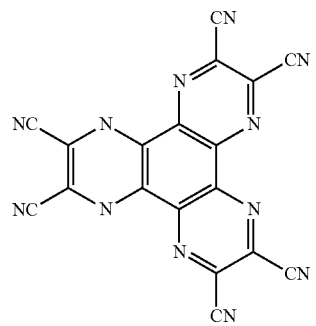
Compound 2
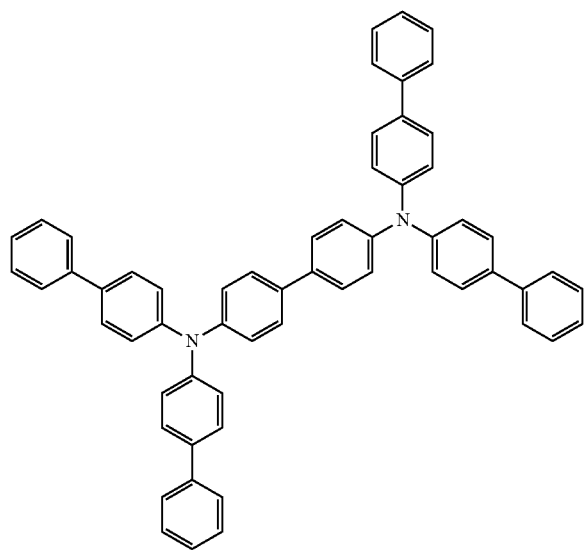
Compound 3
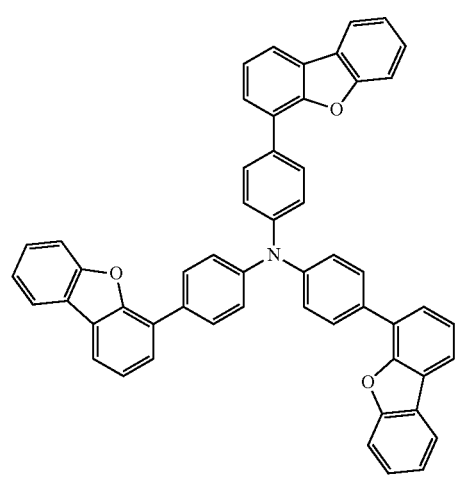
Compound 4
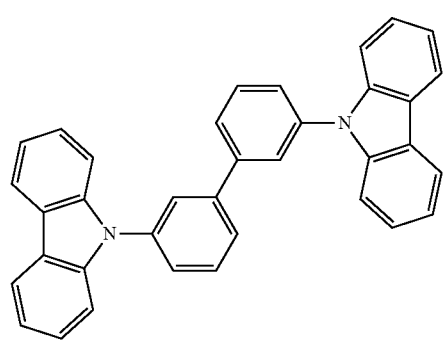
mCBP
Compound 5
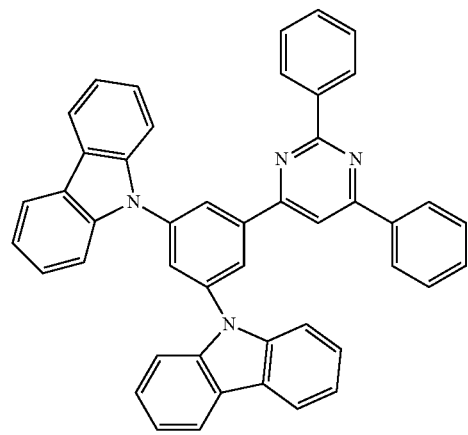
Compound 6
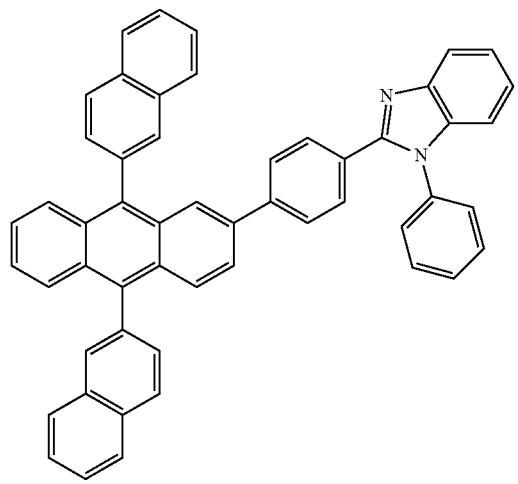

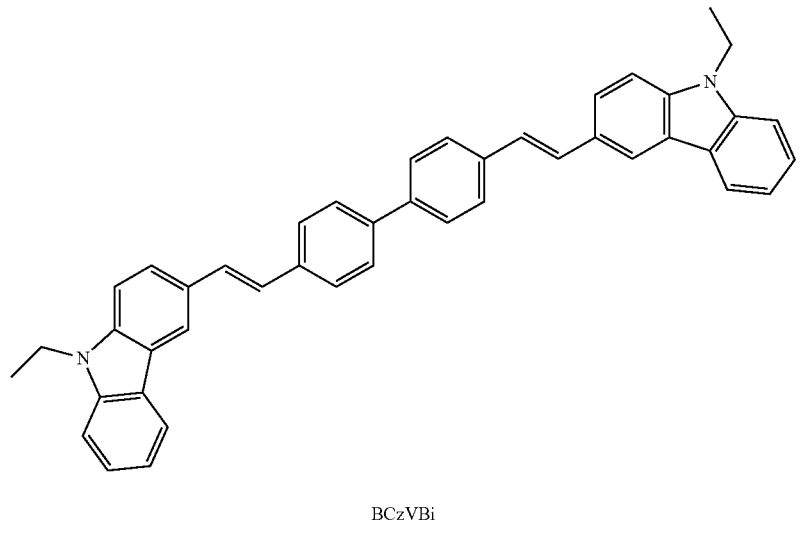

Comparative compound 1

BCzVBi

Tests of Light-Emitting Performance Parameters of OLED Devices

Currents under different voltages of the display panels of the examples and comparative examples were tested with a Keithley 2365A digital nanovoltmeter, and then the currents were divided by a light-emitting area to calculate current densities of the display panels at different voltages. Brightness and radiant energy flow densities of the display panels of the examples and comparative examples at different voltages were tested using a Konica Minolta CS-2000 spectroradiometer. According to the current density and brightness of the display panel at different voltages, an operating voltage $V_{on}$, a current efficiency (Cd/A), and an external quantum efficiency EQE at the same current density (10 mA/cm$^2$) were obtained; and the service time T95 of the organic light-emitting device was obtained by measuring the time when the brightness reached 95% of the initial brightness (under a test condition of 500 nit). The test results are shown in Table 2.

TABLE 2

| Ligth-emitting device | Host material | Guest material | Driving voltage [V] | Current efficiency (10 mA/cm$^2$) (cd · A$^{-1}$) | Service time T95 (h) |
|---|---|---|---|---|---|
| Example 9 | mCBP | P7 | 3.98 | 18.4 | 42 |
| Example 10 | mCBP | P14 | 4.52 | 14.6 | 45 |
| Example 11 | mCBP | P30 | 4.10 | 17.5 | 41 |
| Example 12 | mCBP | P39 | 4.06 | 16.8 | 43 |
| Example 13 | mCBP | P48 | 4.38 | 13.4 | 46 |
| Example 14 | mCBP | P56 | 4.20 | 17.2 | 45 |
| Example 15 | mCBP | P86 | 4.26 | 18.0 | 43 |
| Example 16 | mCBP | P89 | 4.26 | 15.2 | 45 |
| Example 17 | mCBP | P103 | 4.02 | 15.8 | 42 |
| Comparative Example 1 | mCBP | BCzVBi | 5.20 | 6.7 | 40 |

It can be seen from Table 2 that the current efficiency CE of the device of the present disclosure, in which the compound of the present disclosure was used as the blue light host material, is significantly higher than that of the comparative device using the classical blue fluorescent material BCzVBi as a fluorescent dopant. This is mainly attributed to the TADF properties of the compound of the present disclosure, i.e., the compound of the present disclosure has a high-efficient photophysical process of reverse intersystem crossing between the singlet state and the triplet state, and the triplet excitons can be used to emit light, while transition of the triplet excitons is inhibited in the conventional fluorescent molecules such as BCzVBi. Therefore, the devices of the present disclosure have an increased device efficiency.

Since the compound of the present disclosure has the TADF effect, the physical process of reverse inter-system crossing can occur between the triplet state and the singlet state, and singlet excitons and triplet excitons can be utilized synchronously with higher efficiency. Moreover, the compound of the present disclosure has property of bipolarity, and thus has good transmission properties for both holes and electrons, such that the compound can also be used as a host material of the light-emitting layer, thereby broadening the light-emitting region, improving the light-emitting efficiency, and prolonging the service life of the device.

Example 18

Example 18 differs from Example 9 in that the host material mCBP is replaced by P7, and the doping material P7 is replaced by a red light light-emitting material Ir(piq)2acac. Than is, in Example 18, P7 is used as the host material, and Ir(piq)2acac is used as the doping material.

Example 19

Example 19 differs from Example 9 in that mCBP is replaced by P14, and compound P7 is replaced by a green light light-emitting material Ir(ppy)3.

Example 20

Example 20 differs from Example 9 in that mCBP is replaced by P30, and compound P7 is replaced by a red light light-emitting material Ir(piq)2acac.

Example 21

Example 21 differs from Example 9 in that mCBP is replaced by P39, and compound P7 is replaced by a green light light-emitting material Ir(ppy)3.

Example 22

Example 22 differs from Example 9 in that mCBP is replaced by P48, and compound P7 is replaced by a green light light-emitting material Ir(ppy)3.

Example 23

Example 23 differs from Example 9 in that mCBP is replaced by P56, and compound P7 is replaced by a green light light-emitting material Ir(ppy)3.

Example 24

Example 24 differs from Example 9 in that mCBP is replaced by P86, and compound P7 is replaced by a red light light-emitting material Ir(piq)2acac.

Example 25

Example 25 differs from Example 9 in that mCBP is replaced by P89, and compound P7 is replaced by a green light light-emitting material Ir(ppy)3.

Example 26

Example 26 differs from Example 9 in that mCBP is replaced by P103, and compound P7 is replaced by a red light light-emitting material Ir(piq)2acac.

Comparative Example 2

Comparative Example 2 differs from Example 9 in that compound P7 is replaced by Ir(ppy)3.

Comparative Example 3

Comparative Example 3 differs from Example 9 in that compound P7 is replaced by Ir(piq)2acac.

TABLE 3

| Ligth-emitting device | Host material | Guest material | Driving voltage [V] | Current efficiency (10 mA/cm$^2$) (cd·A$^{-1}$) | Service time T95 (h) |
|---|---|---|---|---|---|
| Example 18 | P7 | Ir(piq)2acac | 3.75 | 18.4 | 130 |
| Example 19 | P14 | Ir(ppy)3 | 3.67 | 65 | 70 |
| Example 20 | P30 | Ir(piq)2acac | 3.64 | 16.6 | 128 |
| Example 21 | P39 | Ir(ppy)3 | 3.75 | 63 | 75 |
| Example 22 | P48 | Ir(ppy)3 | 3.52 | 60 | 78 |
| Example 23 | P56 | Ir(ppy)3 | 3.65 | 65 | 75 |
| Example 24 | P86 | Ir(piq)2acac | 3.72 | 16.9 | 135 |
| Example 25 | P89 | Ir(ppy)3 | 3.78 | 62 | 79 |
| Example 26 | P103 | Ir(piq)2acac | 3.68 | 15.8 | 120 |
| Comparative Example 2 | mCBP | Ir(ppy)3 | 4.35 | 58 | 65 |
| Comparative Example 3 | mCBP | Ir(piq)2acac | 4.24 | 13.5 | 80 | mCBP is often used as a phosphorescent host material, Ir(ppy)3 is a frequently used green light phosphorescent material, and Ir(piq)2acac is a commonly used red light phosphorescent material. It can be seen from Table 3 that, the organic light-emitting devices (Example 18 to Example 26), which adopts the compounds P7, P14, P30, P39, P48, P56, P86, P89, and P103 of the present disclosure as the phosphorescent host materials, have higher current efficiency, longer device service time, and lower operating voltage than the comparative devices 2 and 3 using mCBP as the phosphorescent host material. Thus, it can be seen that the compounds of the present disclosure are suitable as phosphorescent host materials for green light and red light.

Figure 4:
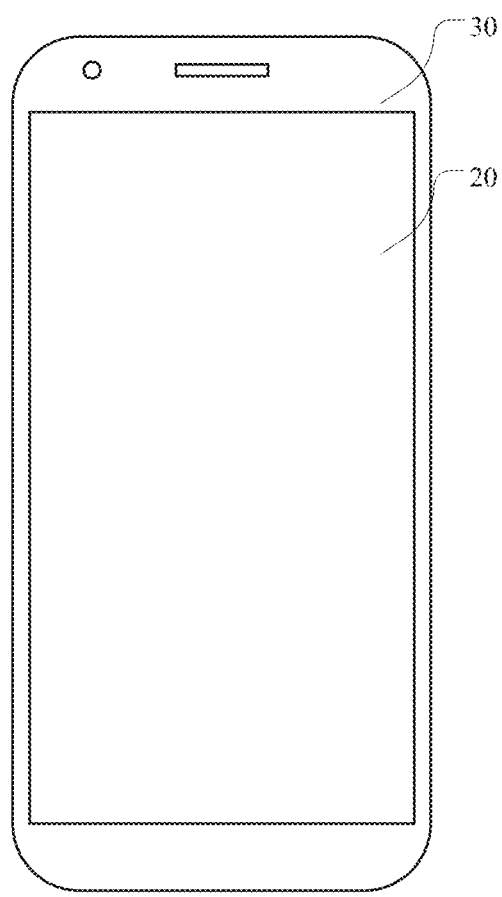
FIG. 4 is a schematic diagram of a display apparatus provided by an embodiment of the present disclosure.

The present disclosure also provides a display apparatus including the organic light-emitting display panel as described above. In the present disclosure, the organic light-emitting device may be an OLED used in an organic light-emitting display apparatus. The organic light-emitting display apparatus may be a mobile phone display screen, a computer display screen, a television display screen, a smart watch display screen, a smart car display panel, a VR or AR helmet display screen, or display screens of various smart equipment, etc. FIG. 4 is a schematic diagram of a display apparatus according to an embodiment of the present disclosure. In FIG. 4, a mobile phone display panel is denoted with reference sign 20, and a display apparatus is denoted with reference sign 30.

The above embodiments of the present disclosure are several preferred embodiments, but not intended to limit the scope of the claims. Any change and modification can be made by those skilled in the art without departing from the scope of the present application. The scope of protection is defined by the claims.

What is claimed is:

1. A compound, having a structure according to Chemical Formula 1:

Chemical Formula 1

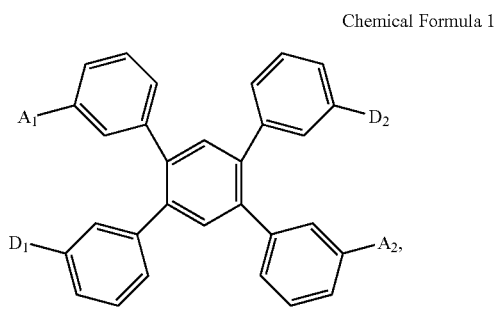

wherein;

wherein A$_1$ and A$_2$ are identical, and D$_1$ and D2 are identical; and wherein D$_1$ and D2 are each independently selected from the group consisting of the following groups:

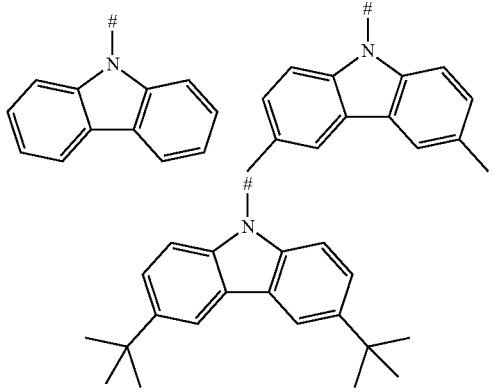

127
-continued
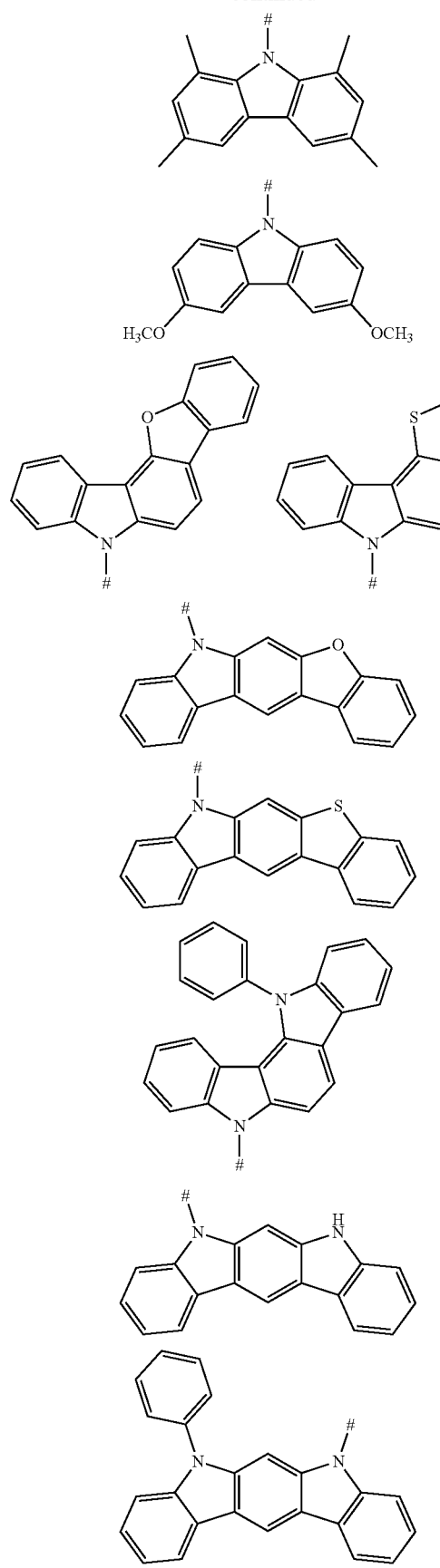
128
-continued
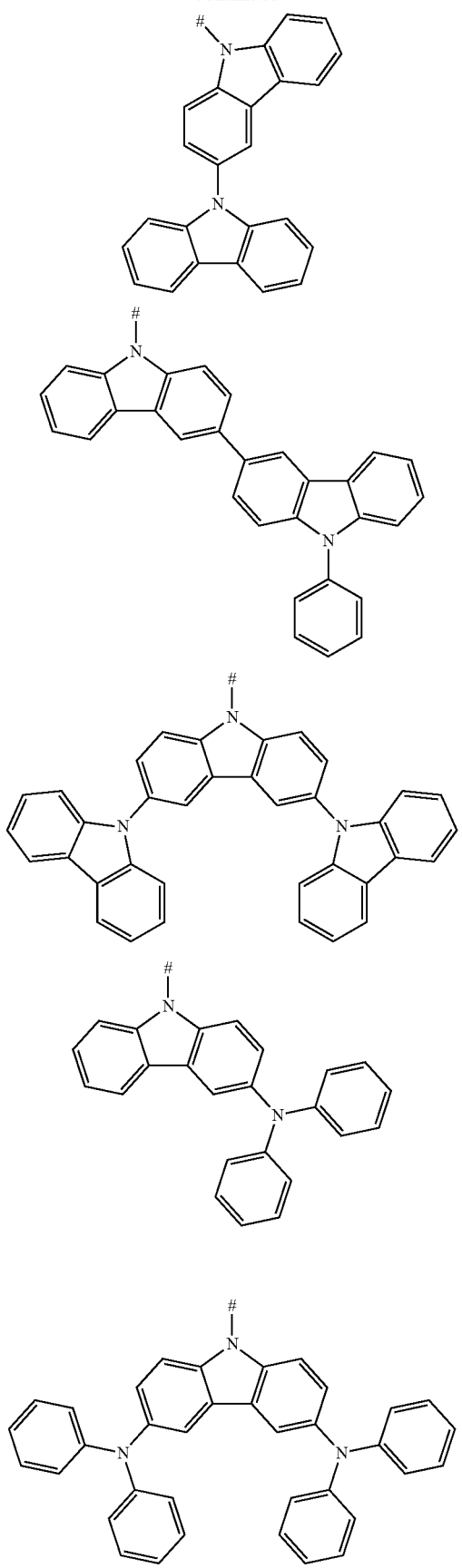

-continued

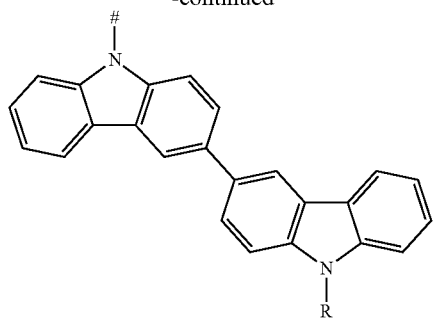

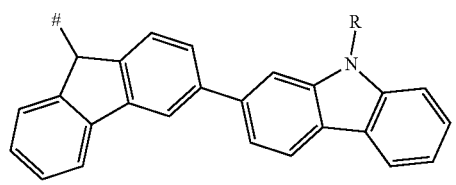

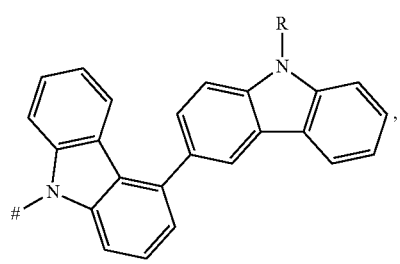

wherein # represents a bonding position in the Chemical Formula 1, and
R represents a C1-C20 alkyl group, a C1-C20 alkoxy group, a C2-C20 alkenyl group, a C2-C20 alkynyl group, a C6-C40 aromatic group, or a C4-C40 heteroaryl group; and
wherein $A_1$ and $A_2$ are each a cyano-containing group, and wherein the cyano-containing group is selected from the group consisting of the following groups:

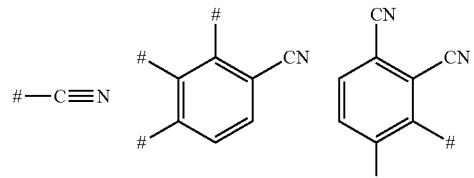

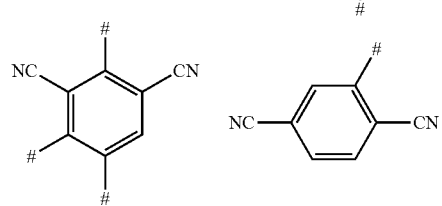

-continued

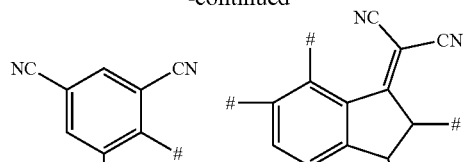

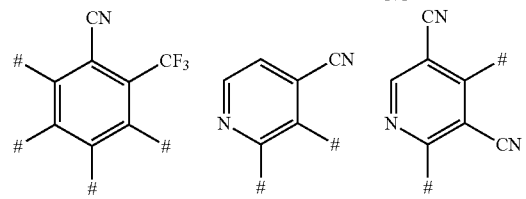

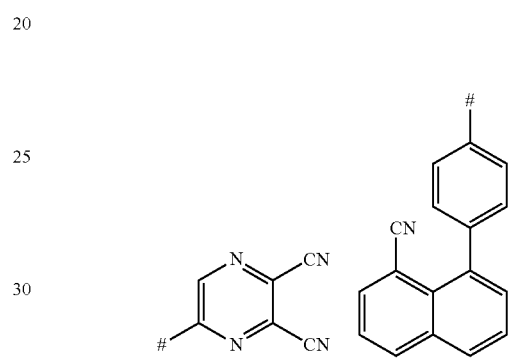

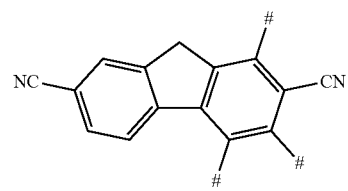

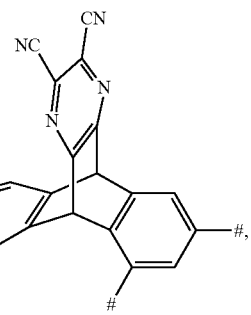

wherein # represents a bonding position in the Chemical Formula 1.

2. The compound according to claim 1, wherein the compound is selected from the group consisting of the following compounds:

P34

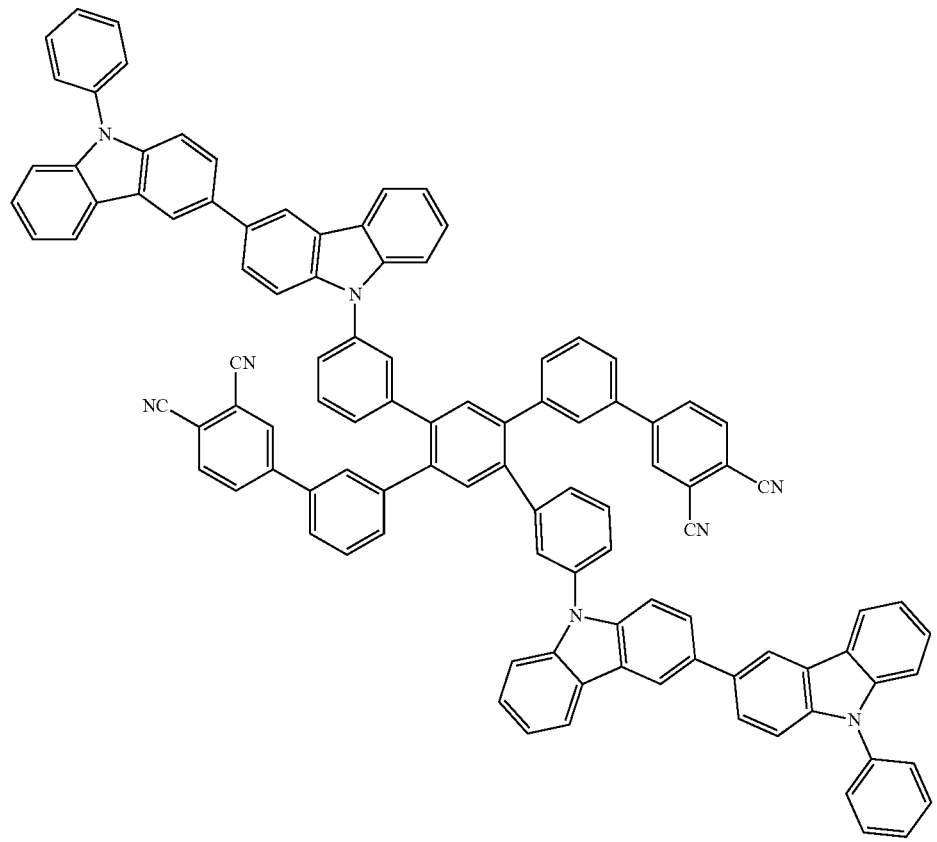

3. The compound according to claim 1, wherein an energy level difference between a lowest singlet energy level S1 and a lowest triplet energy level T1 of the compound satisfies: $\Delta E_{ST} = E_{S1} - E_{T1} \leq 0.30$ eV.

4. A display panel, comprising an organic light-emitting device, wherein the organic light-emitting device comprises an anode, a cathode disposed opposite to the anode, and a light-emitting layer disposed between the anode and the cathode, wherein a light-emitting material of the light-emitting layer comprises a host material and a guest material, and the guest material or the host material is one or more compounds according to claim 1.

5. A display apparatus, comprising the display panel according to claim 4.

* * * * *

UNITED STATES PATENT AND TRADEMARK OFFICE
CERTIFICATE OF CORRECTION

PATENT NO. : 11,758,809 B2
APPLICATION NO. : 16/732153
DATED : September 12, 2023
INVENTOR(S) : Gao et al.

Page 1 of 2

It is certified that error appears in the above-identified patent and that said Letters Patent is hereby corrected as shown below:

In the Claims

| Column | Line | |
|---|---|---|
| 126 | 45 | Change "wherein; wherein" to -- wherein -- |
| 129 | 20 | Formula #19 is incorrect and should read as follows: |

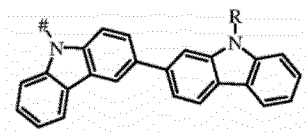

| 131-132 | | Missing compounds #P36 and #P39 should read as follows: |

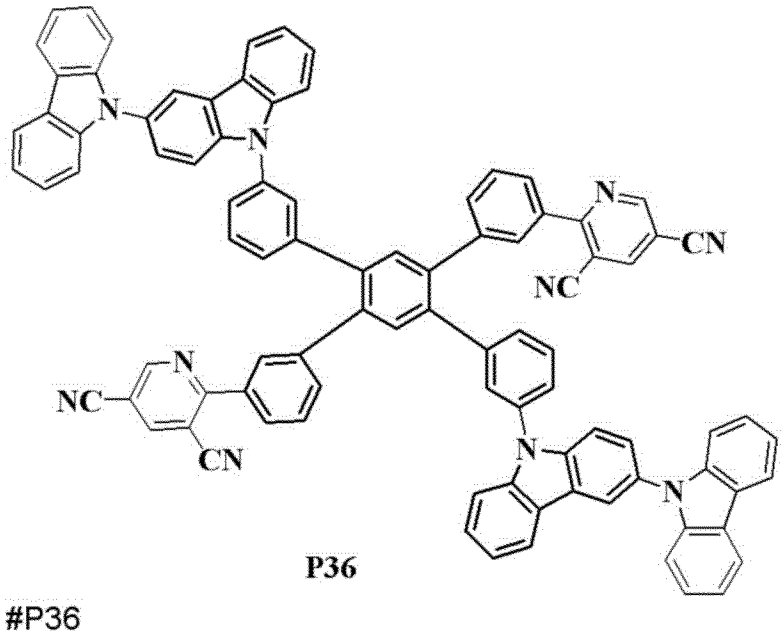

P36

Signed and Sealed this
Eleventh Day of June, 2024

Katherine Kelly Vidal
*Director of the United States Patent and Trademark Office*

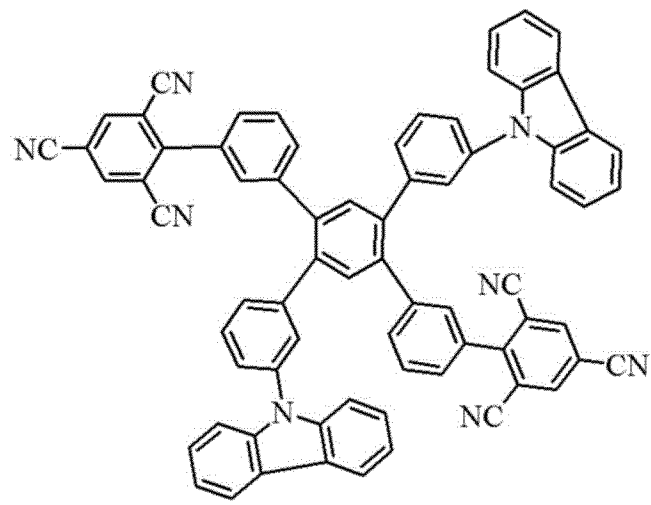
P39
P39